(12) United States Patent
Gono et al.

(10) Patent No.: US 7,892,169 B2
(45) Date of Patent: Feb. 22, 2011

(54) ENDOSCOPE APPARATUS

(75) Inventors: Kazuhiro Gono, Sagamihara (JP); Tetsuo Nonami, Hino (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 10/333,155

(22) PCT Filed: Jul. 18, 2001

(86) PCT No.: PCT/JP01/06205

§ 371 (c)(1),
(2), (4) Date: Jan. 16, 2003

(87) PCT Pub. No.: WO02/07588

PCT Pub. Date: Jan. 31, 2002

(65) Prior Publication Data

US 2003/0176768 A1     Sep. 18, 2003

(30) Foreign Application Priority Data

Jul. 21, 2000 (JP) .............................. 2000-221312
Jul. 27, 2000 (JP) .............................. 2000-227237

(51) Int. Cl.
A61B 1/06 (2006.01)
(52) U.S. Cl. ......................................... 600/178; 348/70
(58) Field of Classification Search ................. 600/109, 600/160, 178, 180–181; 348/70
See application file for complete search history.

(56) References Cited

U.S. PATENT DOCUMENTS

| 4,885,634 | A | * | 12/1989 | Yabe ........................... 348/71 |
| 4,945,409 | A | * | 7/1990 | Nakamura .................... 348/70 |
| 4,959,710 | A | * | 9/1990 | Uehara et al. ................ 600/109 |
| 4,983,019 | A | * | 1/1991 | Ikuno et al. .................. 600/181 |
| 5,001,556 | A | * | 3/1991 | Nakamura et al. ............ 348/70 |
| 5,111,281 | A | * | 5/1992 | Sekiguchi ..................... 348/65 |
| 5,111,804 | A | * | 5/1992 | Funakoshi ................... 600/109 |
| 5,159,380 | A | * | 10/1992 | Furuya et al. ............... 600/109 |
| 5,187,572 | A | | 2/1993 | Nakamura et al. |
| 5,209,220 | A | * | 5/1993 | Hiyama et al. .............. 600/109 |
| RE34,411 | E | * | 10/1993 | Nishioka et al. .............. 348/70 |
| 5,255,087 | A | * | 10/1993 | Nakamura et al. ............ 348/71 |

(Continued)

FOREIGN PATENT DOCUMENTS

JP    2-29612    1/1990

(Continued)

*Primary Examiner*—Philip R Smith
(74) *Attorney, Agent, or Firm*—Scully, Scott, Murphy & Presser, PC

(57) ABSTRACT

An endoscope device obtains tissue information of a desired depth near the tissue surface. A xenon lamp (11) in a light source (4) emits illumination light. A diaphragm (13) controls a quantity of the light that reaches a rotating filter. The rotating filter has an outer sector with a first filter set, and an inner sector with a second filter set. The first filter set outputs frame sequence light having overlapping spectral properties suitable for color reproduction, while the second filter set outputs narrow-band frame sequence light having discrete spectral properties enabling extraction of desired deep tissue information. A condenser lens (16) collects the frame sequence light coming through the rotating filter onto the incident face of a light guide (15). The diaphragm controls the amount of the light reaching the filter depending on which filter set is selected.

25 Claims, 62 Drawing Sheets

U.S. PATENT DOCUMENTS 5,749,830 A * 5/1998 Kaneko et al. ............... 600/160
5,902,230 A * 5/1999 Takahashi et al. ........... 600/109
6,438,396 B1 * 8/2002 Cook et al. .................. 600/310
6,496,719 B2 * 12/2002 Hayashi ....................... 600/478
6,734,894 B1 * 5/2004 Higuchi et al. ................ 348/69

FOREIGN PATENT DOCUMENTS

JP    10-151104    6/1998

* cited by examiner

IRREGULAR SURFACE STRUCTURE
CAPILLARY NETWORK NEAR SURFACE
BLOOD VESSEL NETWORK NEAR MIDDLE LAYERS
HEAVY BLOOD VESSEL NETWORK NEAR DEEP LAYERS

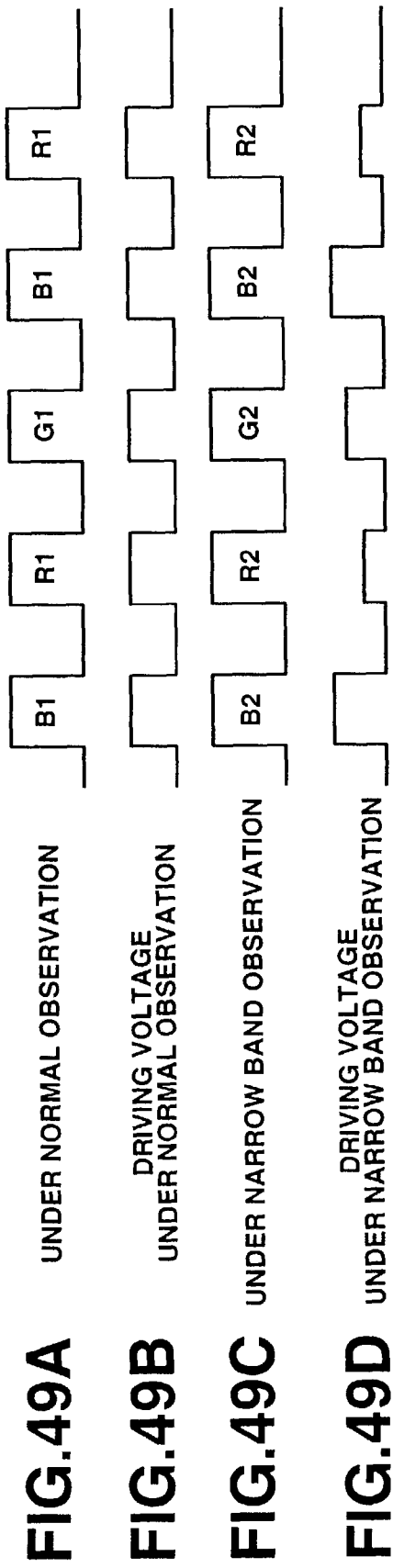

FIG.99
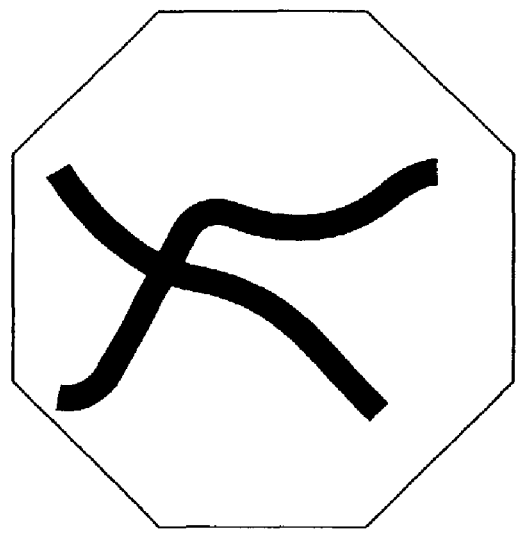
R2 IMAGE
G2 IMAGE
B2 IMAGE

ENDOSCOPE APPARATUS

TECHNICAL FIELD

The present invention relates to an endoscope device which captures images of living body tissue and performs signal processing thereon.

BACKGROUND ART

Conventionally, endoscope devices for irradiating illumination light and obtaining endoscopic images within body cavities have been widely used. With such endoscope devices, an electronic endoscope has image-pickup means for introducing an illumination light from a light source device into the body cavity using a light guide or the like and captures an image of the subject with the return light, and image-pickup signals from the image-pickup means are subjected to signal processing with a video processor, thereby displaying an endoscopic image on an observation monitor, so that an observation portion such as an affected area or the like is observed.

In the event of performing normal living body tissue observation with an endoscope device, white light of the visible light region is emitted with a light source device, frame sequence light is irradiated on the subject via, for example, a rotating filter such as RGB or the like, and the return light from this frame sequence light is synchronized with a video processor, so as to obtain a color image, or a color chip is disposed at the front face of the image-pickup surface of the image-pickup means of the endoscope and an image is captured by dividing the return light from white light into RGB, and image processing is performed at the video processor, thereby obtaining a color image.

On the other hand, the absorption properties and scattering properties of the light at the living body tissue differ according to the wavelength of the irradiated light, so in recent years, various types of infrared light endoscope devices, which are capable of observing the tissues at the deep part of the living body tissue by irradiating infrared light on the living body tissue as the illumination light, for example, are proposed.

However, with living body tissue diagnosis, while the deep tissue information near the surface of the tissue is also an important object of observation, with the above-described infrared light endoscope devices, only the deep tissue information deeper than the tissue surface can be obtained.

Also, in the event of irradiating white light on the living body tissue as RGB frame sequential light from a rotating filter, the wavelength regions thereof differ, so while image-pickup signals from light of each color has different deep part tissue information near the tissue surface of the living body tissue, but generally, the white light is separated into an RGB light with each of the wavelength regions overlapping, in order to obtain a more natural color image for the endoscopic image by the RGB frame sequential light.

That is, with overlapped RGB light, there is a problem that desired deep tissue information near the surface of the tissue of the living body tissue cannot be readily recognized, since a broad range of the deep tissue information is taken into the image-pickup signals of the light of each wavelength region.

The present invention has been made in the light of the above-described situation, and first, it is an object thereof to provide an endoscope device and light source device capable of obtaining tissue information of a desired depth near the tissue surface of the living body tissue.

Also, it is a second object of the present invention to provide an endoscope device whereby tissue information of a desired depth near the tissue surface of the living body tissue can be separated and visually recognized.

DISCLOSURE OF INVENTION

The endoscope device according to the present invention comprises illumination light supplying means for supplying illumination light including visible light region; an endoscope having image-pickup means for irradiating the illumination light on a subject and capturing an image of the subject by return light; and signal processing means for signal processing of image-pickup signals from the image-pickup means; wherein band restricting means, for restricting at least one of the plurality of wavelength regions of the illumination light and performing image formation of a band image of a discrete spectral distribution of the subject on the image-pickup means, are provided on the optical path from the illumination light supplying means to the image-pickup means.

BRIEF DESCRIPTION OF THE DRAWINGS

FIGS. 49a-d are diagrams illustrating the illumination timing of each band by the electric power supply unit shown in FIG. 47, and the light quantity control timing at that time.

FIG. 99 is a diagram illustrating RGB images captured when the narrow-band observation mode in FIG. 95.

BEST MODE FOR CARRYING OUT THE INVENTION

The following is a description of the embodiments of the present invention with reference to the drawings.

Figure 5:
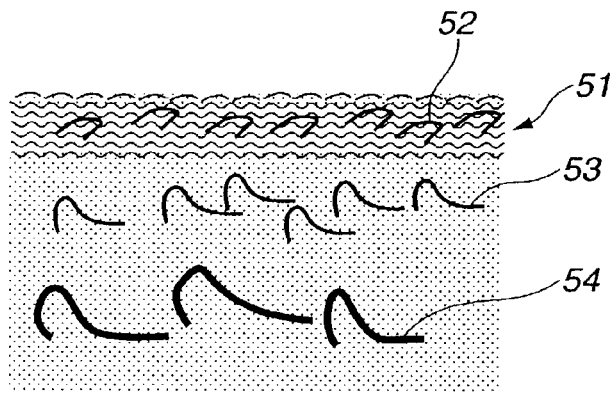
FIG. 5 is a diagram illustrating the structure of the living body tissue in the layer direction to be observed with the endoscope device shown in FIG. 1.
Figure 6:
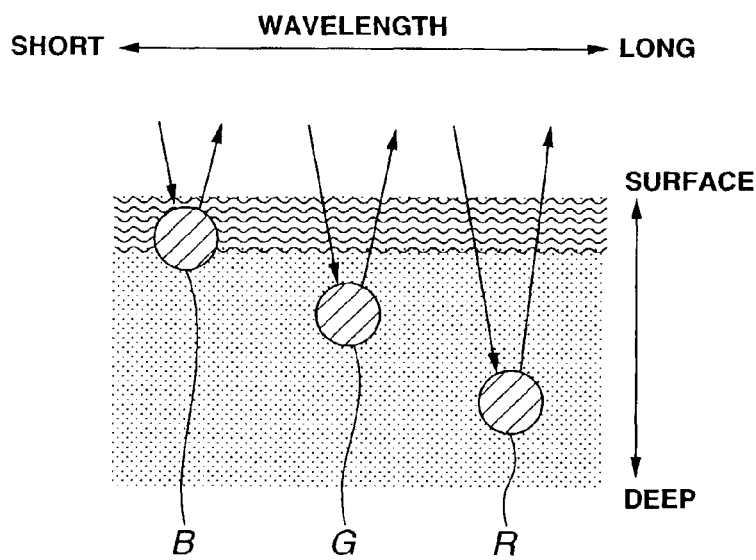
FIG. 6 is a diagram describing the state of the illumination light from the endoscope device shown in FIG. 1 reaching the living body tissue in the layer direction.
Figure 7A:
FIGS. 7a-c are diagrams illustrating each of the band images from frame sequence light transmitted through the first filter set shown in FIG. 3.
Figure 7B:
Figure 7C:
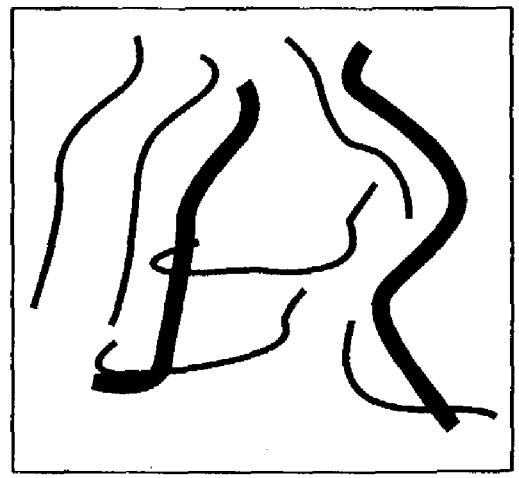
Figure 8A:
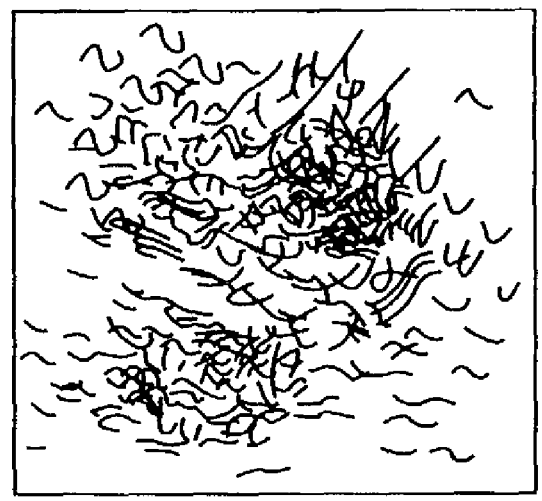
FIGS. 8a-c are diagrams illustrating each of the band images from frame sequence light transmitted through the second filter set shown in FIG. 4.
Figure 8B:
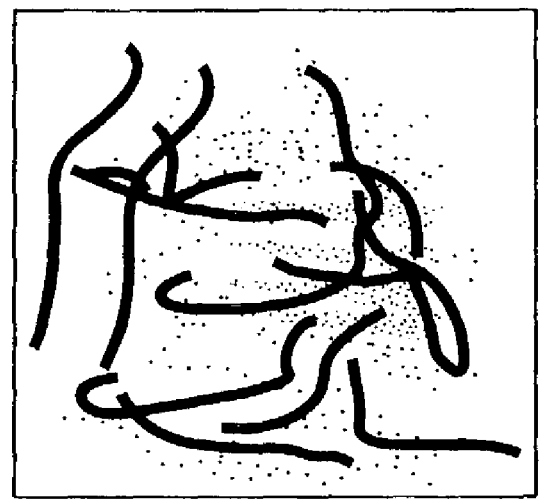
Figure 8C:
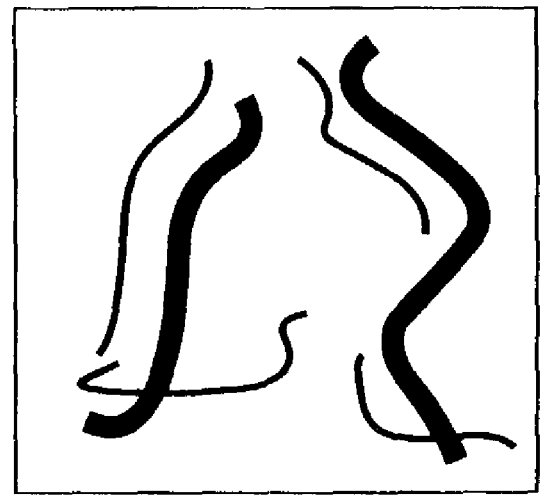
Figure 9:
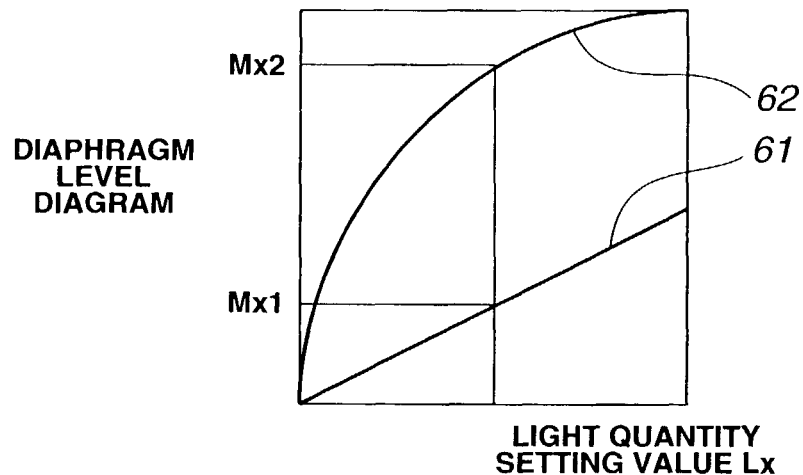
FIG. 9 is a diagram describing light adjustment control performed by a light adjusting circuit shown in FIG. 1.
Figure 10:
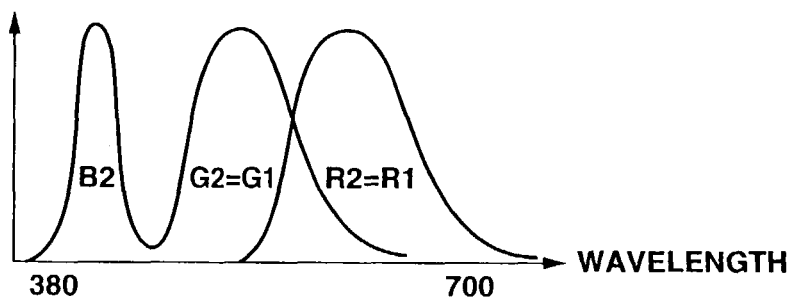
FIG. 10 is a diagram illustrating the spectral properties of a first modification made on the second filter set of the rotating filter shown in FIG. 2.
Figure 11:
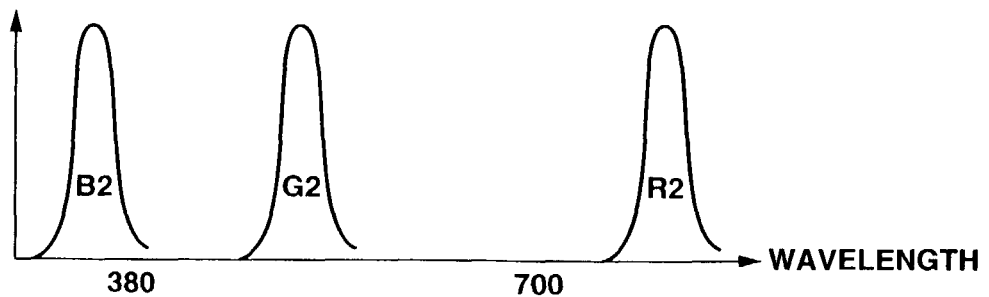
FIG. 11 is a diagram illustrating the spectral properties of a second modification made on the second filter set of the rotating filter shown in FIG. 2.
Figure 12:
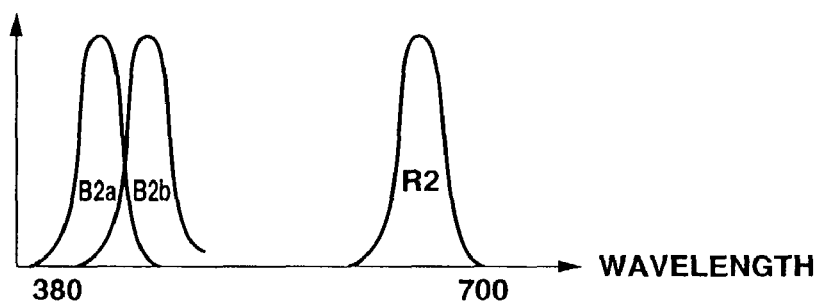
FIG. 12 is a diagram illustrating the spectral properties of a third modification made on the second filter set of the rotating filter shown in FIG. 2.
Figure 13:
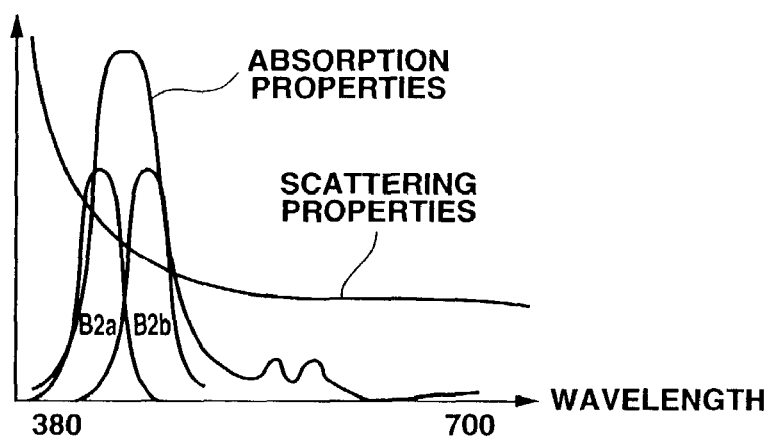
FIG. 13 is a diagram illustrating the spectral properties of a fourth modification made on the second filter set of the rotating filter shown in FIG. 2.
Figure 14:
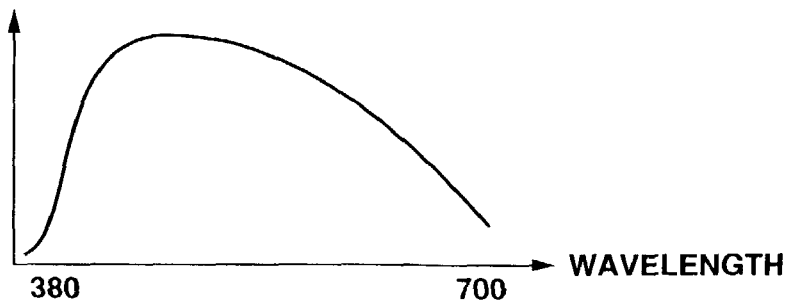
FIG. 14 is a diagram illustrating a first example of spectral distribution of a xenon lamp shown in FIG. 1.
Figure 15:
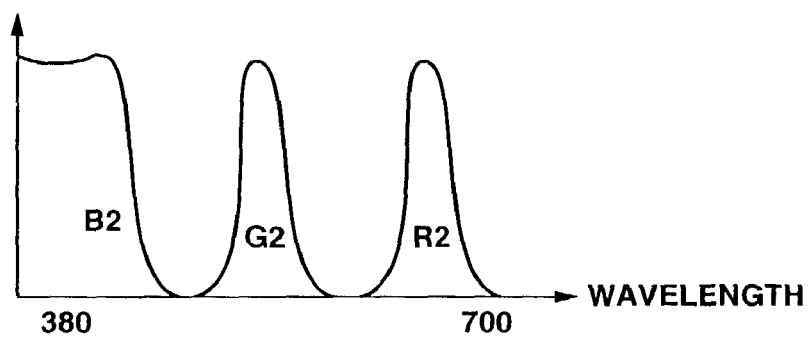
FIG. 15 is a diagram illustrating the spectral properties of a fourth modification made on the second filter set of the rotating filter in the event that the spectral distribution of the xenon lamp shown in FIG. 14 is applied.
Figure 16:
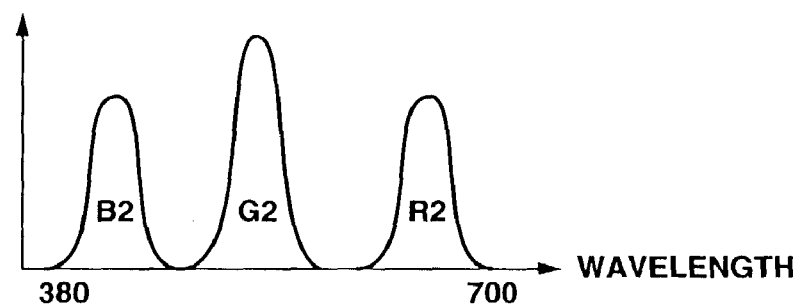
FIG. 16 is a diagram illustrating spectral properties of living body tissue illumination light with the fourth modification made on the second filter set of the rotating filter shown in FIG. 2.
Figure 17:
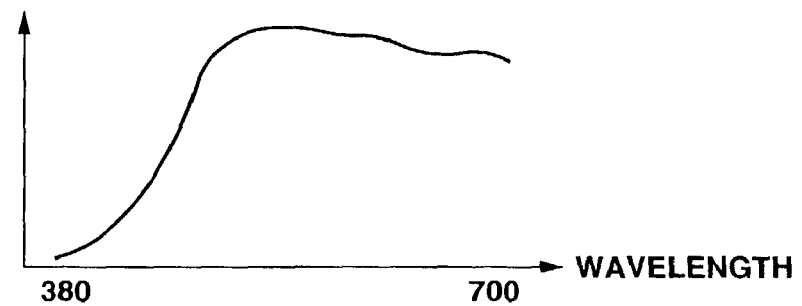
FIG. 17 is a diagram illustrating a second example of spectral distribution of the xenon lamp shown in FIG. 1.
Figure 18:
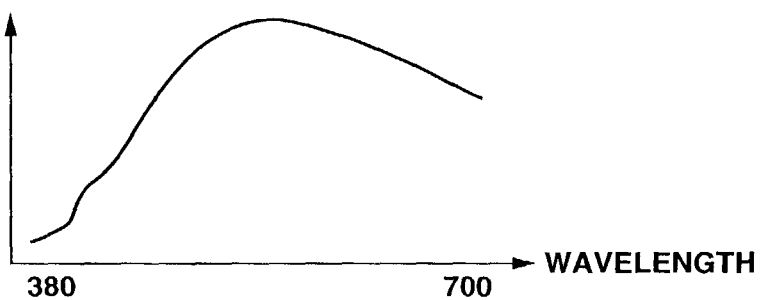
FIG. 18 is a diagram illustrating an example of spectral sensitivity properties of the CCD shown in FIG. 1.
Figure 19:
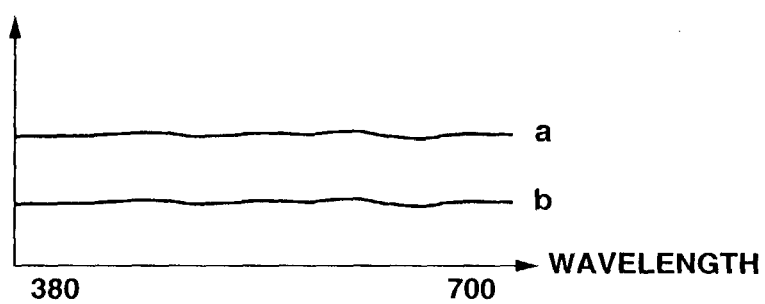
FIG. 19 is a diagram illustrating the spectral properties of a light reduction filter to be applied by vapor deposition to a fifth modification made on the second filter set of the rotating filter in the event that the spectral distribution of the xenon lamp is that in the second example and the spectral sensitivity properties of the CCD are those shown in FIG. 18.
Figure 20:
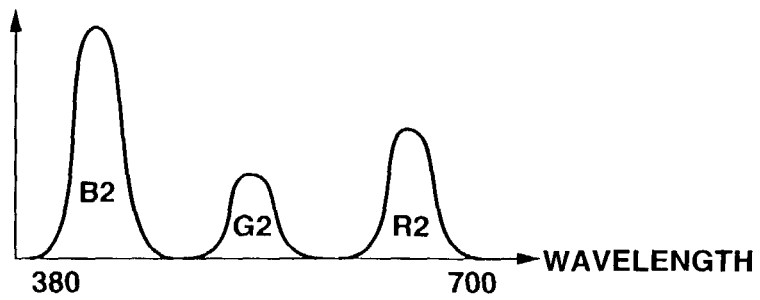
FIG. 20 is a diagram illustrating the spectral properties of the fifth modification made on the second filter set to which the light reduction filter shown in FIG. 19 has been applied by vapor deposition.
Figure 21:
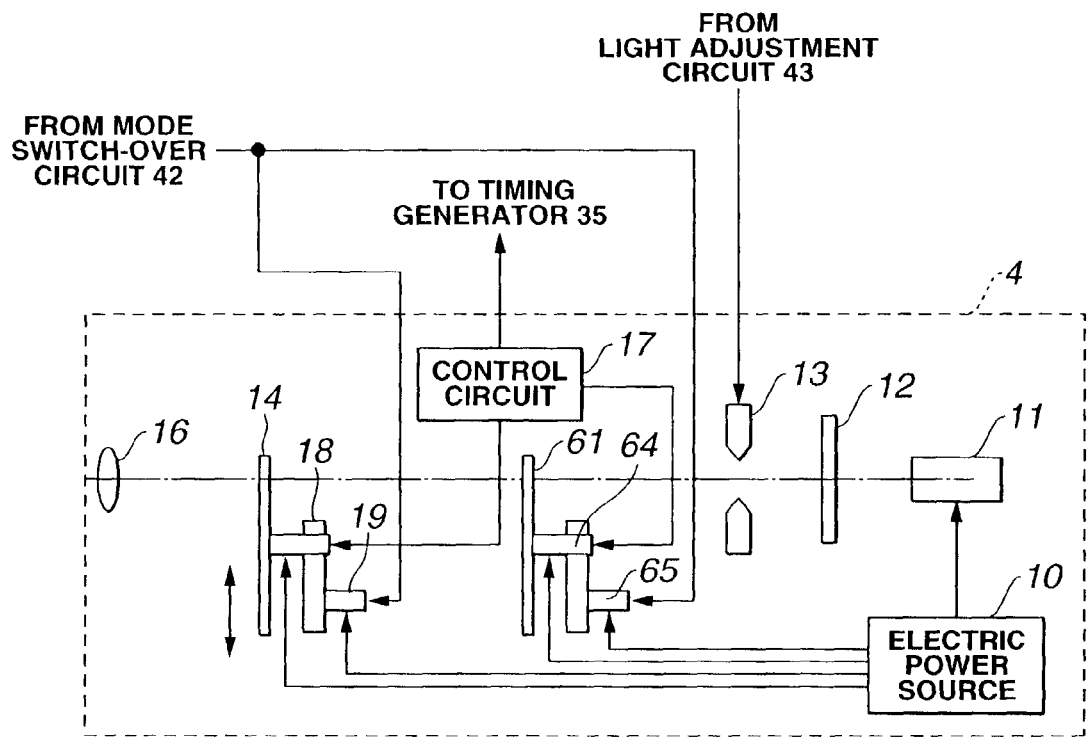
FIG. 21 is a configuration diagram illustrating a first modification of the light source device shown in FIG. 1.
Figure 22:
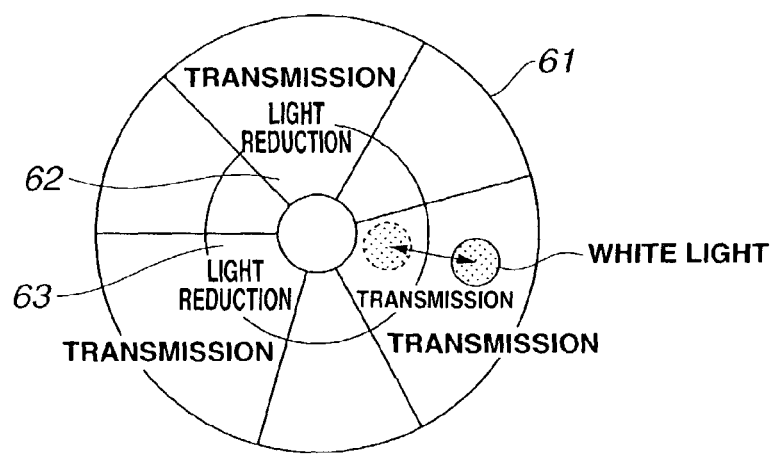
FIG. 22 is a configuration diagram illustrating the configuration of the light reduction rotating filter shown in FIG. 21.
Figure 23:
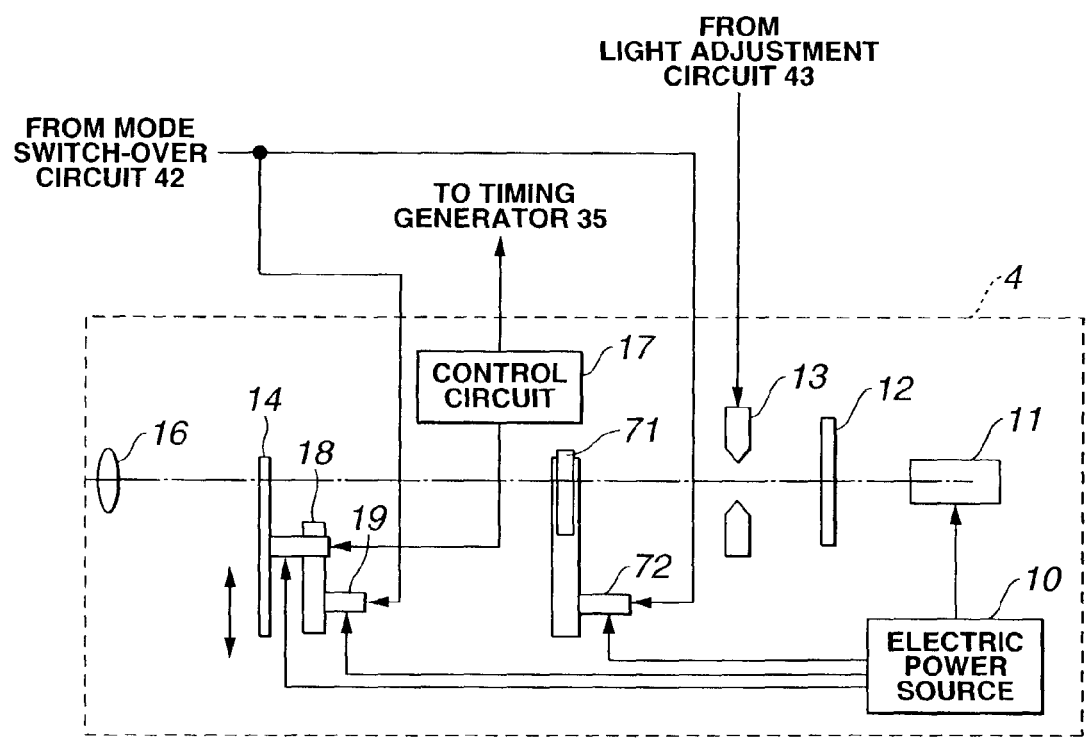
FIG. 23 is a configuration diagram illustrating the configuration of a second modification made on the light source device shown in FIG. 1.
Figure 24:
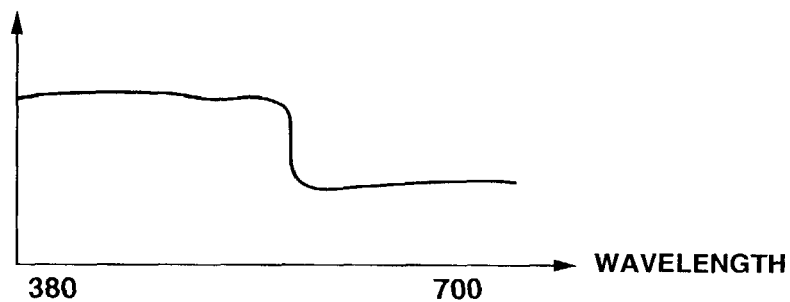
FIG. 24 is a diagram illustrating the light reduction properties of a first light reduction filter making up the light reduction filter shown in FIG. 23.
Figure 25:
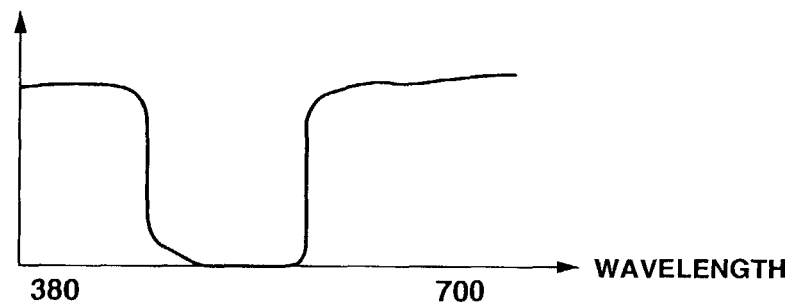
FIG. 25 is a diagram illustrating the light reduction properties of a second light reduction filter making up the light reduction filter shown in FIG. 23.
Figure 26:
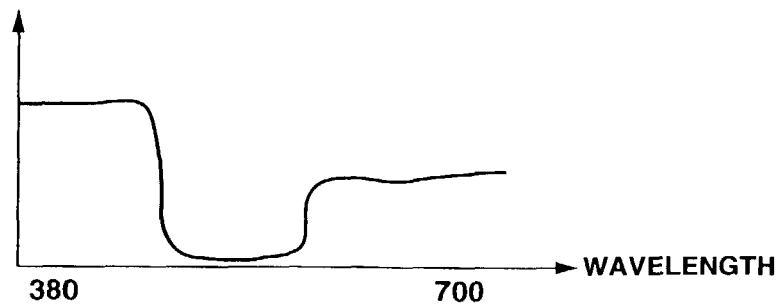
FIG. 26 is a diagram illustrating the light reduction properties of the light reduction filter shown in FIG. 23.
Figure 27:
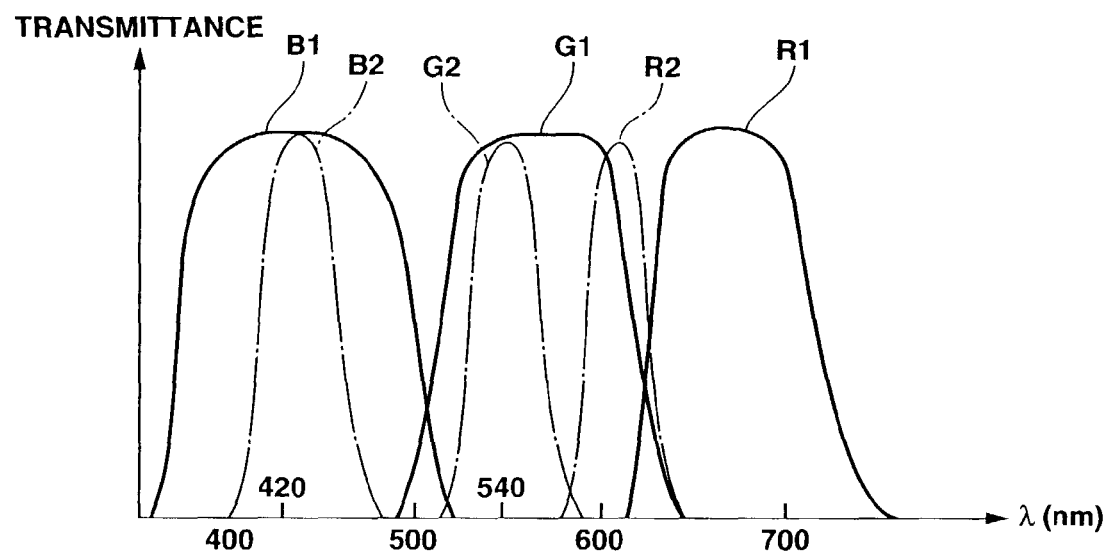
FIG. 27 is a diagram illustrating an example illustrating detailed spectral properties of the second filter set of the rotating filter shown in FIG. 2.
Figure 28:
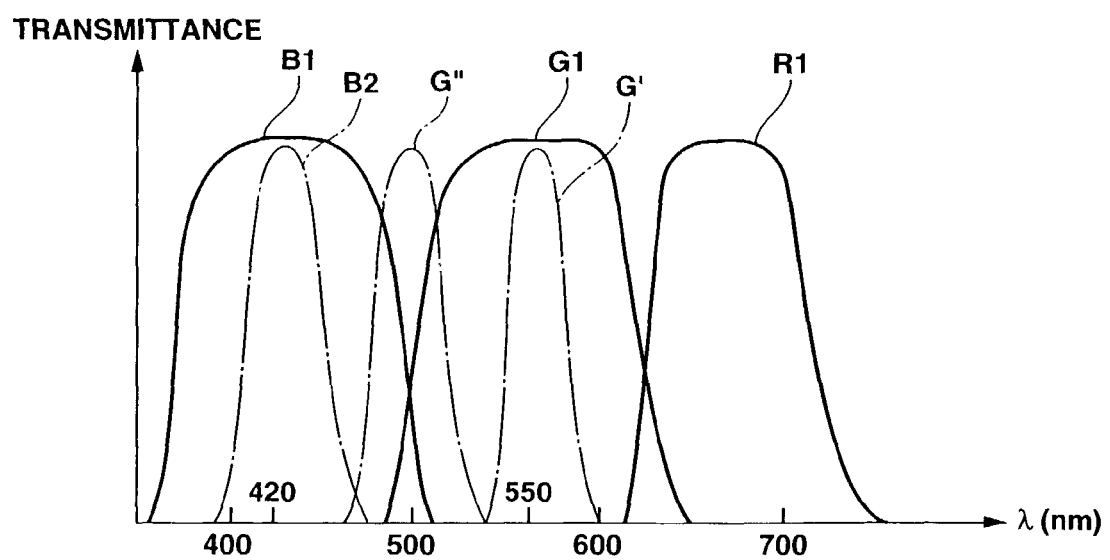
FIG. 28 is a diagram illustrating the spectral properties of a sixth modification made on the second filter set of the rotating filter shown in FIG. 2.
Figure 29:
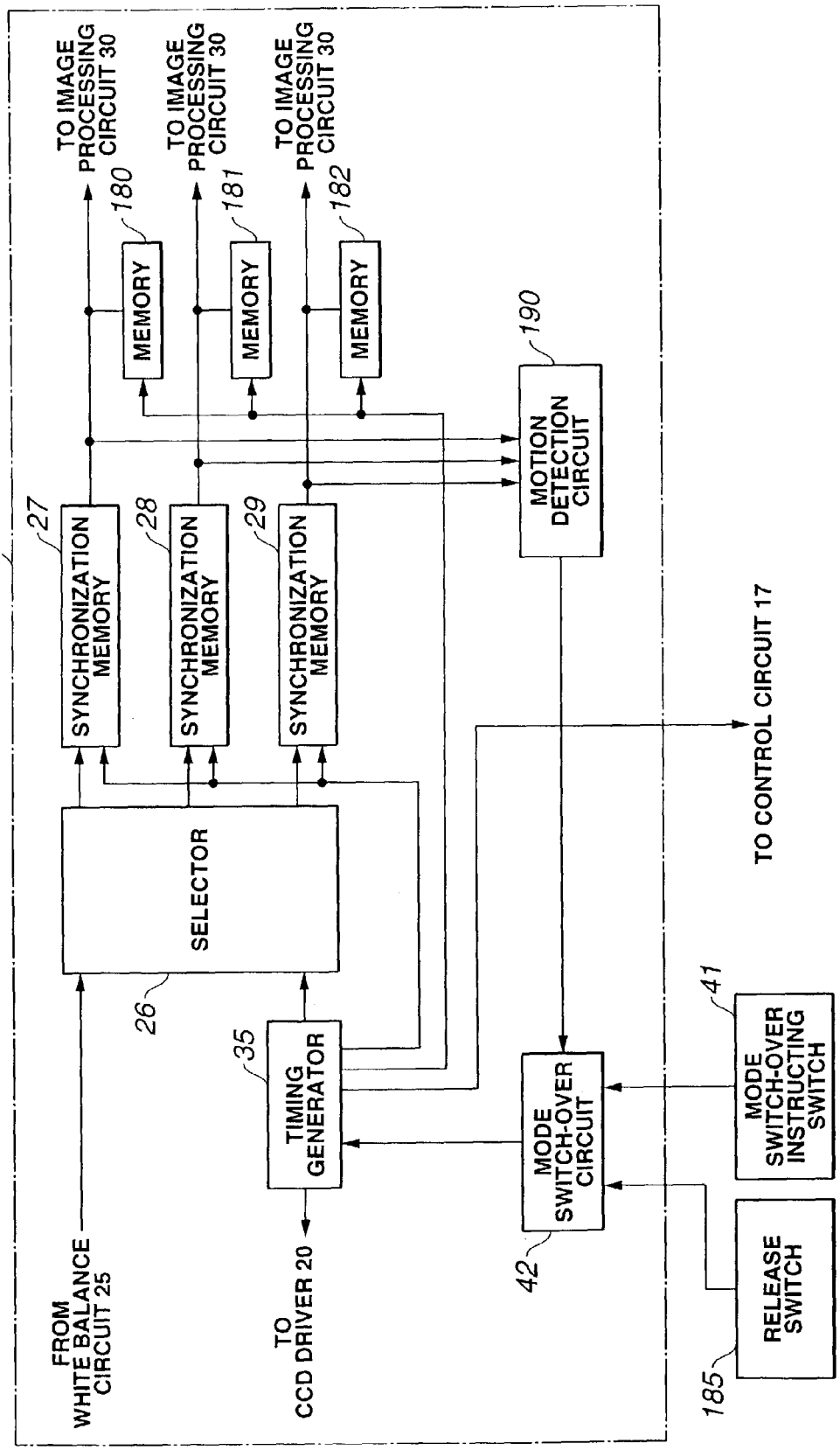
FIG. 29 is a diagram illustrating the configuration of the principal components of a modification made on the video processor shown in FIG. 1.
Figure 30:
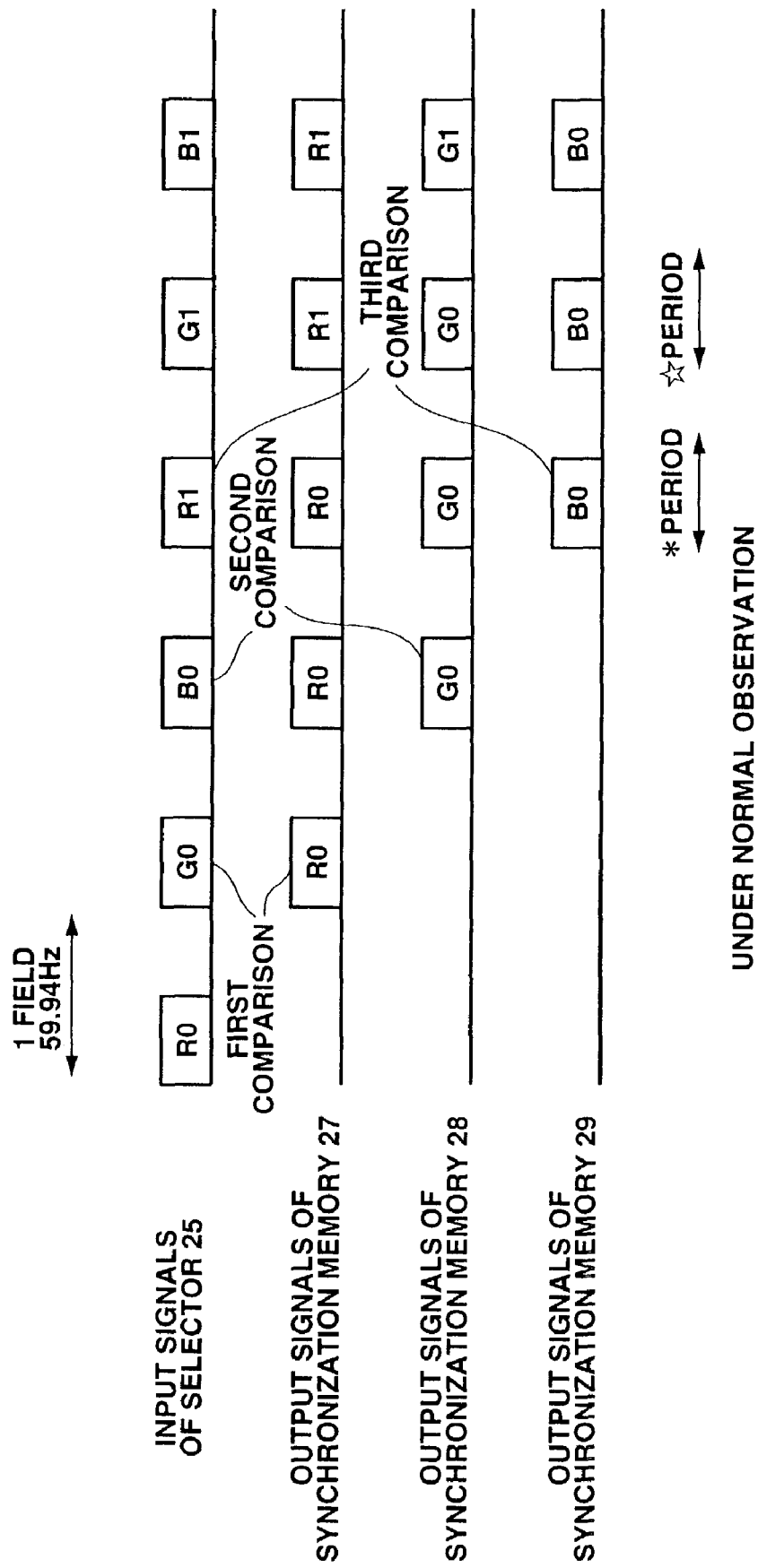
FIG. 30 is a first diagram describing the operation of the video processor shown in FIG. 29.
Figure 31:
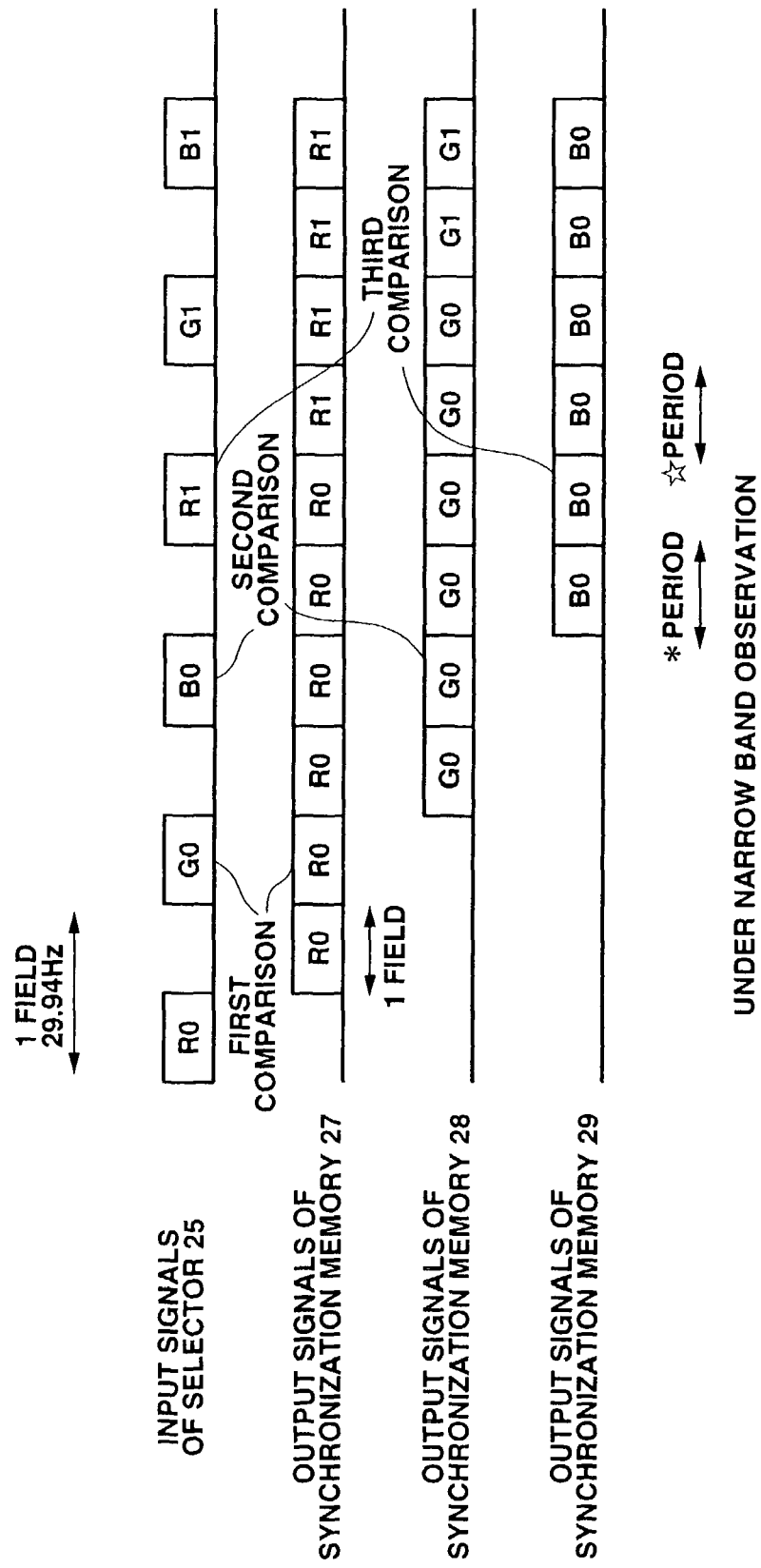
FIG. 31 is a second diagram describing the operation of the video processor shown in FIG. 29.
Figure 32:
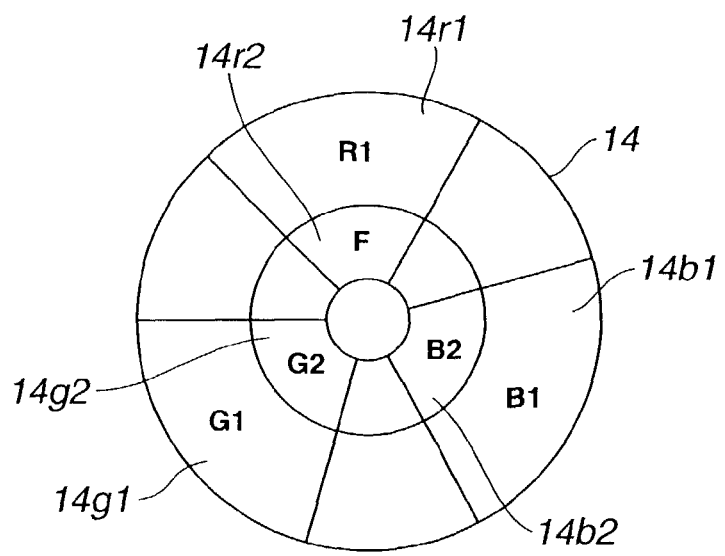
FIG. 32 is a diagram illustrating the spectral properties of a seventh modification made on the second filter set of the rotating filter shown in FIG. 2.
Figure 33:
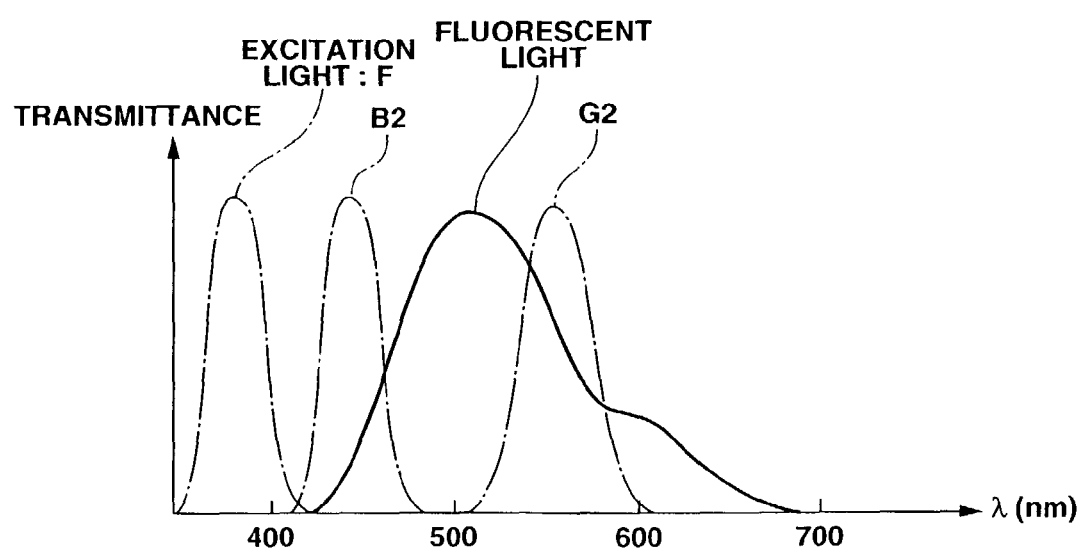
FIG. 33 is a diagram illustrating the spectral properties of the seventh modification made on the second filter set shown in FIG. 32.

First, a first embodiment of the present invention will be described with reference to FIG. 1 through FIG. 33. Here, FIG. 1 is a configuration diagram illustrating the configuration of an endoscope device, FIG. 2 is a configuration diagram illustrating the configuration of a rotating filter shown in FIG. 1, FIG. 3 is a diagram illustrating the spectral properties of a first filter set of the rotating filter shown in FIG. 2, FIG. 4 is a diagram illustrating the spectral properties of a second filter set of the rotating filter shown in FIG. 2, FIG. 5 is a diagram illustrating the structure of the living body tissue in the layer direction to be observed with the endoscope device shown in FIG. 1, FIG. 6 is a diagram describing the state of the illumination light from the endoscope device shown in FIG. 1 reaching the living body tissue in the layer direction, FIG. 7 is a diagram illustrating each of the band images from frame sequence light transmitted through the first filter set shown in FIG. 3, FIG. 8 is a diagram illustrating each of the band images from frame sequence light transmitted through the second filter set shown in FIG. 4, FIG. 9 is a diagram describing light adjustment control performed by a light adjusting circuit shown in FIG. 1, FIG. 10 is a diagram illustrating the spectral properties of a first modification made on the second filter set of the rotating filter shown in FIG. 2, FIG. 11 is a diagram illustrating the spectral properties of a second modification made on the second filter set of the rotating filter shown in FIG. 2, FIG. 12 is a diagram illustrating the spectral properties of a third modification made on the second filter set of the rotating filter shown in FIG. 2, FIG. 13 is a diagram describing the operations of a third modification made on the second filter set of the rotating filter shown in FIG. 2, FIG. 14 is a diagram illustrating a first example of spectral distribution of a xenon lamp shown in FIG. 1, FIG. 15 is a diagram illustrating the spectral properties of a fourth modification made on the second filter set of the rotating filter in the event that the spectral distribution of the xenon lamp shown in FIG. 14 is applied, FIG. 16 is a diagram illustrating spectral properties of living body tissue illumination light with the fourth modification made on the second filter set shown in FIG. 14, FIG. 17 is a diagram illustrating a second example of spectral distribution of the xenon lamp shown in FIG. 1, FIG. 18 is a diagram illustrating an example of spectral sensitivity properties of the CCD shown in FIG. 1, FIG. 19 is a diagram illustrating the spectral properties of a light reduction filter to be applied by vapor deposition to a fifth modification made on the second filter set of the rotating filter in the event that the spectral distribution of the xenon lamp is that in the second example and the spectral sensitivity properties of the CCD are those shown in FIG. 18, FIG. 20 is a diagram illustrating the spectral properties of the fifth modification made on the second filter set to which the light reduction filter shown in FIG. 19 has been applied by vapor deposition, FIG. 21 is a configuration diagram illustrating a first modification of the light source device shown in FIG. 1, FIG. 22 is a configuration diagram illustrating the configuration of the light reduction rotating filter shown in FIG. 21, FIG. 23 is a configuration diagram illustrating the configuration of a second modification made on the light source device shown in FIG. 1, FIG. 24 is a diagram illustrating the light reduction properties of a first light reduction filter making up the light reduction filter shown in FIG. 23, FIG. 25 is a diagram illustrating the light reduction properties of a second light reduction filter making up the light reduction filter shown in FIG. 23, FIG. 26 is a diagram illustrating the light reduction properties of the light reduction filter shown in FIG. 23, FIG. 27 is a diagram illustrating an example illustrating detailed spectral properties of the second filter set of the rotating filter shown in FIG. 2, FIG. 28 is a diagram illustrating the spectral properties of a sixth modification made on the second filter set of the rotating filter shown in FIG. 2, FIG. 29 is a diagram illustrating the configuration of the principal components of a modification made on the video processor shown in FIG. 1, FIG. 30 is a first diagram describing the operations of the video processor shown in FIG. 29, FIG. 31 is a second diagram describing the operations of the video processor shown in FIG. 29, FIG. 32 is a diagram illustrating the spectral properties of a seventh modification made on the second filter set of the rotating filter shown in FIG. 2, and FIG. 33 is a diagram illustrating the spectral properties of the seventh modification made on the second filter set shown in FIG. 32.

Figure 1:
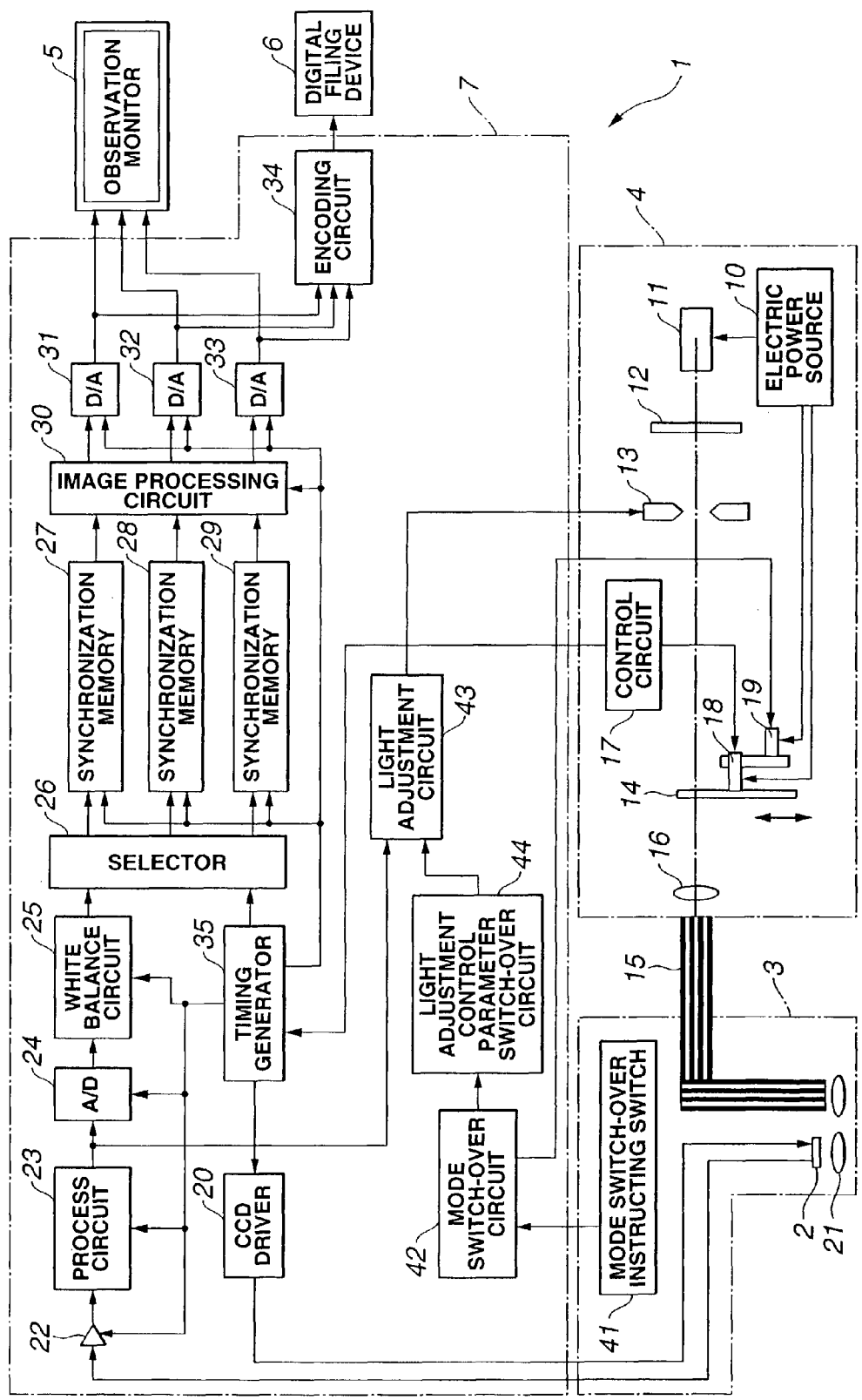
FIG. 1 is a configuration diagram illustrating the configuration of an endoscope device according to a first embodiment of the present invention.

As shown in FIG. 1, the endoscope device 1 according to the present embodiment is configured of an electronic endoscope 3 which is inserted inside the body cavity and which has a CCD 2 serving as image-pickup means for capturing images of tissue within the body cavity, a light source device 4 for supplying illumination light to the electronic endoscope 3, and a video processor 7 for subjecting image-pickup signals from the CCD 2 of the electronic endoscope 3 to signal processing and displaying endoscopic images on an observation monitor 5 or encoding the endoscopic images and outputting to an image filing device 6 as compressed images.

The light source device 4 is configured of a xenon lamp 11 for emitting illumination light, a heat ray cut filter 12 for shielding heat rays from the white light, a diaphragm device 13 for controlling the light quantity of the white light through the heat ray cut filter 12, a rotating filter 14 for turning the illumination light into frame sequence light, a condenser lens 16 for collecting the frame sequence light coming through the rotating filter 14 onto the incident face of a light guide 15 disposed within the electronic endoscope 3, and a control circuit 17 for controlling the rotation of the rotating filter 14.

Figure 2:
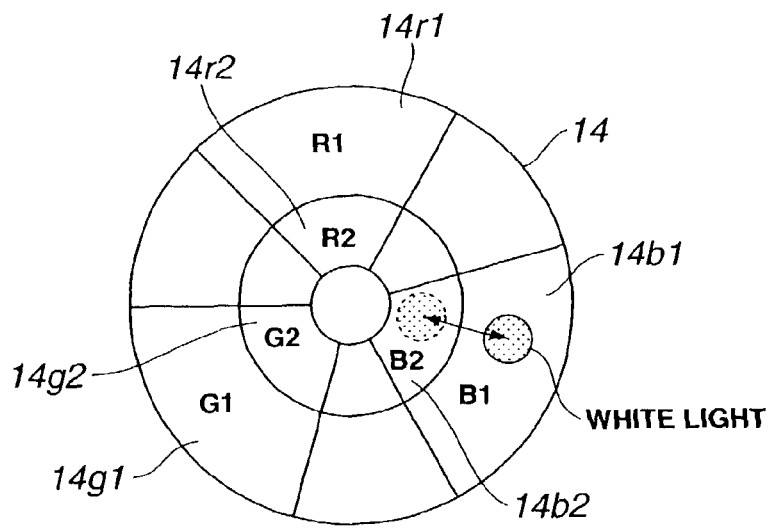
FIG. 2 is a configuration diagram illustrating the configuration of a rotating filter shown in FIG. 1.
Figure 3:
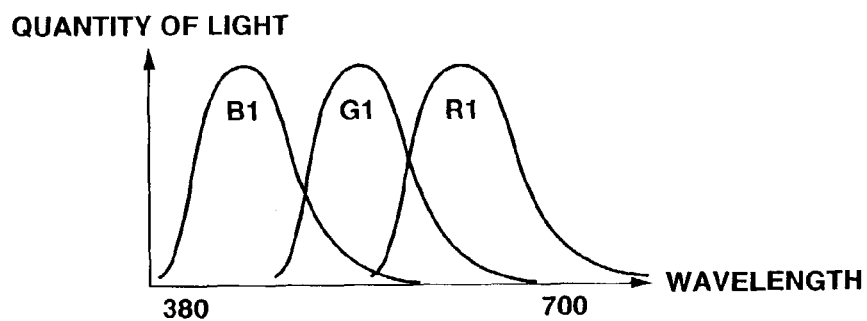
FIG. 3 is a diagram illustrating the spectral properties of a first filter set of the rotating filter shown in FIG. 2.
Figure 4:
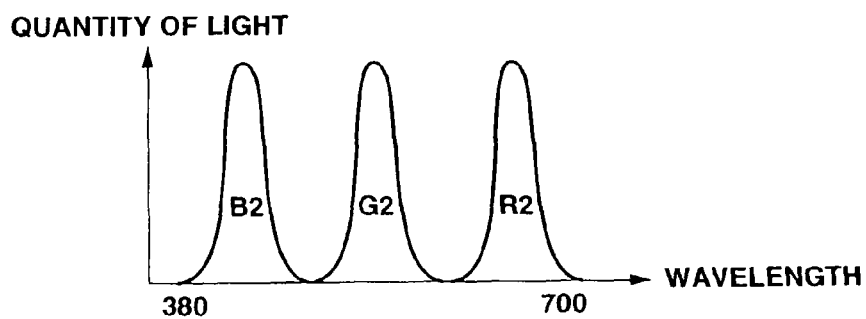
FIG. 4 is a diagram illustrating the spectral properties of a second filter set of the rotating filter shown in FIG. 2.

As shown in FIG. 2, the rotating filter 14 is formed in a disk-like shape and has a double structure with the center as the rotating axis, wherein an R1 filter 14r1, a G1 filter 14g1, and a B1 filter 14b1 making up a first filter set for outputting frame sequence light having overlapping spectral properties suitable for color reproduction such as indicated in FIG. 3 are situated on the outer sector, and wherein an R2 filter 14r2, a G2 filter 14g2, and a B2 filter 14b2 making up a second filter set for outputting narrow-band frame sequence light having discrete spectral properties enabling extraction of desired deep tissue information such as indicated in FIG. 4 are situated on the inner sector. As shown in FIG. 1, the rotating filter 14 is rotated by the control circuit 17 performing driving control of a rotating filter motor 18, and movement in the radial direction (movement which is perpendicular to the optical path of the rotating filter 14, which is selectively moving the first filter set or second filter set of the rotating filter 14 onto the optical path) is performed by a mode switch-over motor 19 based on control signals from a mode switch-over circuit 42 within the later-described video processor 7.

Note that electric power is supplied to the xenon lamp 11, diaphragm device 13, rotating filter motor 18, and mode switch-over motor 19, from the electric power supply unit 10.

Returning to FIG. 1, the video processor 7 is configured comprising a CCD driving circuit 20 for driving the CCD 2, an amplifier 22 for amplifying image-pickup signals wherein images are captured in the body cavity tissue by the CCD 2 through an objective optical system 21, a process circuit 23 for performing correlated double sampling and noise reduction and so forth, with regard to image-pickup signals coming through the amplifier 22, an A/D converter 24 for converting the image-pickup signals passing through the process circuit 23 into image data of digital signals, a white balance circuit 25 for subjecting the image data from the A/D converter 24 to white balance processing, a selector 26 and synchronizing memories 27, 28, and 29, for synchronizing the frame sequence light from the rotating filter 14, an image processing circuit 30 for reading out each set of image data of the frame sequence light stored in the synchronizing memories 27, 28, 29, and subjecting these to gamma correction processing, outline enhancement processing, color processing, etc., D/A circuits 31, 32, and 33, for converting the image data from the image processing circuit 30 into analog signals, an encoding circuit 34 encoding the output of the D/A circuits 31, 32, and 33, and a timing generator 35 for inputting synchronizing signals synchronized with the rotation of the rotating filter 14 from the control circuit 17 of the light source device 4, and outputting various types of timing signals to the above-described circuits.

Also, a mode switch-over switch 41 is provided in the electronic endoscope 2, with the output of this switch-over switch 41 being output to the mode switch-over circuit 42 within the video processor 7. The mode switch-over circuit 42 of the video processor 7 makes output of control signals to a light adjusting circuit 43, a light adjustment control parameter switch-over circuit 44, and the mode switch-over motor 19 of the light source 4. The light adjustment control parameter switch-over circuit 44 outputs light adjustment control parameters corresponding to the first filter set or second filter set of the rotating filter 14 to the light adjusting circuit 43, and the light adjusting circuit 43 controls the diaphragm device 13 of the light source device 4 based on the control signals from the mode switch-over circuit 42 and light adjusting parameters from the light adjustment control parameter switch-over circuit 44, so as to perform appropriate brightness control.

Next, the operations of the endoscope device according to the present embodiment configured thus will be described.

As shown in FIG. 5, a body cavity tissue 51 often has a structure wherein there is a distribution of different absorbent material such as blood vessels in the depth direction, for example. There is primarily a greater distribution of capillaries 52 near the surface of mucus membranes, blood vessels 53 which are thicker than the capillaries are also distributed along with the capillaries at the middle layer which is deeper than this layer, and even thicker blood vessels 54 are distributed at even deeper layers.

On the other hand, the permeation depth of the light in the depth direction as to the body cavity tissue 51 is dependent on the wavelength of light, and with illumination light containing the visible region, as shown in FIG. 6, in the case of light with a short wavelength such as blue (B), the light only reaches around the surface layer due to the absorption properties and scattering properties at the living body tissue, being subjected to absorption and scattering within the range up to that depth, so light coming out from the surface is observed. Also, in the case of green (G) light with a wavelength longer than that of blue (B) light, the light reaches a depth deeper than the range where the blue (B) light reaches, is subjected to absorption and scattering within the range at that depth, and light coming out from the surface is observed. Further, red (R) light with a wavelength longer than that of green (G) light, reaches a range even deeper.

At the time of performing normal observation, the mode switch-over motor 19 is controlled by the mode switch-over circuit within the video processor 7 with control signals, so that the R1 filter 14r1, G1 filter 14g1, and B1 filter 14b1, making up the first filter set of the rotating filter 14, are positioned on the optical path of the illumination light.

With the R1 filter 14r1, G1 filter 14g1, and B1 filter 14b, the wavelength regions are each overlapped as shown in FIG. 3, so at the time of normal observation of the body cavity tissue 51, a band image having shallow layer and middle layer tissue information containing a great amount of tissue information at the shallow layer such as shown in "a" in FIG. 7 is captured in the image-pickup signals taken by the CCD 2 with the B1 filter 14b1, a band image having shallow layer and middle layer tissue information containing a great amount of tissue information at the middle layer such as shown in "b" in FIG. 7 is captured in the image-pickup signals taken by the CCD 2 with the G1 filter 14g1, and further, a band image having middle layer and deep layer tissue information containing a great amount of tissue information at the deep layer such shown in "c" in FIG. 7 is captured in the image-pickup signals taken by the CCD 2 with the R1 filter 14r1.

These RGB image-pickup signals are synchronized with the video processor 7 and subjected to signal processing, thus enabling an endoscopic image with desired or natural color reproduction to be obtained as an endoscopic image.

On the other hand, upon the mode switch-over switch 41 of the electronic endoscope 3 being pressed, the signals thereof are input to the mode switch-over circuit 42 of the video processor 7. The mode switch-over circuit 42 outputs control signals to the mode switch-over motor 19 of the light source device 4, thereby moving the first filter set of the rotating filter 14 that was on the optical path at the time of normal observation, and drives the rotating filter 14 with regard to the optical path so that the second filter set is positioned upon the optical path.

In the event of performing narrow-band light observation of the body cavity tissue 51 with the second filter set, the R2 filter 14r, G2 filter 14g, and B2 filter 14b2 make the illumination light to be narrow-band frame sequence light with discrete spectral properties as shown in FIG. 4, so a band image having tissue information at a shallow layer such as shown in "a" in FIG. 8 is captured in the image-pickup signals taken by the CCD 2 with the B2 filter 14b2, a band image having tissue information at the middle layer such as shown in "b" in FIG. 8 is captured in the image-pickup signals taken by the CCD 2 with the G2 filter 14g2, and a band image having tissue information at the deep layer such as shown in "c" in FIG. 8 is captured in the image-pickup signals taken by the CCD 2 with the R2 filter 14r2.

As can be clearly understood from FIG. 3 and FIG. 4, at this time, the quantity of transmitted light from the second filter set is less than the quantity of transmitted light from the first filter set, because the bands thereof are narrowed, so the light adjusting circuit 43 controls the diaphragm device 13 by the light adjustment control parameter switch-over circuit 44 outputting light adjustment control parameters according to the first filter set or second filter set of the rotating filter 14 to the light adjusting circuit 43, thereby, as shown in FIG. 9, controlling the diaphragm device 13 when making narrow-band light observation so as to control light quantity Mx with a diaphragm control curve 62 corresponding to a set value Lx, with respect to, for example, a linear diaphragm control line 61 by the diaphragm device 13 in normal observation, corresponding to the set value Lx on an unshown setting panel of the video processor 7.

Specifically, the aperture level value corresponding to the light quantity setting value Lx changes from Mx1 to Mx2 as shown in FIG. 9, being interlocked with changing the first filter set to the second filter set, and consequently, the diaphragm is controlled in the direction of being opened, and acts to compensate for reduction in the quantity of illumination light by the filter which narrows the band.

Thus, image data with sufficient brightness can be obtained even when making narrow-band light observation.

Thus, according to the present embodiment, a transfer to narrow-band light observation can be made by pressing the mode switch-over switch 41 as necessary so as to switch from the first filter set of the rotating filter 14 to the second filter set while performing normal observation of the body cavity tissue 51, and in this narrow-band light observation, each of the layers of the body cavity tissue 51 can be obtained as image-pickup signals in the state of the living body tissue of each being separated by the second filter set of the rotating filter 14, and also image-pickup signals of a suitable light quantity can be obtained by controlling the diaphragm device 13, so tissue information about each of the layers of the body cavity tissue 51 which is important for diagnosis can be visually recognized in a sure manner and can be diagnosed in a more accurate manner.

Now, while the second filter set has been made to be a filter set with illumination light spectrum properties such as shown in FIG. 4 (R2 filter 14r2, G2 filter 14g2, and B2 filter 14b2), the invention is not restricted to this, and as a first modification of the second filter set, the second filter may be a filter set which generates narrow-band frame sequence light with discrete spectral properties as shown in FIG. 10, for example, from the illumination light. With the filter set according to this first modification, the G filter and R filter are the same as the G filter and the R filter of the first filter set, and only the B filter carries a narrow bandwidth. This modification is particularly suitable for cases wherein there is interest in the capillaries structures and the like near the surface of the living body tissue, and conventional images suffice for the other band images.

Also, the filter properties are not restricted to visible light, and as a second modification of the second filter set, the second filter may be a filter set which generates narrow-band frame sequence light with discrete spectral properties as shown in FIG. 11, for example, from the illumination light. This filter set according to the second modification is suitable for obtaining any image information not applicable with normal observation, by setting B to the near-ultraviolet region and R to the near-infrared region, in order to observe the irregular portions at the surface of the organism and absorbents at extremely deep layers.

Further, as the third modification of the second filter set, the second filter may be a filter set comprising two filters B2a and B2b which come close at the near-wavelength region, instead of the G filter, as shown in FIG. 12. This is suitable for visualizing minute differences in scattering properties rather than absorption properties, using the fact that the wavelength bandwidth in this area only permeates to around the extreme surface layer of the organism. That is, as shown in FIG. 13, configuring the filter at a position where the scattering properties greatly change such that the absorption properties of the organism are approximately equal at the center wavelength of B2a and B2b is suitable for visualizing scattering properties near the surface. Medically, application can be envisioned for diagnosis for recognizing disorders involving disarray in cell arrays near the surface of mucous membranes, such as for early cancer or the like.

Also, generally, xenon lamps and the like are often manufactured so as to shield ultraviolet light. FIG. 14 shows an example of spectral distribution of the illumination light source. Accordingly, with the B region in the second filter set, even in the event that the short wavelength side is given open properties as a transmitting area as shown in FIG. 15, the properties are as such as shown in FIG. 16 in the combination with a spectral properties of the light source, and consequently, narrow-band illumination light properties can be realized. Also, manufacturing of the optical filter is normally often performed by vapor deposition of a multi-layer interference film filter, and with that manufacturing method, the vapor deposition in with many layers of film must be performed in order to yield narrow-band for the spectral transmissivity properties thereof, resulting in increased costs and thicker filters, but the manufacturing costs and thickness can be reduced by using the lump properties in this way and giving open properties to one side.

Also, in the event that the spectral distribution of the light source are such as shown in FIG. 17, or in the event that the spectral sensitivity properties of the CCD are as shown in FIG. 18, the light adjustment is set somewhat brighter to compensate for the reduction in light quantity by narrowing the bandwidth, in association with switching over from the first filter set of the rotating filter 14 to the second filter set, and consequently it can be conceived that the B2 band image is suitable, but that the G2 band image and R2 band image tend to be saturated. Or, the white balance is adjusted at the white balance circuit 25 shown in FIG. 1, and consequently, the B2 band image with a low brightness level is excessively amplified by the second filter set, light source device, and CCD sensitivity properties, resulting in an image with poor SN being observed.

Accordingly, it is necessary to control not only the bandwidth properties but also the peak transmittance properties as well, taking into consideration factors which affect the system spectral sensitivity, such as light source spectral distribution properties, CCD spectral sensitivity properties, and so forth.

Accordingly, taking into consideration the system spectral sensitivity properties other than filter, and light adjustment properties, an arrangement may be configured as the fifth modification of the second filter set, wherein a light reducing filter having light reducing properties "a" and "b" as shown in FIG. 19 is vapor-deposited or adhered to the R2 filter 14r2 or G2 filter 14g2 of the rotating filter 14 to obtain an image with suitable brightness. Consequently, a narrow-band filter set having properties such as shown in FIG. 20, can be obtained. In this way, not only the bandwidth properties, but also the transmissivity properties thereof can also be suitably set, so images with optimal brightness for each band can be observed.

As a method for controlling not only bandwidth properties but also peak transmissivity properties, taking into consideration factors which affect the system spectral sensitivity, such as light source spectral distribution properties, CCD spectral sensitivity properties, and so forth, a configuration may be made wherein, in addition to a light reducing filter being vapor-deposited or adhered to the R2 filter 14r2 and G2 filter 14g2 of the rotating filter 14 as described above, a first modification of the light source device 4 as shown in FIG. 21 may comprise a light reducing rotating filter 61 provided all the optical path, separate from the rotating filter 14. As shown in FIG. 22, this light reducing rotating filter 61 has the same double structure as the rotating filter 14 (see FIG. 2) and, with the portions corresponding to the R1 filter 14r1, G1 filter 14g1, B1 filter 14b1, and B2 filter 14b2 of the rotating filter 14 being transmitting portions, and comprising light reducing filters 62 and 63 for reducing the light of the bandwidth portions corresponding only to the R2 filter 14r2 and G2 filter 14g2, respectively. The light reducing rotating filter 61 is rotationally driven by a rotating filter motor 64 based on control signals of the control circuit 17 in the same way as the rotating filter 14, and also is capable of motion perpendicular to the optical path in the radial direction thereof by a mode switch-over motor 65 based on control signals from the mode switch-over circuit 42, and the driving timing thereof is carried out synchronously with the rotating filter 14.

Also, as a method for controlling not only bandwidth properties but also peak transmissivity properties, taking into consideration factors which affect the system spectral sensitivity, such as light source spectral distribution properties, CCD spectral sensitivity properties, and so forth, a second modification of the light source device 4 comprises a light reducing filter 71, instead of the light source device comprising the light reducing rotating filter 61 as described above. The light reducing filter 71 has desired bandwidth transmissivity by combination of multiple filters and is insertable to and extractable from the optical path by a filter driving motor 72 based on control signals from the mode switch-over circuit 42, the driving thereof being extracted at the time of the first filter of the rotating filter 14, and inserted at the time of the second filter, as shown in FIG. 23. This light reducing filter 71 is capable of controlling not only bandwidth properties but also peak transmissivity properties, by having light reducing properties such as shown in FIG. 26, by combining, for example, a first light reducing filter having light reducing properties shown in FIG. 24 and a second light reducing filter having light reducing properties shown in FIG. 25.

Now, as for an example of specific spectral properties of the above-described R2 filter 14r2, G2 filter 14g2, and B2 filter 14b2, as shown in FIG. 27, the R2 filter 14r2 has band-pass properties including 600 nm for the wavelength bandwidth and 20 to 40 nm for a full width at half maximum, the G2 filter 14*g*2 has band-pass properties including 540 nm for the wavelength bandwidth and 20 to 40 nm for a full width at half maximum, and further the B2 filter 14*b*2 has band-pass, properties including 420 nm for the wavelength bandwidth and 20 to 40 nm for a full width at half maximum.

With the spectral properties such as shown in FIG. 27, the capillary structure on the mucous membrane surface can be reproduced in high contrast by making the observation with an illumination light having narrow-band properties including 420 nm which is the band at which absorption of blood by visible light is great, and further, the distribution in the depth direction of the absorbents within the body mucous membrane can be reproduced with a different color, so the relative position of the absorbents other than the blood vessel images and the like in the depth direction can be conceptualized.

Also, as a modification made on the above-described R2 filter 14*r*2, G2 filter 14*g*2, and B2 filter 14*b*2, the G' filter 14*g*', G" filter 14*g*", and B2 filter 14*b*2 shown in FIG. 28 may be used, wherein the G' filter 14*g*' has band-pass properties including 550 nm for the wavelength bandwidth and 20 to 40 nm for a full width at half maximum, the G" filter 14*g*" has band-pass properties including 500 nm for the wavelength bandwidth and 20 to 40 nm for a full width at half maximum, and further the B2 filter 14*b*2 has band-pass properties including 420 nm for the wavelength bandwidth and 20 to 40 nm for a full width at half maximum.

With the spectral properties such as shown in FIG. 28, the capillary structure on the mucous membrane surface can be reproduced in high contrast by making the observation with an illumination light having narrow-band properties including 420 nm which is the band at which absorption of blood by visible light is great, and further, providing band-pass light around 500 nm which is the neighboring bandwidth can realize image reproduction specialized for the structure of the mucous membrane surface.

Also, the aperture level value corresponding to the light quantity setting value Lx is changed from Mx1 to Mx2 as shown in FIG. 9, being interlocked with the change from the first filter set to the second filter set, and consequently, the diaphragm is controlled in the direction of being opened, acting to compensate for reduction in the illumination light quantity by the filter which narrows the band, but the exposure time may be extended to increase the irradiated light quantity.

However, the organism which is the subject is not necessarily stationary, and does have peristalsis and pulse, so performing freezing operations while observing the image means that the image moves while exposing the CCD, and increases in the irradiated light quantity by extending this exposure time, and thus creates problems in that shaking of the image increases.

Accordingly, as a modification of the video processor 7, memories 180, 181, and 182 for pre-freezing, for constantly recording several frames of images, are provided after the synchronizing memories 27, 28, and 29, and a motion detecting circuit 190 for detecting motion by comparing image data between fields by the output signals of the synchronizing memories 27, 28, and 29, and the input signals of the selector 26, is provided, as shown in FIG. 29.

Due to such a configuration, pressing the mode switch-over switch 41 provided on the electronic endoscope 3 controls the rotation of the rotating filter 14 so that the mode switch-over circuit 42 controls the timing generator 35 such that the exposure time is made to be twice that of normal observation time by the control circuit 17 of the light source device 4 (the rotating speed for the second filter set of the rotating filter 14 is made to be a half of the rotating speed of the first filter set).

Also, in the event that a freeze switch 185 provided in the electronic endoscope 3 is pressed, image data is compared between fields by a motion detecting circuit 190 so as to detect motion, at the timing shown in FIG. 30 at the time of normal observation, and at the timing shown in FIG. 31 at the time of narrow-band observation, thereby controlling updating of the image data to be recorded in the memories 180, 181, and 182.

Specifically, taking a normal observation time shown in FIG. 30 as an example for description, image data R0 of one field period stored in the synchronizing memory 27 is compared with image data G0 input from the selector 26 by the motion detecting circuit 190 (the first comparison), and further image data G0 of one field period stored in the synchronizing memory 28 is compared with image data B0 input from the selector 26 (the second comparison), and in the event that judgment is made that there are no movements between either, the mode switch-over circuit 42 controls the timing generator 35, and then in the next field period (the period denoted by an asterisk in the figure), the image data R0, G0, and B0, stored in the synchronizing memories 27, 28, and 29, is written to the memories 180, 181, and 182.

Also, following judgment that there is no motion as the result of the above second comparison by the motion detecting circuit 190, image data B0 of one field period stored in the synchronizing memory 29 is compared with image data R1 input from the selector 26 (the third comparison), and in the event that judgment is made that there is no movement as the results of the third comparison as well, the mode switch-over circuit 42 controls the timing generator 35, and then in the next field period (the period denoted by a star in the figure), the image data R1, G0, and B0, stored in the synchronizing memories 27, 28, and 29, is overwritten on the memories 180, 181, and 182.

Also, in the event that judgment is made there is movement as the result of the third comparison, there is no updating in the above-described period denoted by a star, and the data recorded in the above period is kept in the memories 180, 181, and 182.

Thus, updating of the memories 180, 181, and 182 is sequentially performed at the subsequent field. Also, the same updating is performed for the memories 180, 181, and 182, with narrow-band observation as well, except that the exposure time is doubled, as shown in FIG. 31.

Upon the freeze switch 185 provided in the electronic endoscope 3 being pressed, the mode switch-over circuit 42 controls the timing generator 35 to stop the reading out from the synchronizing memories 27, 28, and 29, and the image data read out from the memories 180, 181, and 182 is output to the image processing circuit 30.

However, in the event that there is no image data in the memories 180, 181, and 182, or immediately following the mode switch-over switch 41 being pressed and switching over having been made to the second filter set of the rotating filter 14, the reading out from the synchronizing memories 27, 28, and 29, continues even if the freeze switch 185 is pressed, until motion is detected by the motion detecting circuit 190, and reading out from the synchronizing memories 27, 28, and 29, is stopped for the first time upon motion being detected.

Providing the memories 180, 181, and 182 and the motion detecting circuit 190 as shown in FIG. 29 allows images wherein shaking is suppressed to a minimum to be obtained even in the event of freezing in a state that the exposure time has been extended for narrow-band observation.

Now, generally, florescent images of living body tissue from excitation light do not reflect the fine structure of the surface of mucous membranes, but do bring to light disorders which are not readily discovered with visible light. On the other hand, the fine structures of the surface of the mucous membranes, such as capillary structure images, and so forth, are known to be crucial information for differential diagnosis of disorders. Accordingly, an arrangement may be made wherein these two types of information are combined and displayed as an image, thereby improving diagnostic capabilities.

Specifically, a second filter set of the rotating filter is configured of an excitation light F filter 14*f*, and G2 filter 14*g*2 and B2 filter 14*b*2, as shown in FIG. 32, instead of the R2 filter 14*r*2, G2 filter 14*g*2, and B2 filter 14*b*2. Now, the spectral properties with the excitation light F filter 14*f* are properties such as shown in FIG. 33.

Upon irradiating narrow-band excitation light from the F filter 14*f* onto the living body tissue, fluorescent light with the wavelength such as shown in FIG. 33 is emitted from the living body tissue. Accordingly, with the above-described embodiment, normal observation giving weight to color reproduction properties has wide band properties, and highly functional observation by fluorescent light and narrow-band light superimposed, can be switched between and applied.

In this way, observation of disorders which cannot be readily discovered with visible light by florescent light observation, and detailed observation of the surface of mucous membranes by narrow-band light can be performed, thereby improving diagnostic capabilities.

Next, a second embodiment of the present invention will be described with reference to FIG. 34 through FIG. 36.

Figure 34:
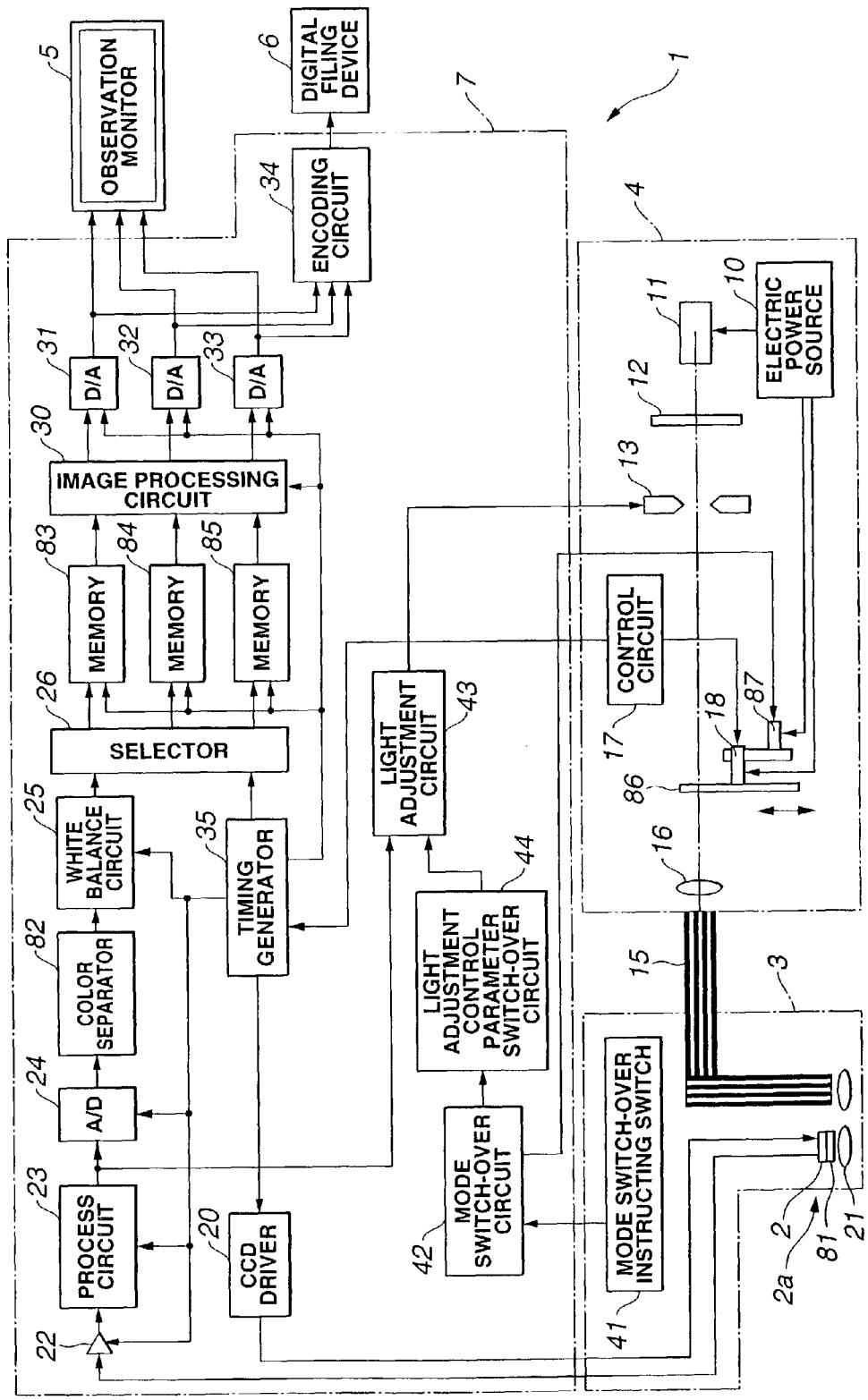
FIG. 34 is a configuration diagram illustrating the configuration of an endoscope device according to a second embodiment of the present invention.
Figure 35:
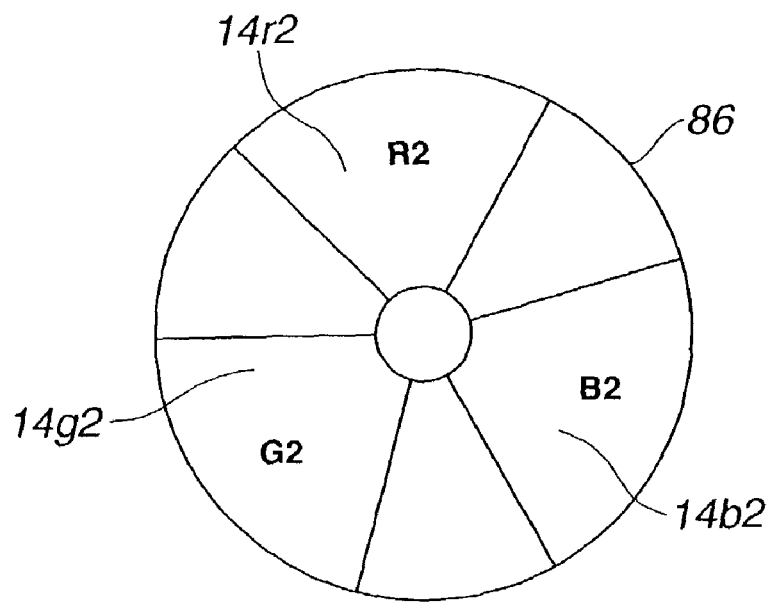
FIG. 35 is a configuration diagram illustrating the configuration of the rotating filter shown in FIG. 34.
Figure 36:
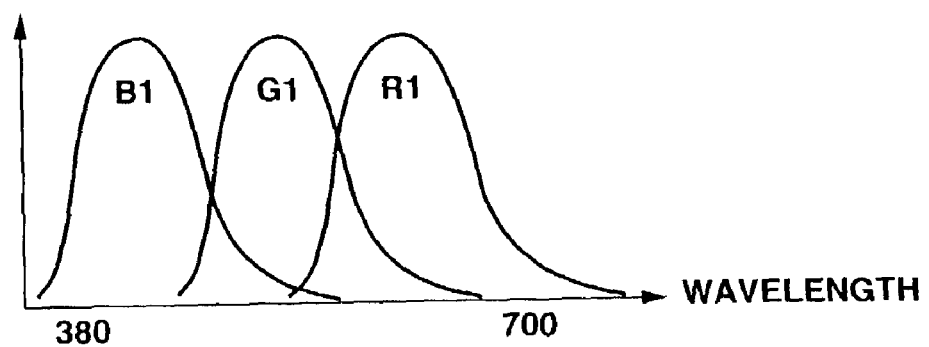
FIG. 36 is a diagram illustrating the spectral properties of the color chip shown in FIG. 34.

FIG. 34 is a configuration diagram illustrating the configuration of an endoscope device, FIG. 35 is a configuration diagram illustrating the configuration of the rotating filter shown in FIG. 34, and FIG. 36 is a diagram illustrating the spectral properties of the color chip shown in FIG. 34.

The second embodiment is almost the same as the first embodiment, so only the differing points will be described, and the same configurations will be denoted with the same reference numerals and description thereof will be omitted.

As shown in FIG. 34, with the electronic endoscope 3 according to the present embodiment, a color chip 81 is disposed on the front face of the CCD 2, thereby making up a color CCD 2*a*, configuring an endoscope device 1 of a synchronous system when performing normal observation. Color image signals from the color CCD 2*a* are converted into color image data at the A/D converter 24, subsequently subjected to color separation at a color separating circuit 82, then input to the white balance circuit 25, and stored in memories 83, 84, and 85, via the selector 26, subsequently subjected to interpolation processing or the like at the image processing circuit 30, following which desired image processing is performed.

As shown in FIG. 35, the rotating filter 86 of the light source device 4 is made up of an R2 filter 14*r*2, G2 filter 14*g*2, and B2 filter 14*b*2, having spectral properties which are the same as that of the second filter set in the first embodiment, rotationally driven by the rotating filter motor 18 based on control signals from the control circuit 17, and being insertable to and extractable from the optical path by a filter driving motor 87 based on control signals from the mode switch-over circuit 42 which has received instruction signals from the mode switch-over switch 41 provided in the electronic endoscope 3.

With the present embodiment thus configured, a rotating filter 86 is extracted from the optical path at normal observation time, so that white light is irradiated on the living body tissue. The living body tissue image of the white light is captured by the color CCD 2*a*. The spectral properties of the color chip 81 on the front face of the CCD 2*a* at this time are shown in FIG. 36.

On the other hand, when making narrow-band like observation, the rotating filter 86 is inserted into the optical path, with frame sequence light from the R2 filter 14*r*2, G2 filter 14*g*2, and B2 filter 14*b*2, irradiated to the living body tissue. A living body tissue image of this frame sequence light is taken by the color CCD 2*a*.

Accordingly, frame sequence light having discrete narrow-band spectral properties from the R2 filter 14*r*2, G2 filter 14*g*2, and B2 filter 14*b*2, is irradiated on to the body organism at the time of narrow-band observation, so the same advantages as those of the first embodiment can be obtained with the present embodiment, as well.

Next, a third embodiment of the present invention will be described with reference to FIG. 37 through FIG. 46.

Figure 37:
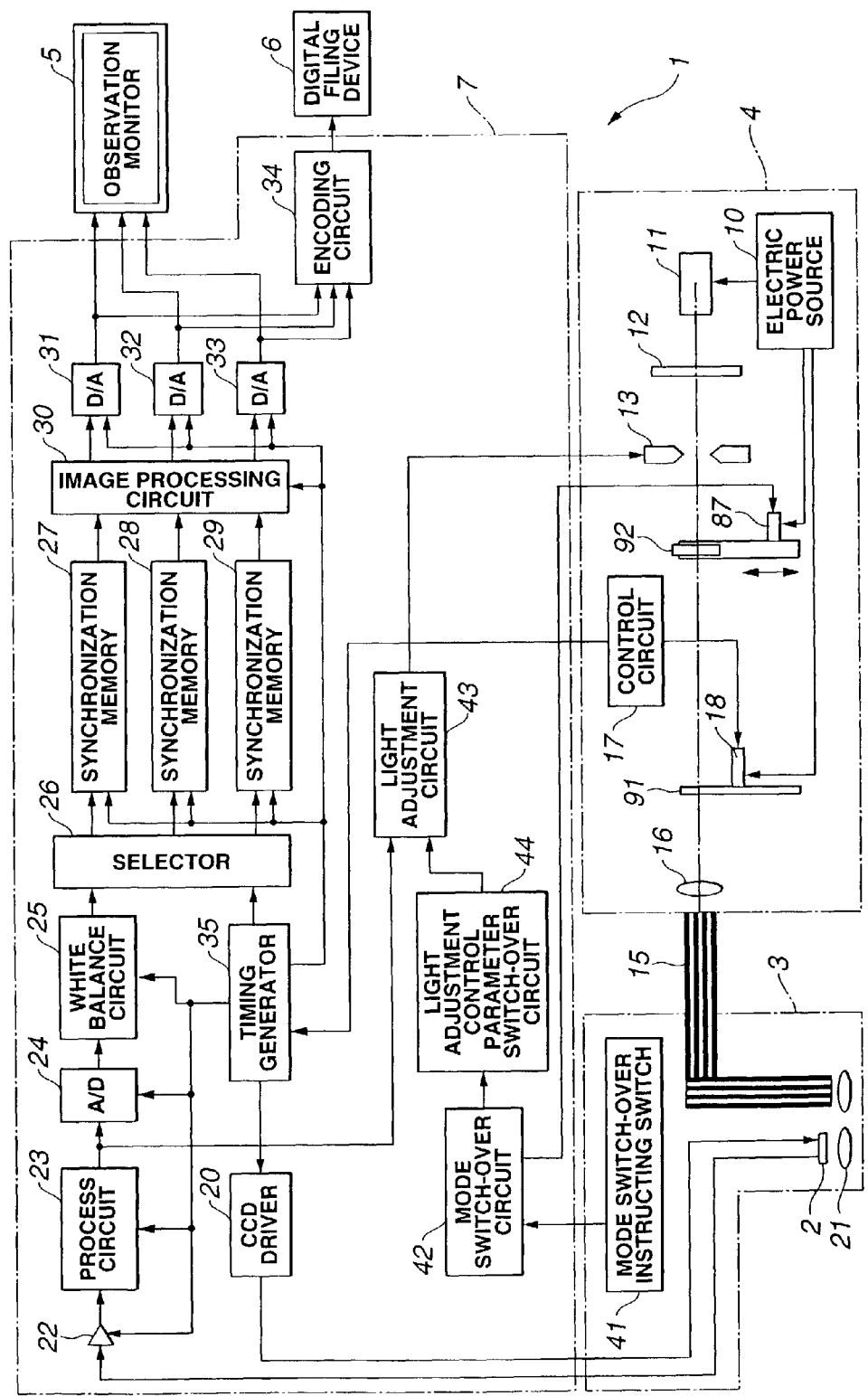
FIG. 37 is a configuration diagram illustrating the configuration of an endoscope device according to a third embodiment of the present invention.
Figure 38:
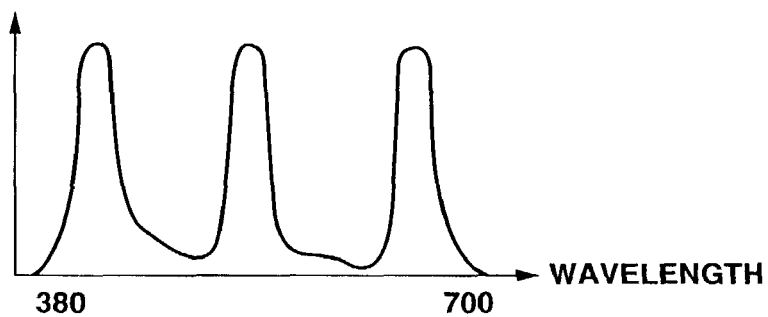
FIG. 38 is a diagram illustrating the band-pass properties of the band restricting filter shown in FIG. 37.
Figure 39:
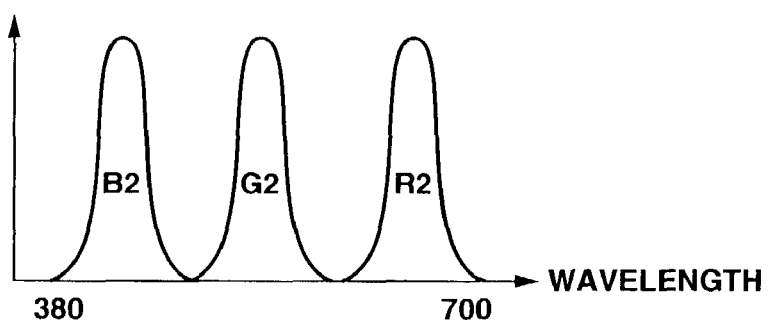
FIG. 39 is a diagram illustrating the spectral properties of discrete narrow-band frame sequence light obtained by the band restricting filter shown in FIG. 38.
Figure 40:
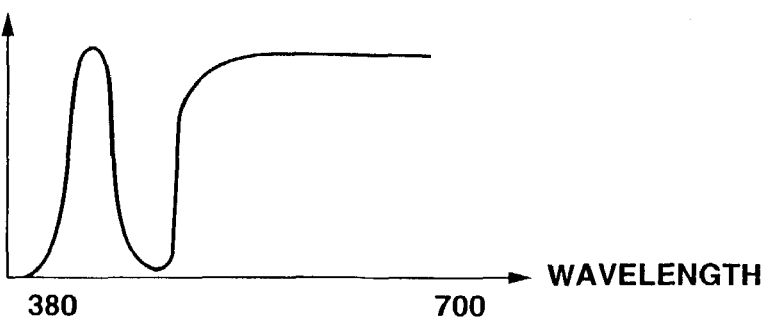
FIG. 40 is a diagram illustrating the band-pass properties of a first modification made on the band restricting filter shown in FIG. 37.
Figure 41:
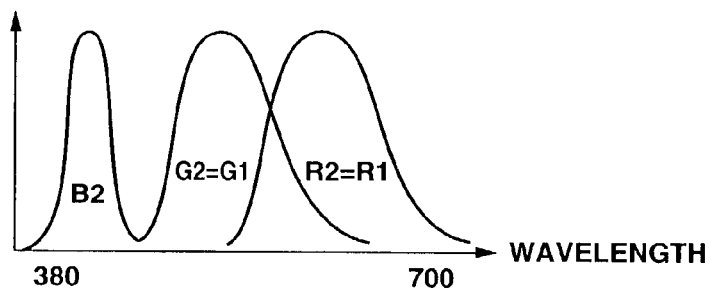
FIG. 41 is a diagram illustrating the spectral properties of discrete narrow-band frame sequence light from the band restricting filter shown in FIG. 40.
Figure 42:
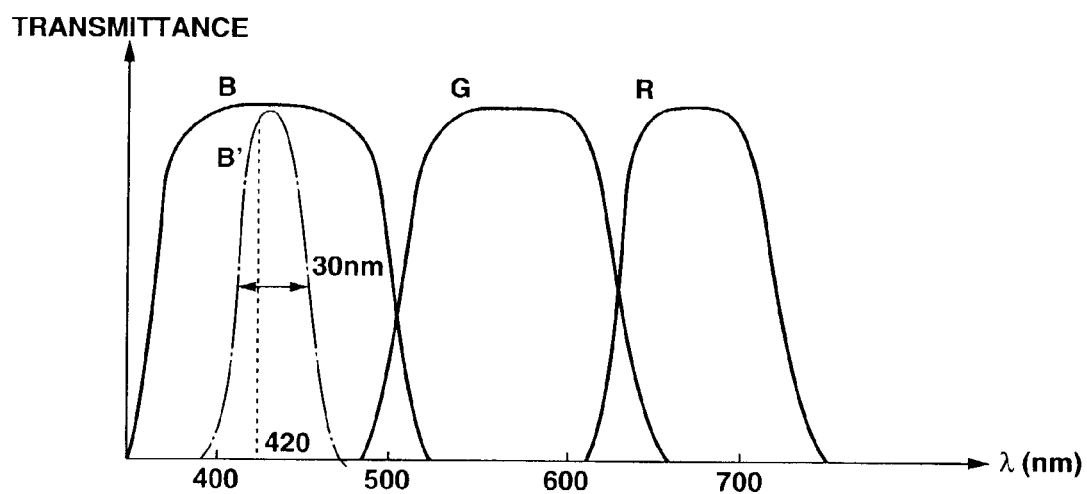
FIG. 42 is a diagram illustrating the band-pass properties of a second modification made on the band restricting filter shown in FIG. 37.
Figure 43:
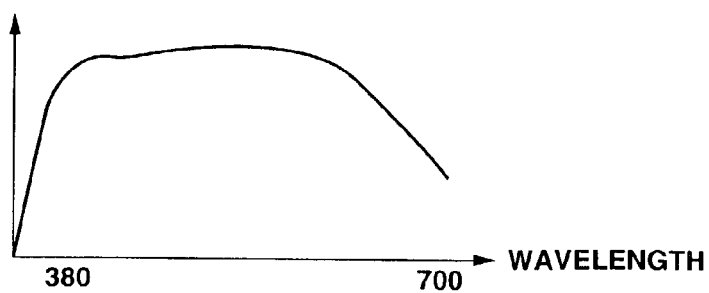
FIG. 43 is a diagram illustrating an example of spectral properties of the xenon lamp shown in FIG. 37.
Figure 44:
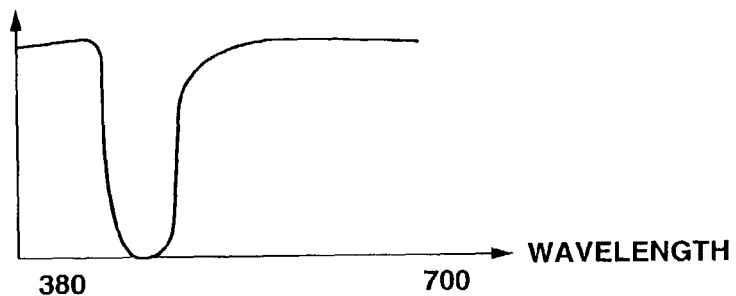
FIG. 44 is a diagram illustrating the band-pass properties of a third modification made on the band restricting filter shown in FIG. 37, in the event that the spectral properties of the xenon lamp are those shown in FIG. 43.
Figure 46:
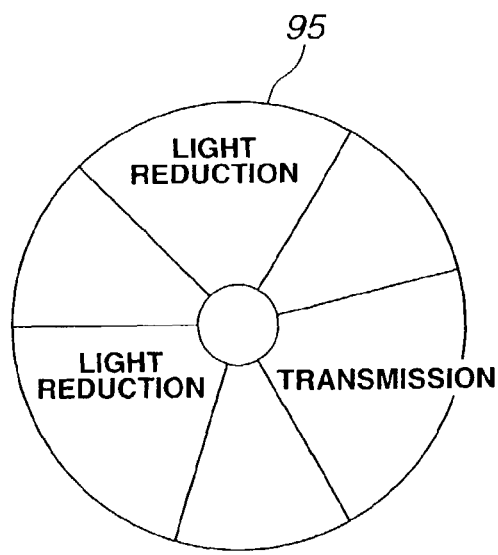
FIG. 46 is a diagram illustrating the configuration of the light reduction rotating filter shown in FIG. 45.
Figure 45:
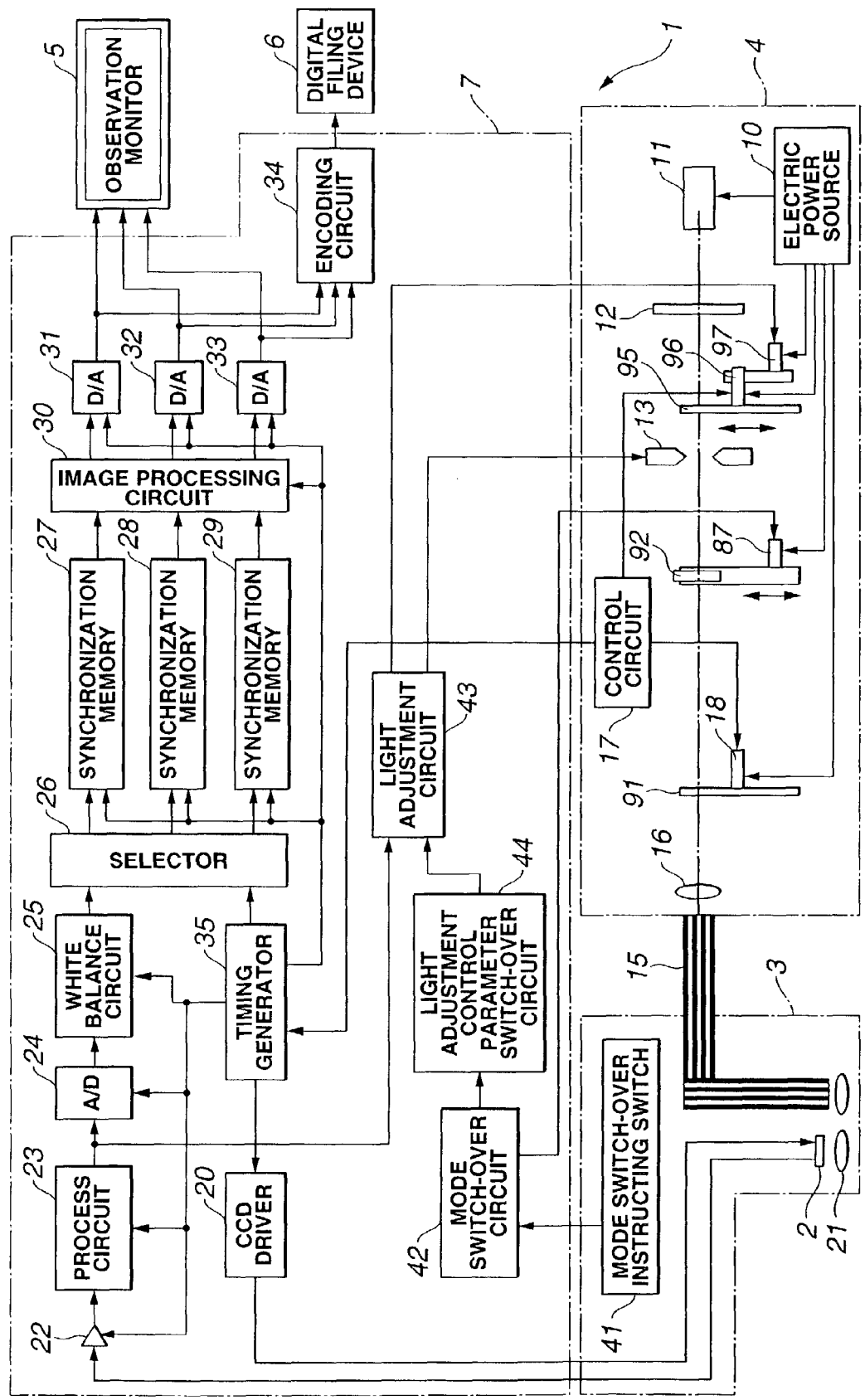
FIG. 45 is a configuration diagram illustrating the configuration of a modification made on the light source device shown in FIG. 37.

FIG. 37 is a configuration diagram illustrating the configuration of an endoscope device, FIG. 38 is a diagram illustrating the band-pass properties of the band restricting filter shown in FIG. 37, FIG. 39 is a diagram illustrating the spectral properties of discrete narrow-band frame sequence light obtained by the band restricting filter shown in FIG. 38, FIG. 40 is a diagram illustrating the band-pass properties of a first modification made on the band restricting filter shown in FIG. 37, FIG. 41 is a diagram illustrating the spectral properties of discrete narrow-band frame sequence light from the band restricting filter shown in FIG. 40, FIG. 42 is a diagram illustrating the band-pass properties of a second modification made on the band restricting filter shown in FIG. 37, FIG. 43 is a diagram illustrating an example of spectral properties of the xenon lamp shown in FIG. 37, FIG. 44 is a diagram illustrating the band-pass properties of a third modification made on the band restricting filter shown in FIG. 37, in the event that the spectral properties of the xenon lamp are those shown in FIG. 43, FIG. 45 is a configuration diagram illustrating the configuration of a modification made on the light source device shown in FIG. 37, and FIG. 46 is a diagram illustrating the configuration of the light reduction rotating filter shown in FIG. 45.

The third embodiment is almost the same as the first embodiment, so only the differing points will be described, and the same configurations will be denoted with the same reference numerals and description thereof will be omitted.

As shown in FIG. 37, the light source device 4 according to the present embodiment comprises a rotating filter 91 upon which are disposed an R1 filter 14*ri*, G1 filter 14*g*1, and B1 filter 14*b*1, and a bandwidth redistricting filter 92 having multi-peak band-pass properties (R2 band, G2 band, and B2 band), as shown in FIG. 38, for restricting the bandwidth of transmitted light, where the rotating filter 91 is rotationally driven by the rotating filter motor 18 based on control signals from the control circuit 17, and the bandwidth restricting filter 92 is insertable to and extractable from the optical path by a filter driving motor 87 based on control signals from the mode switch-over circuit 42 which has received the instruction signals from the mode switch-over switch 41.

With the present embodiment thus configured, the bandwidth restricting filter 92 is inserted into the optical path, whereby the frame sequence light transmitting the rotating filter 91 becomes discrete narrow-band frame sequence light as shown in FIG. 39, and this narrow-band frame sequence light is irradiated on the living body tissue, so the same advantages as those of the first embodiment can be obtained with the present embodiment, as well.

Now, with the present embodiment, the bandwidth restricting filter 92 is configured to have narrow-band properties at the three bands of RGB as shown in FIG. 38, but the embodiment is not restricted to this, and in the event that improvement in only the observation capabilities of the body surface structures is desired, there is no need to make all three bands narrow bandwidth, rather, only the B band needs to be narrow, so a bandwidth restricting filter having irregular multi-peak band-pass properties may be used as shown in FIG. 40, and combining such a bandwidth restricting filter with the RGB rotating filter 91 allows frame sequence light having narrow-band properties for the B band alone to be irradiated onto the living body tissue, as shown in FIG. 41.

In order to provide the narrow-band properties for the B band alone, the bandwidth restricting filter 92 may be made to be a bandwidth restricting filter wherein the RGB light is made to be light of B' alone, as shown in FIG. 42, with the specific example of narrow-band properties of this B' alone being band-pass properties including 420 nm for the wavelength bandwidth and 20 to 40 nm for a full width at half maximum.

With the spectral properties such as shown in FIG. 42, the capillary structure on the mucous membrane surface can be reproduced in high contrast by making the observation with an illumination light having narrow-band properties including 420 nm which is the band at which absorption of blood by visible light is great.

Also, in the event that the shielding properties of the short wavelength region side of the rotating filter 91 can be used, such as in cases wherein the spectral properties of the xenon lamp have properties of attenuation in the short wavelength region, as shown in FIG. 43, a bandwidth restriction filter having open properties instead of having band-pass properties at the short wavelength side may be used, as shown in FIG. 44.

Also, taking into consideration the fact that energy for the lamp drops in the short wavelength region, and further that the CCD spectral sensitivity properties lose sensitivity in this region, the gain of the B2 band image is excessively increased as a result of color adjustments processing such as white balance and the like, thereby yielding an image with a very great amount of noise.

Accordingly, as a modification of the light source device, the light quantity for each band is adjusted at the light source side so that each band image has appropriate SN properties even after performing white balance taking into consideration the spectral properties other than those of the filter, such as of the lamp, CCD, etc., by inserting the light reducing rotating filter 95 into the optical path, as shown in FIG. 45.

That is, as shown in FIG. 46, each part of the light reducing rotating filter 95 corresponding to the B1 filter 14b1 of the rotating filter 91 is configured as a transmitting portion, and the parts corresponding to the R1 filter 14r1 and the G1 filter 14g1 are configured as light reducing filters for reducing the light of the corresponding bandwidths. The light reducing rotating filter 95 is rotationally driven by a rotating filter motor 96 based on control signals from the control circuit 17 in the same way as the rotating filter 91, and also is capable of moving perpendicularly to the optical path in the radial direction thereof by a mode switch-over motor 97 based on controls signals from the mode switch-over circuit 42, and the driving timing thereof is carried out synchronously with that of the rotating filter 91.

Next, a fourth embodiment of the present invention will be described with reference to FIG. 47 to FIG. 50.

Figure 48:
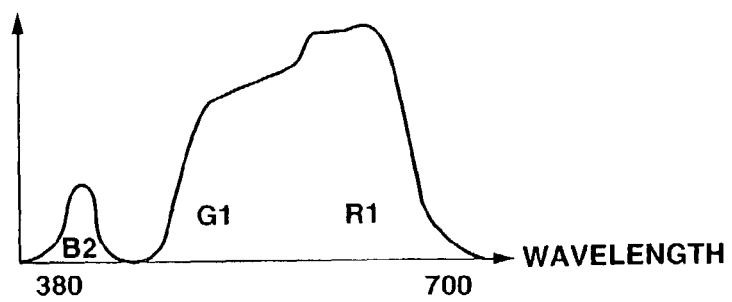
FIG. 48 is a diagram illustrating an example of spectral distribution of light irradiated from the light source device shown in FIG. 47 at the time of normal observation.
Figure 47:
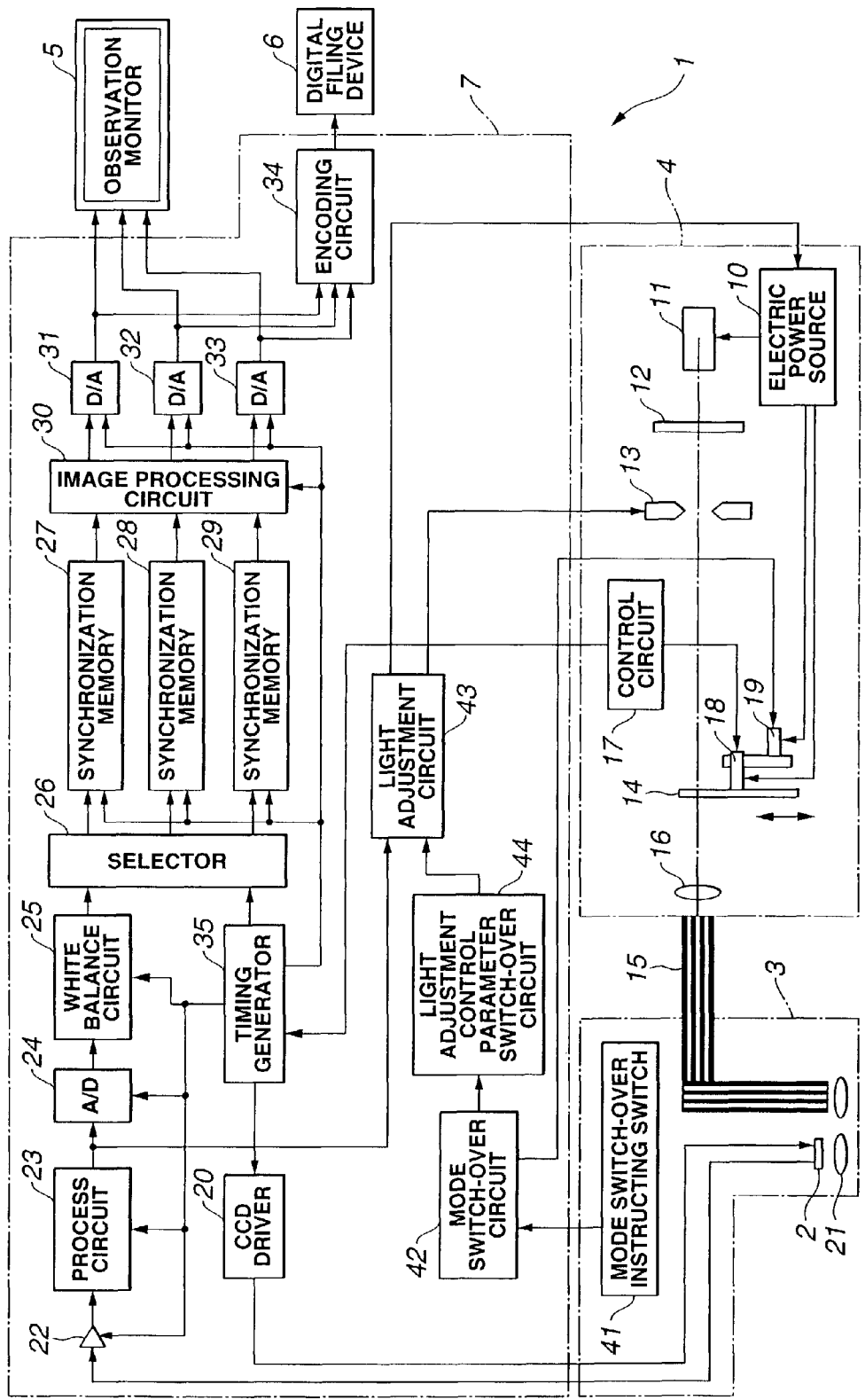
FIG. 47 is a configuration diagram illustrating the configuration of an endoscope device according to a fourth embodiment of the present invention.
Figure 50:
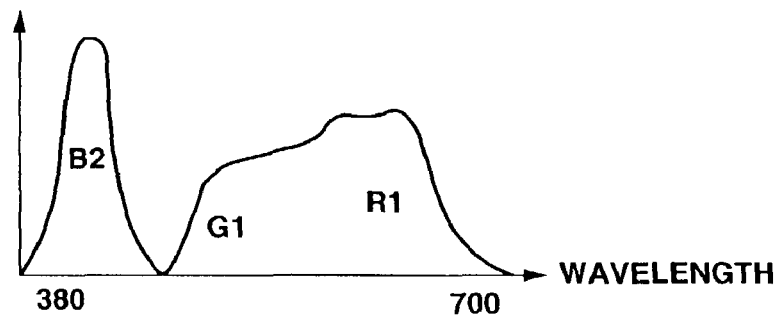
FIG. 50 is a diagram illustrating an example of the spectral distribution of light irradiated from the light source device by the electric power supply unit shown in FIG. 47, at the time of narrow-band observation.

FIG. 47 is a configuration diagram illustrating the configuration of an endoscope device, FIG. 48 is a diagram illustrating an example of spectral distribution of light irradiated from the light source device shown in FIG. 47 at the time of normal observation, FIG. 49 is a diagram illustrating the illumination timing of each band by the electric power supply unit shown in FIG. 47, and the light quantity control timing at that time, and FIG. 50 is a diagram illustrating an example of the spectral distribution of light irradiated from the light source device by the electric power supply unit shown in FIG. 47, at the time of narrow-band observation.

The fourth embodiment is almost the same as the third embodiment, so only the differing points will be described, and the same configurations will be denoted with the same reference numerals and description thereof will be omitted.

With the light source device according to the present embodiment, the electric power unit 10 is capable of receiving control signals from the light adjusting circuit 43 and changing the driving voltage of the xenon lamp 11.

Taking the lamp properties into consideration, the spectral distribution of the light irradiated from the actual light source device is as shown in FIG. 48. Taking into consideration the fact that the energy of the lamp drops at the short wavelength region, and further that the CCD spectral sensitivity properties lose sensitivity in this region, the gain of the B2 band image is excessively increased as a result of color adjustments processing such as white balance and the like, thereby yielding an image with a very great amount of noise.

Accordingly, with the present embodiment, the light quantity for each band is adjusted at the light source side so that each band image has appropriate SN properties even after performing white balance taking into consideration the spectral properties other than those of the filter, such as of the lamp, CCD, etc. Note that the bandwidth restricting filter 92 has the spectral properties shown in FIG. 44.

FIG. 49 illustrates the illumination timing for each band, and the light quantity control timing at that time. With normal observation wherein the bandwidth restricting filter 92 is not inserted into the optical path, the electric power supply unit 10 receives control signals from the light adjusting circuit 43 at an illumination timing indicated by a in FIG. 49 and controls the voltage level of the driving voltage of the xenon lamp 11, and performs light quantity control such as indicated by "b" in FIG. 49. The reason that the quantity of light is decreased during the shielding period is to alleviate the heat generated from the lamp.

On the other hand, on the narrow-band observation wherein the bandwidth restricting filter 92 is inserted in the optical path, the electric power supply unit 10 receives control signals from the light adjusting circuit 43 at an illumination timing indicated by "c" in FIG. 49 and controls the voltage level of the driving voltage of the xenon lamp 11, and performs light quantity control such as indicated by "d" in FIG. 49.

Thus, according to the present embodiment, in addition to the advantages of the third embodiment, the spectral distributions of light irradiated from the light source in the event that the voltage level of the driving voltage of the xenon lamp 11 is not controlled (see FIG. 48) become spectral properties such as shown in FIG. 50, so light quantity control wherein each band image has suitable SN properties can be realized.

Figure 51:
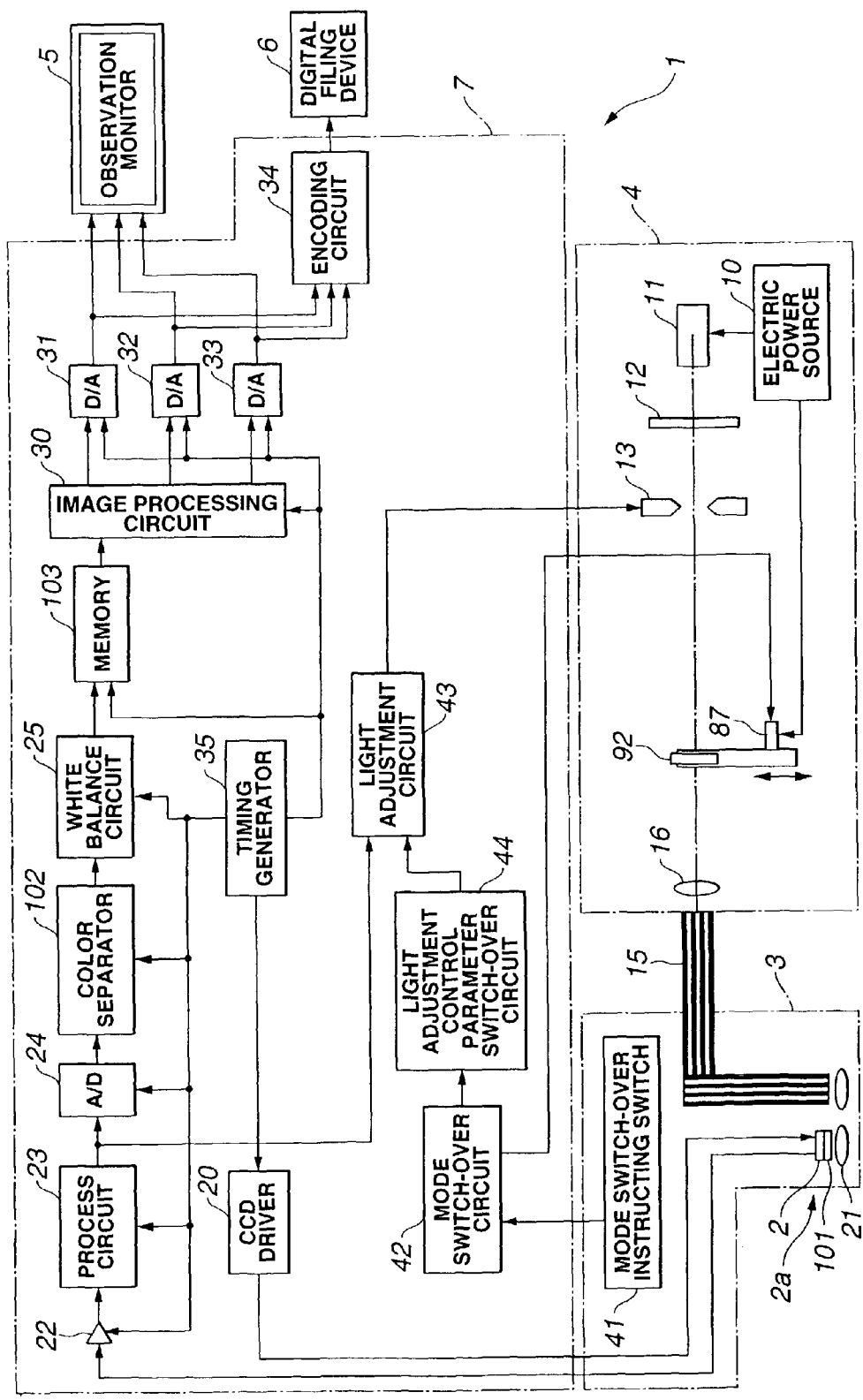
FIG. 51 is a configuration diagram illustrating the configuration of an endoscope device according to a fifth embodiment of the present invention.

FIG. 51 is a configuration diagram illustrating the configuration of an endoscope device according to a fifth embodiment of the present invention.

The fifth embodiment is almost the same as the third embodiment, so only the differing points will be described, and the same configurations will be denoted with the same reference numerals and description thereof will be omitted.

As shown in FIG. 51, with the electronic endoscope 3 according to the present embodiment, a color chip 101 is disposed at the front face of the CCD 2 to configure a color CCD 2a, thus configuring the synchronous system type endoscope device 1. Color image signals from the color CCD 2a are converted into color image data at the A/D converter 24, subsequently subjected to color separation at the color separating circuit 102, then input to the white balance circuit 25, and stored in a memory 103, via the selector 26, subsequently subjected to interpolation processing and the like at the image processing circuit 30, following which desired image processing is performed.

The light source device 4 comprises the bandwidth restricting filter 92 having multi-peak band-pass properties (see FIG. 38, FIG. 40, FIG. 44), and the bandwidth restricting filter 92 is arranged so as to be inserted to and extracted from the optical path by the filter moving motor 87, based on control signals from the mode switch-over circuit 42 which has received instructions signals from the mode switch-over switch 41.

With the present embodiment thus configured, the bandwidth restricting filter 92 is inserted into the optical path, whereby the spectral properties of the image taken by the CCD 2 via the color chip 101 become discrete narrow-band band images (see FIG. 39), and the narrow-band band images are subjected to image processing, so the same advantages as those of the third embodiment can be obtained with the present embodiment, as well.

Figure 52:
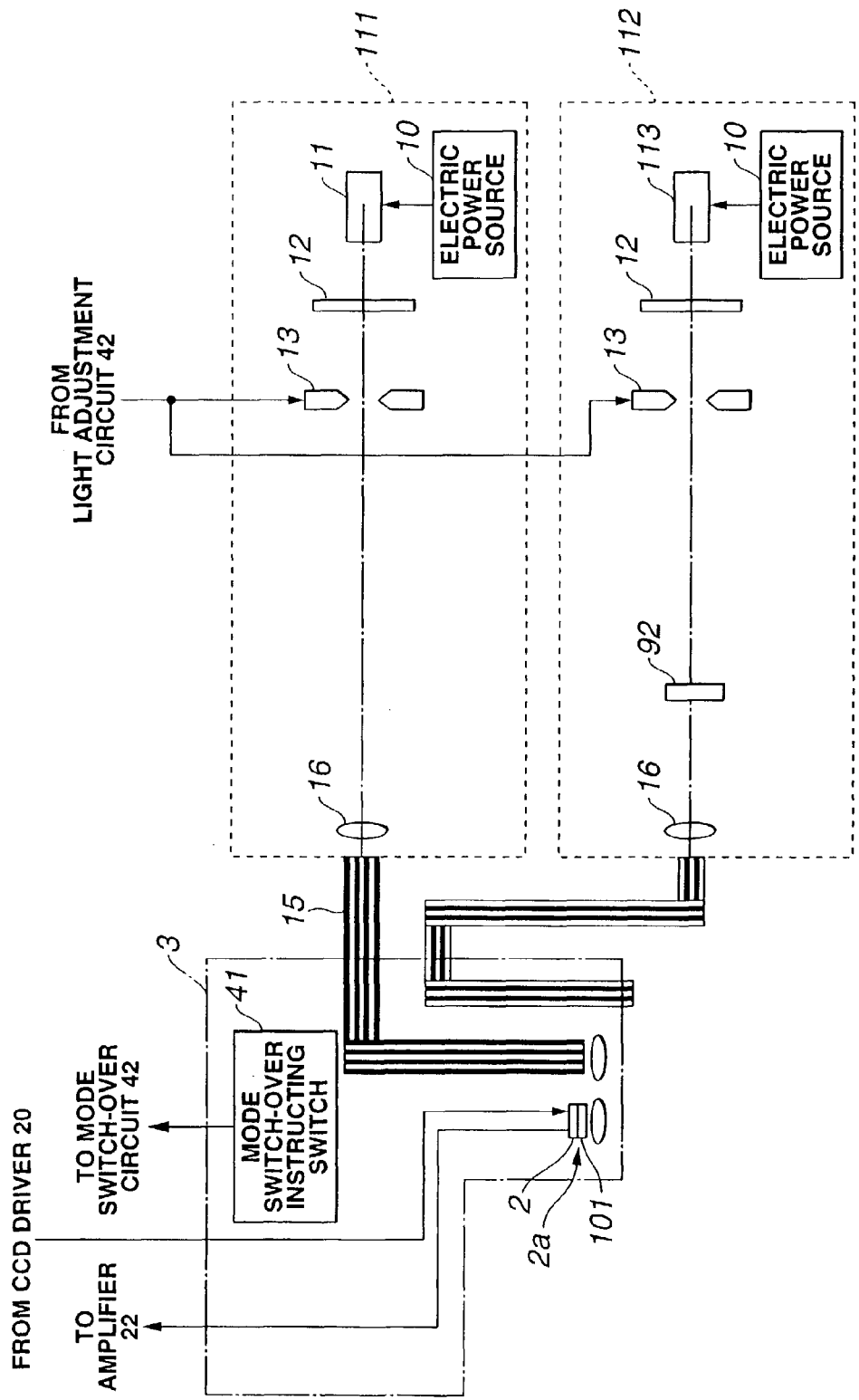
FIG. 52 is a configuration diagram illustrating the configuration of an endoscope device according to a sixth embodiment of the present invention.

FIG. 52 is a configuration diagram illustrating the configuration of an endoscope device according to a sixth embodiment of the present invention.

The sixth embodiment is almost the same as the fifth embodiment, so only the differing points will be described, and the same configurations will be denoted with the same reference numerals and description thereof will be omitted.

With the present embodiment, as shown in FIG. 52, a light source device 112 for narrow-band observation is provided separately from a light source device 111 for normal observation.

The light source device 111 has the xenon lamp 11 as illumination light emitting means, and the white light from the xenon lamp 11 passes through the diaphragm device 13 and is cast into the incident face of the light guide 15 of the electronic endoscope comprising the color CCD 2a.

Also, the light source device 112 has an extra-high pressure mercury lamp 113 as the illumination light emitting means, wherein the light from the extra-high pressure mercury lamp 113 is adjusted at the diaphragm device 13, and is cast into an incident face of an illumination probe 114, inserted into a treatment equipment channel (not shown) of the electronic endoscope 3, via the bandwidth restricting filter 92.

Now, the diaphragm device 13 for each of the light source devices 111 and 112 are arranged so as to be controlled by the light adjusting circuit 43 based on control signals from the mode switch-over circuit 42 and light adjustment control parameters from the light adjustment control parameter switch-over circuit 44.

With the present embodiment, at the time of normal observation, the diaphragm device 13 of the light source device 111 is set on the bright side, while the diaphragm device 13 of the light source device 112 is set on the dark side or is shielded.

Also, the time of narrow-band light observation, the diaphragm device 13 of the light source device 112 is set on the bright side, while the diaphragm device 13 of the light source device 111 is set on the dark side or is shielded.

Setting each of the diaphragm devices 13 thus means that narrow-band light is irradiated from the emitting face of the illumination probe 114 at the time of narrow-band light observation, so the same advantages as those of the fifth embodiment can be obtained with the present embodiment, as well.

Next, a seventh embodiment of the present invention will be described with reference to FIG. 53 to FIG. 57.

Figure 54:
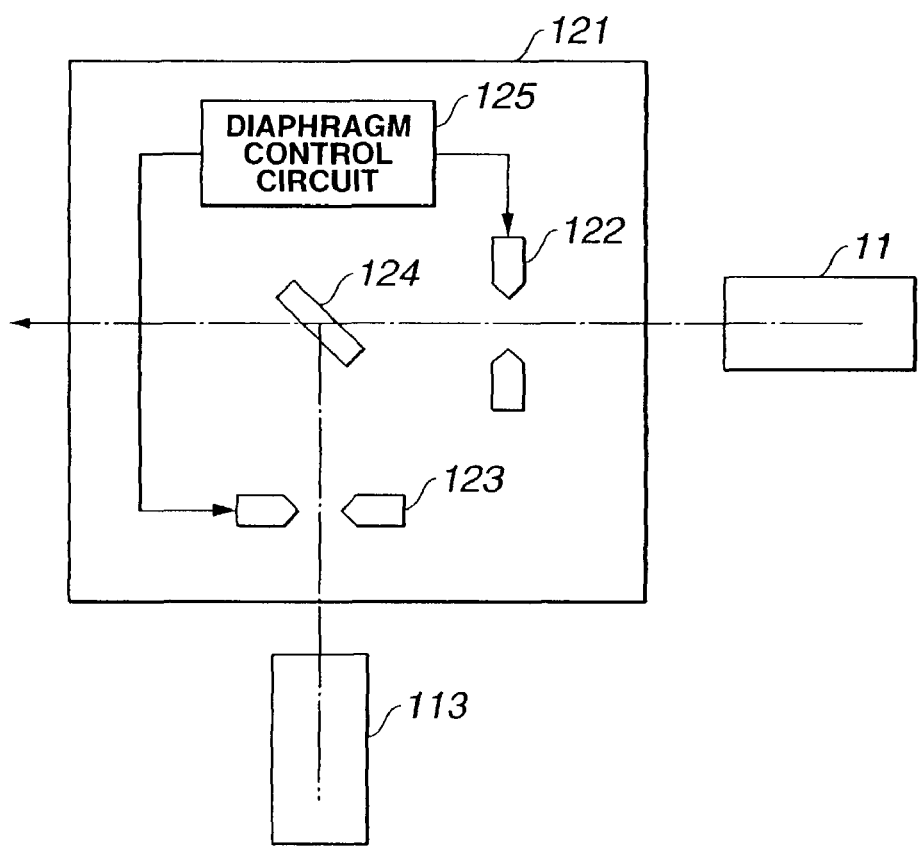
FIG. 54 is a diagram illustrating an example of spectral distribution of the xenon lamp shown in FIG. 53.
Figure 53:
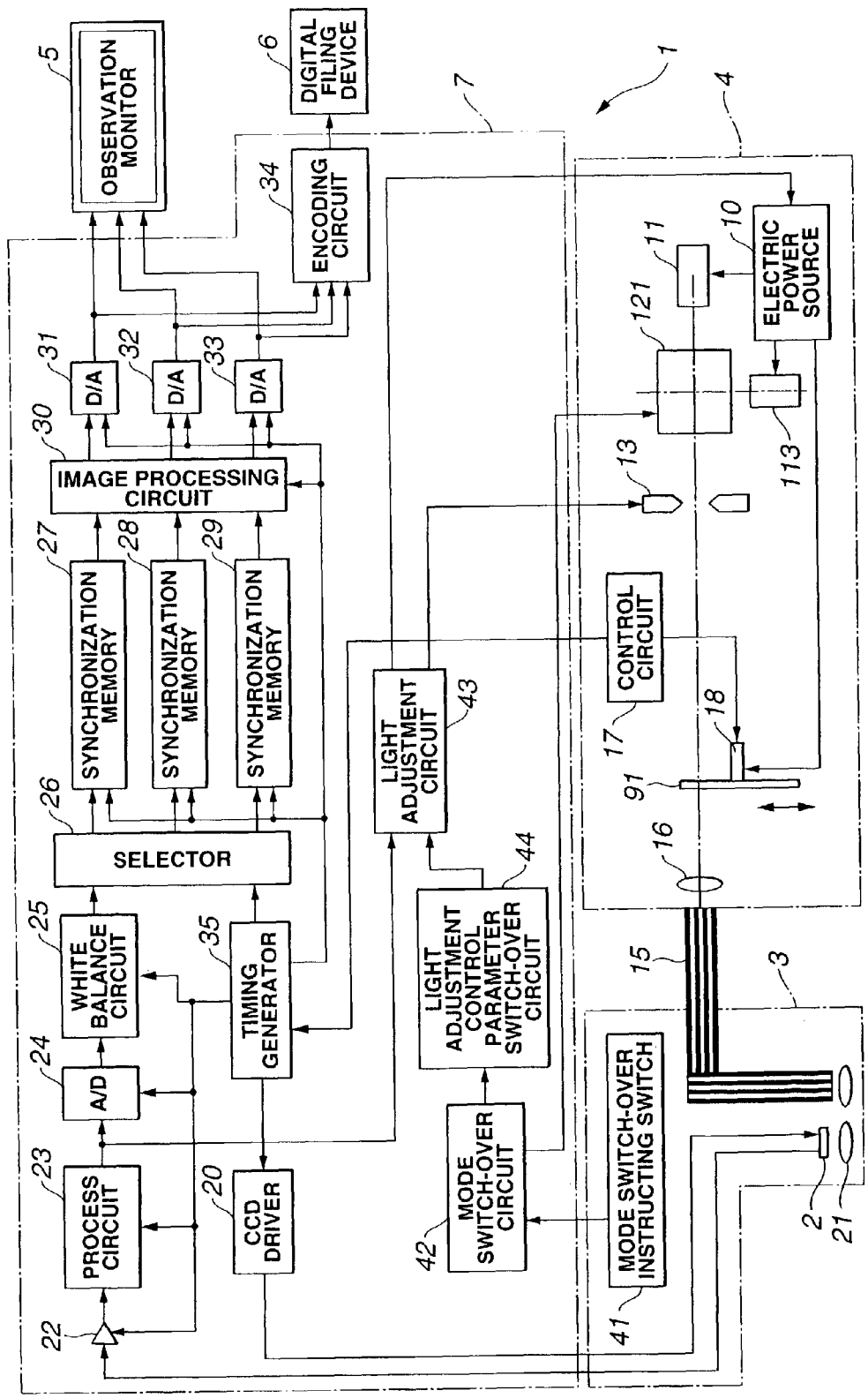
FIG. 53 is a configuration diagram illustrating the configuration of an endoscope device according to a seventh embodiment of the present invention.
Figure 55:
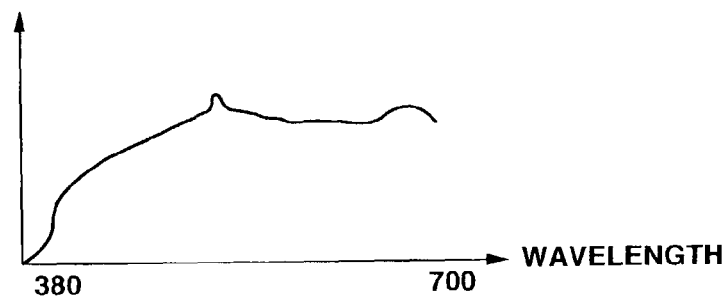
FIG. 55 is a diagram illustrating an example of spectral distribution of the extra-high pressure mercury lamp shown in FIG. 53.
Figure 56:
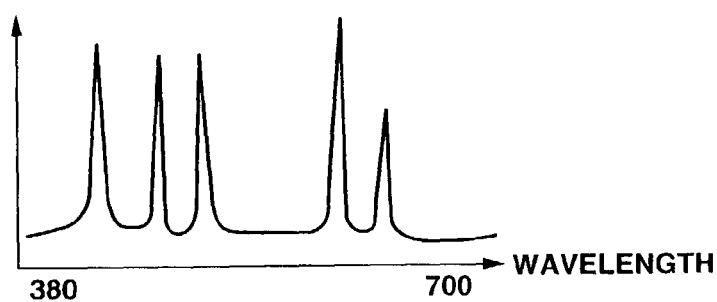
FIG. 56 is a configuration diagram illustrating the configuration of the light mixing unit shown in FIG. 53.
Figure 57:
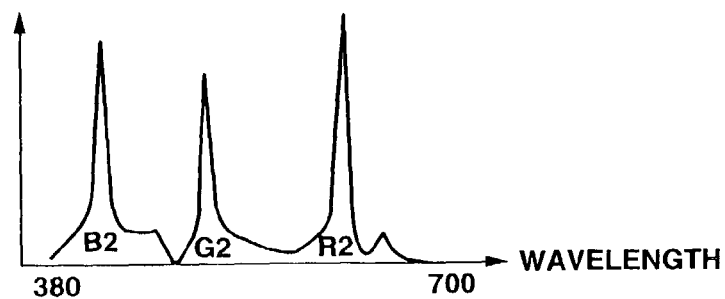
FIG. 57 is a diagram illustrating an example of spectral distribution of light irradiated from the light source device at the time of narrow-band observation performed by the light mixing unit shown in FIG. 56.

FIG. 53 is a configuration diagram illustrating the configuration of an endoscope device, FIG. 54 is a diagram illustrating an example of spectral distribution of the xenon lamp shown in FIG. 53, FIG. 55 is a diagram illustrating an example of spectral distribution of the extra-high pressure mercury lamp shown in FIG. 53, FIG. 56 is a configuration diagram illustrating the configuration of the light mixing unit shown in FIG. 53, and FIG. 57 is a diagram illustrating an example of spectral distribution of light irradiated from the light source device at the time of narrow-band observation with the light mixing unit shown in FIG. 56.

The seventh embodiment is almost the same as the third embodiment, so only the differing points will be described, and the same configurations will be denoted with the same reference numerals and description thereof will be omitted.

As shown in FIG. 53, the light source device 3 according to the present embodiment comprises the xenon lamp 11 having a relatively broad spectral distribution as shown in FIG. 54, and the extra-high pressure mercury lamp 113 with multiple emission line spectrums such as shown in FIG. 55 that is provided on the optical path, and further comprises a light mixing unit 121 for mixing the light from the xenon lamp 11 and the extra-high pressure mercury lamp 113. The light that is mixed at the light mixing unit 121 is supplied to the electronic endoscope via the diaphragm device 13 and rotating filter 91.

As shown in FIG. 56, the light mixing unit 121 comprises a diaphragm 122 for adjusting the light quantity of light from the xenon lamp 11, a diaphragm 123 for adjusting the light quantity of light from the extra-high pressure mercury lamp 113, a half mirror 124 for synthesizing the light coming through the diaphragm 122 and diaphragm 123, and outputting onto the optical path of the diaphragm device 13 and rotating filter 91, and a diaphragm control circuit 125 for controlling the diaphragm 122 and the diaphragm 123 based on control signals from the mode switch-over circuit 42.

When performing narrow-band observation, the diaphragm 122 at the front face of the xenon lamp 11 is closed by the diaphragm control circuit 125, and the diaphragm 123 at the front face of the extra-high pressure mercury lamp 113 is opened, so that the illumination light emitted from the light mixing unit has spectral properties equivalent to those of the extra-high pressure mercury lamp 113. This light is then transmitted through an R1G1B1 rotating filter 91, consequently irradiating RGB narrow-band frame sequence light such as shown in FIG. 57 into the living body tissue.

On the other hand, at the time of normal observation, the diaphragm 122 at the front face of the extra-high pressure mercury lamp 113 is closed by a diaphragm control circuit 125, and the diaphragm 123 at the front face of the xenon lamp 11 is opened, so that RGB frame sequence light with natural color reproduction is irradiated on the living body tissue.

According to such an embodiment, the same advantages as those of the third embodiment can be obtained.

Now, for obtaining intermediate illumination light between the xenon lamp and the extra-high pressure mercury lamp 113, adjusting the degree of opening of the diaphragms at the front face of both the lamps mixes both lamp properties at a percentage corresponding to the ratio of opening the diaphragms, thereby yielding illumination light having spectral properties differing from either of the lamps.

Also, the actions of the light adjusting circuit 43 are changed by the light adjustment control parameters changing the light adjusting table according to switching over of the mode, and the change in the spectral distribution of the illumination light compensates for the change in the quantity of illumination light. Consequently, images which are constantly of a suitable brightness can be observed even when switching over to illumination light spectral distributions suiting such an object as observing the surface structure of mucous membranes in detail.

Figure 58:
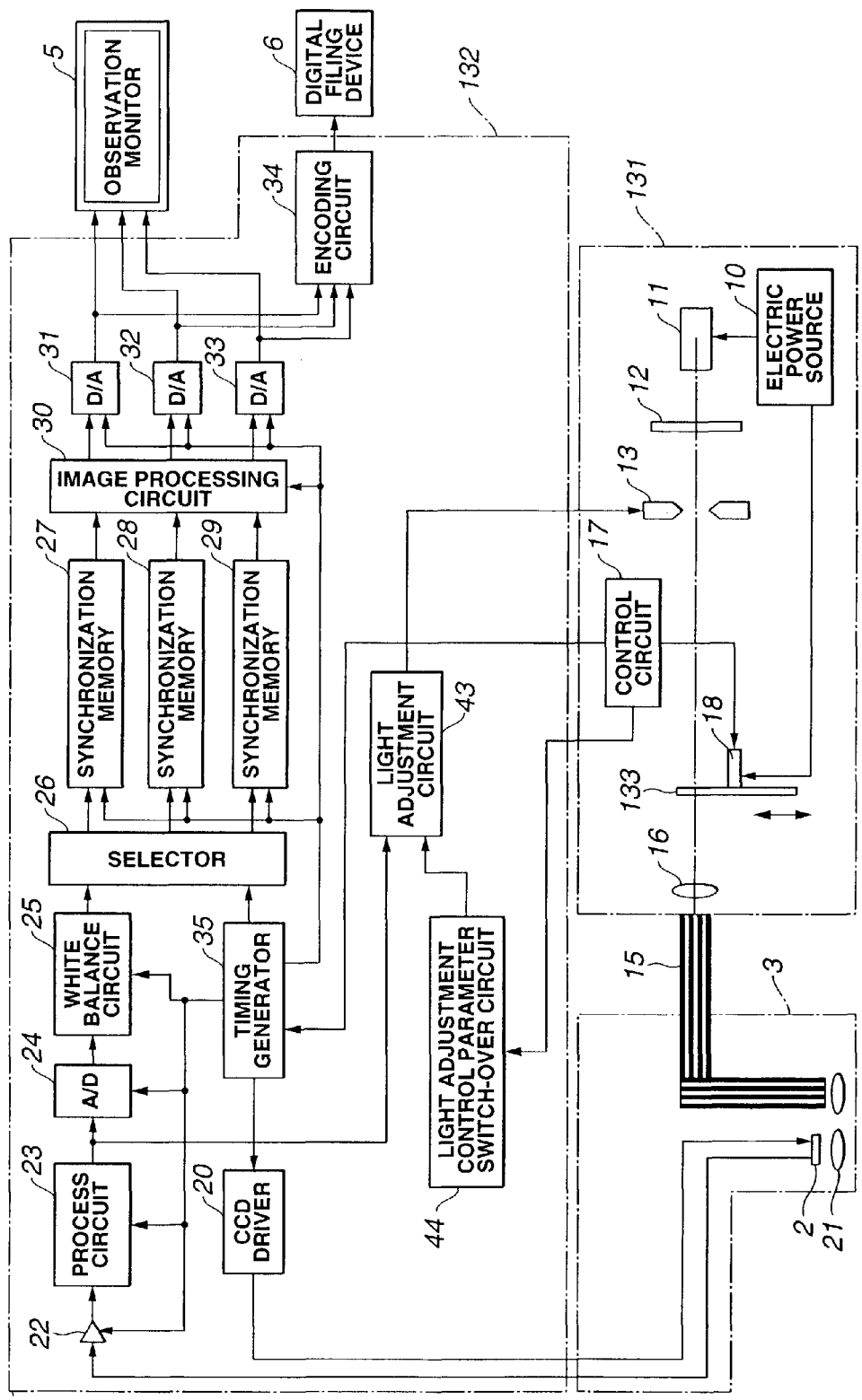
FIG. 58 is a configuration diagram illustrating the configuration of an endoscope device according to an eighth embodiment of the present invention.

FIG. 58 is a configuration diagram illustrating the configuration of an endoscope device according to an eighth embodiment of the present invention.

The eighth embodiment is almost the same as the first embodiment, so only the differing points will be described, and the same configurations will be denoted with the same reference numerals and description thereof will be omitted.

As shown in FIG. 58, the present embodiment is a narrow-band observation endoscope device having a narrow-band light source device 131 dedicated for supplying narrow-band frame sequence light to the electronic endoscope 3, and a narrow-band video processor 132 dedicated for processing the narrow-band frame sequence light captured by the electronic endoscope 3

A narrow-band rotating filter 133 provided in the light source device 131 is configured of the R2 filter 14r2, G2 filter 14g2, and B2 filter 14b2 (see FIG. 4), for generating narrow-band RGB frame sequence light.

Thus, the present embodiment also enables narrow-band observation with narrow-band frame sequence light.

Also, in the event that the narrow-band light source device 131 having the narrow-band rotating filter 133 is connected to the narrow-band video processor 132, information relating to the type of illumination light spectral properties of the narrow-band light source device 131 are output from the control circuit 17 of the narrow-band illumination light device 131 to the light adjustment control parameter switch-over circuit 44, as identification signals. The correlation between the identification signals and the control parameters is recorded in the light adjustment parameter switch-over circuit 44 beforehand in the form of a correlation table, and appropriate control signals are output to the light adjusting circuit 43 based on the correlation table, and consequently, light adjustment control according to the illumination light spectral properties is enabled.

Figure 59:
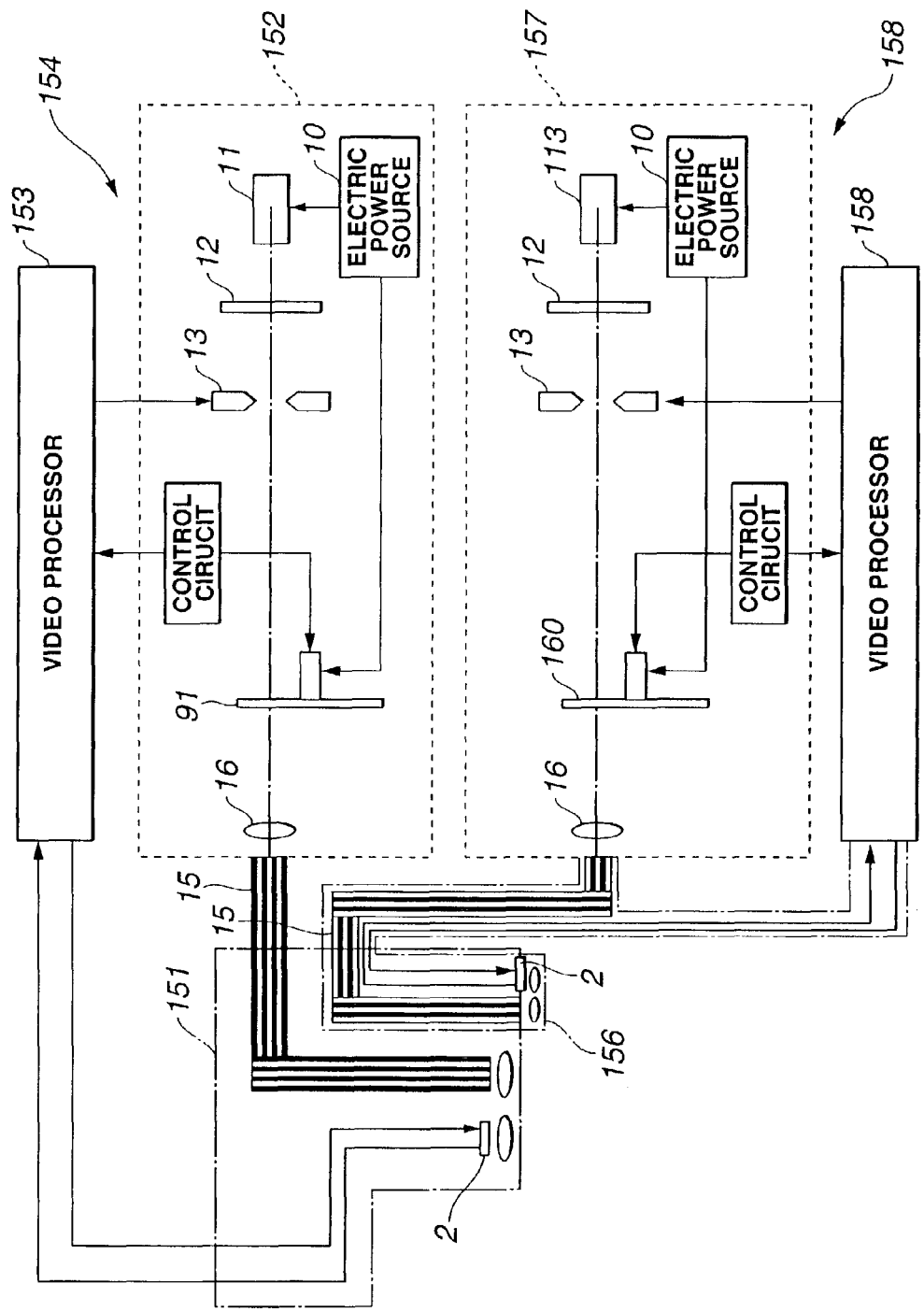
FIG. 59 is a configuration diagram illustrating the configuration of an endoscope device according to a ninth embodiment of the present invention.
Figure 60:
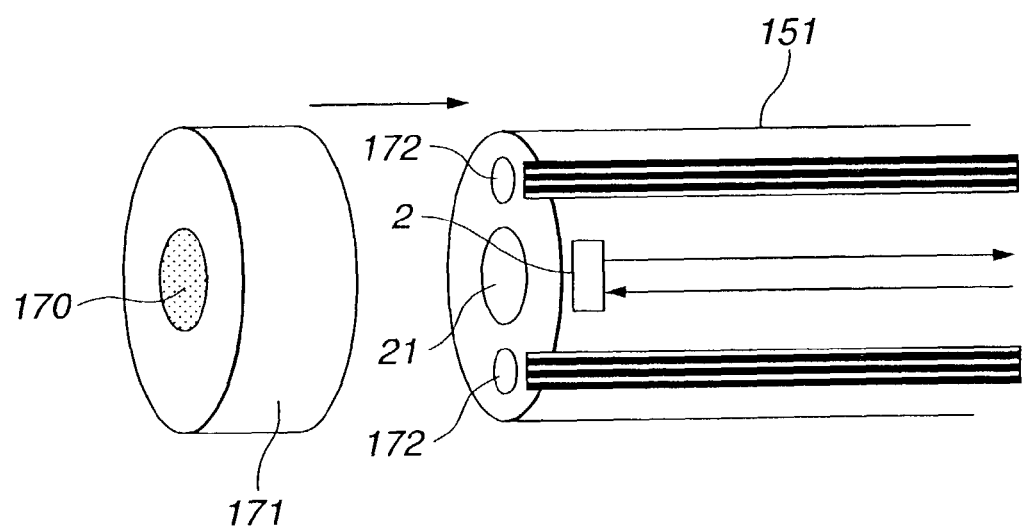
FIG. 60 is a diagram illustrating an adapter having a band restricting filter which is mountable in the tip of the electronic endoscope shown in FIG. 59.

FIG. 59 and FIG. 60 relate to a ninth embodiment of the present invention, wherein FIG. 59 is a configuration diagram illustrating the configuration of an endoscope device, and FIG. 60 is a diagram illustrating an adapter having a band restricting filter which is mountable on the tip of the electronic endoscope shown in FIG. 59.

The ninth embodiment is almost the same as the first embodiment, so only the differing points will be described, and the same configurations will be denoted with the same reference numerals and description thereof will be omitted.

As shown in FIG. 59, the present embodiment comprises a normal observation electronic endoscope 151, an endoscope device 154 having a light source device 152 for supplying normal observation frame sequence light to the electronic endoscope 151 and a video processor 153 for performing signal processing on image-pickup signals from the electronic endoscope 151, and a narrow-band light observation endoscope device 155 provided separately from this endoscope device 154. Here, this light source device 152 has the xenon lamp 11 and diaphragm device 13, and the rotating filter 91 upon which are disposed the R1 filter 14r1, G1 filter 14g1, and B1 filter 14b1.

The narrow-band light observation endoscope device 155 comprises a small-diameter electronic endoscope 156 to be inserted through the treatment equipment channel of the electronic endoscope 151, a light source device 157 for supplying narrow-band frame sequence light to the small-diameter electronic endoscope 156, and a video processor 158 for signal processing image-pickup signals from the small-diameter electronic endoscope 156. The light source device 152 has the extra-high pressure mercury lamp 113 and diaphragm device 13, and a rotating filter 160 upon which are disposed the R2 filter 14r2, G2 filter 14g2, and B2 filter 14b2.

Normal observation is performed using the endoscope device 154, and narrow-band light observation is performed using the narrow-band light observation endoscope device 155.

According to the present embodiment, the same advantages as those of the first embodiment can be obtained.

Further, a normal endoscope can be connected to the narrow-band light observation endoscope device 155.

Also, an adapter 171 having a bandwidth restricting filter 170 such as shown in FIG. 58 may be mounted on the tip of the above-described electronic endoscope. Thus, narrow-band light observation can be performed using the endoscope device 154.

Also, while FIG. 60 is an example of mounting the adapter 171 to which is applied the bandwidth restricting filter 170 on the front face of the objective optical system 21, an arrangement may be made wherein the bandwidth restricting filter 170 is mounted in the front face of an illumination lens 172.

As described above, according to the above first through ninth embodiments, tissue information of a desired depth near the tissue surface of living body tissue can be obtained.

Next, a tenth embodiment of the present invention will be described with reference to FIG. 61 through FIG. 74.

Figure 61:
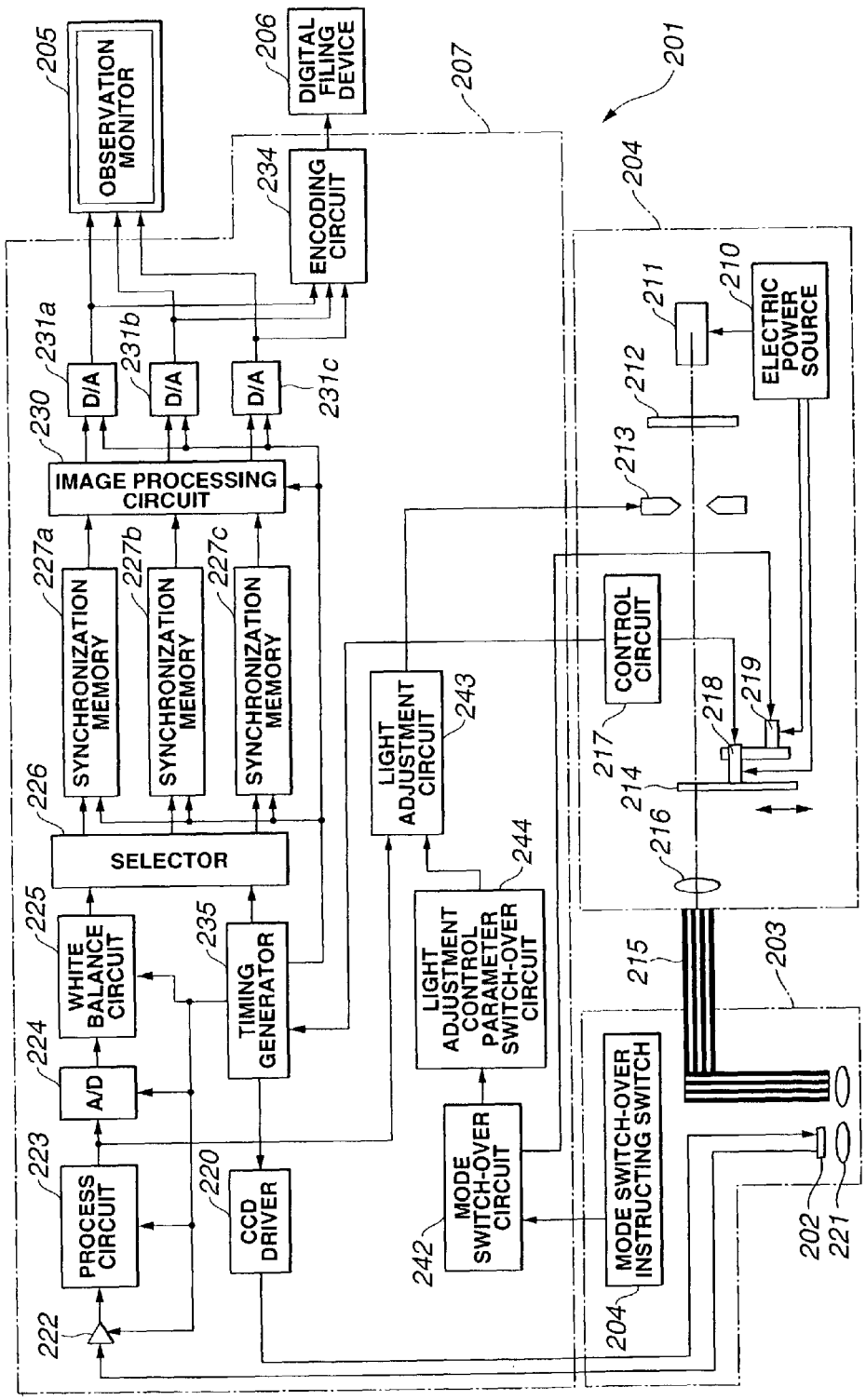
FIG. 61 is a configuration diagram illustrating the configuration of an endoscope device according to a tenth embodiment of the present invention.
Figure 62:
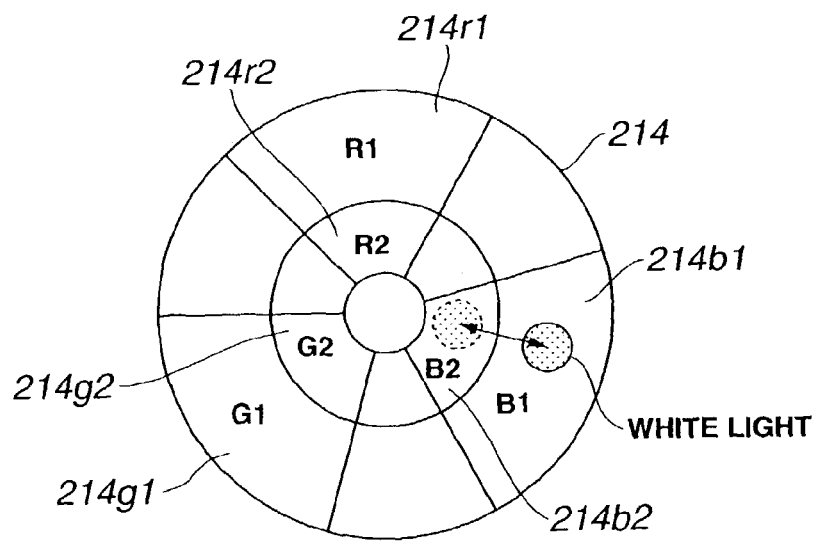
FIG. 62 is a configuration diagram illustrating the configuration of the rotating filter shown in FIG. 61.
Figure 63:
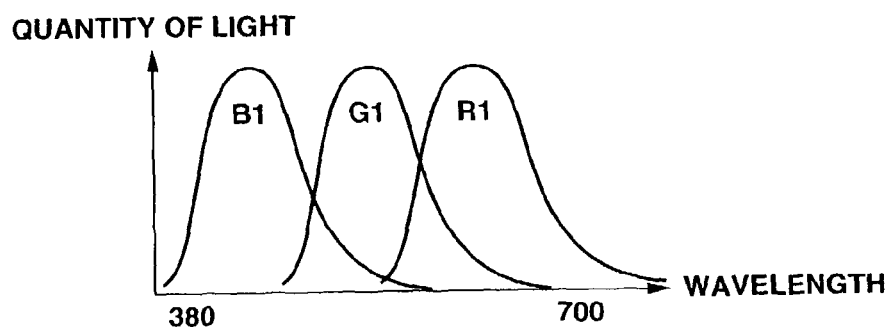
FIG. 63 is a diagram illustrating the spectral properties of a first filter set of the rotating filter shown in FIG. 62.
Figure 64:
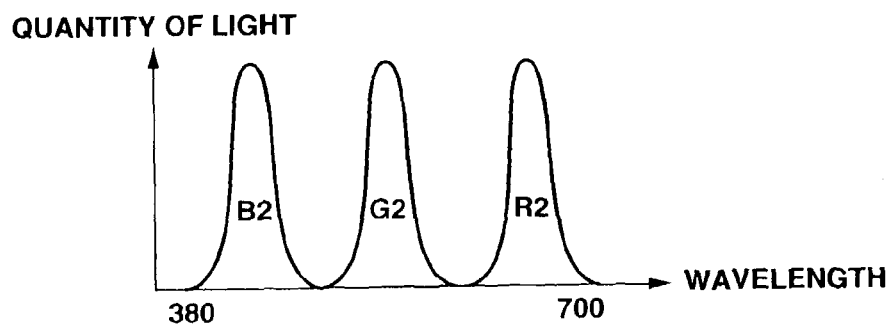
FIG. 64 is a diagram illustrating the spectral properties of a second filter set of the rotating filter shown in FIG. 62.
Figure 65:
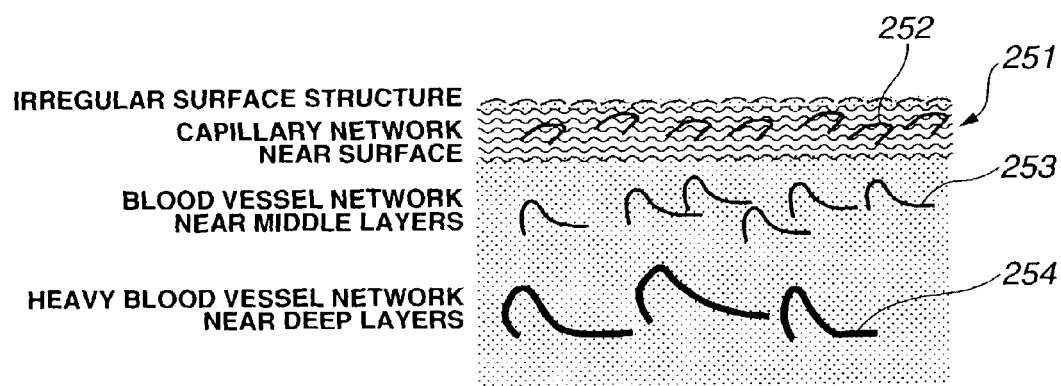
FIG. 65 is a diagram illustrating the structure of the living body tissue to be observed with the endoscope device shown in FIG. 61, in the layer direction.
Figure 66:
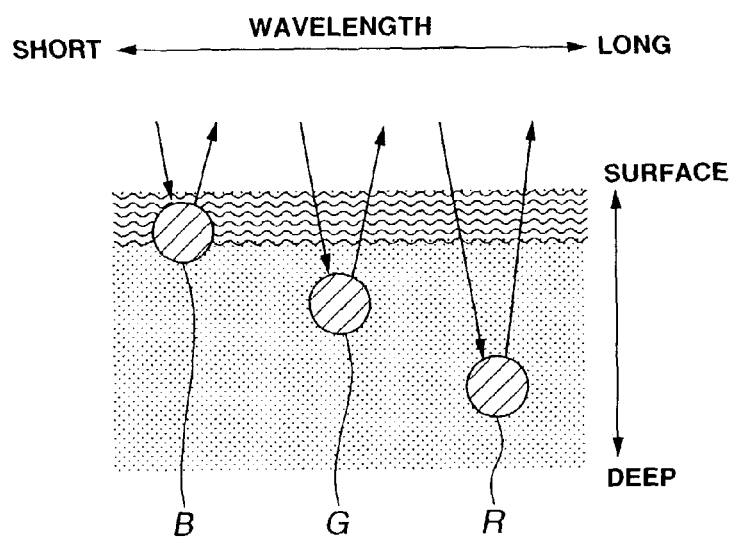
FIG. 66 is a diagram describing the state of the illumination light from the endoscope device shown in FIG. 61 reaching the living body tissue in the layer direction.
Figure 67A:
FIGS. 67a-c are diagrams illustrating each of the band images from frame sequence light transmitted through the first filter set shown in FIG. 63.
Figure 67B:
Figure 67C:
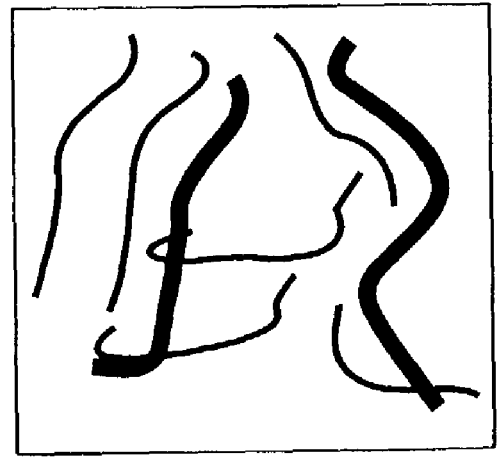
Figure 68A:
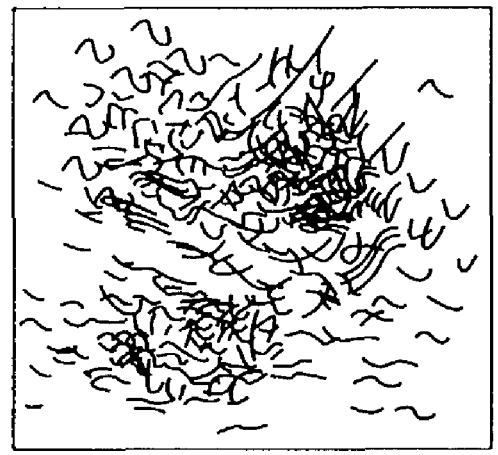
FIGS. 68a-c are diagrams illustrating each of the band images from frame sequence light transmitted through the second filter set shown in FIG. 64.
Figure 68B:
Figure 68C:
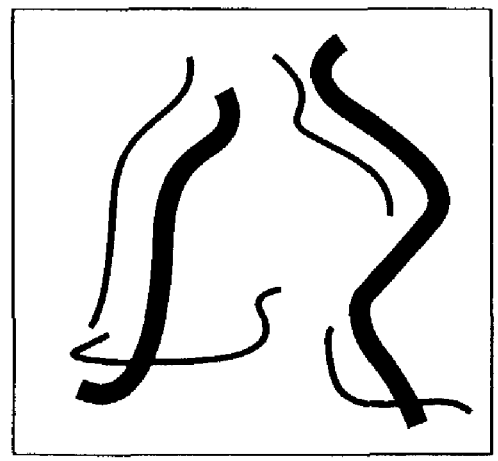
Figure 69:
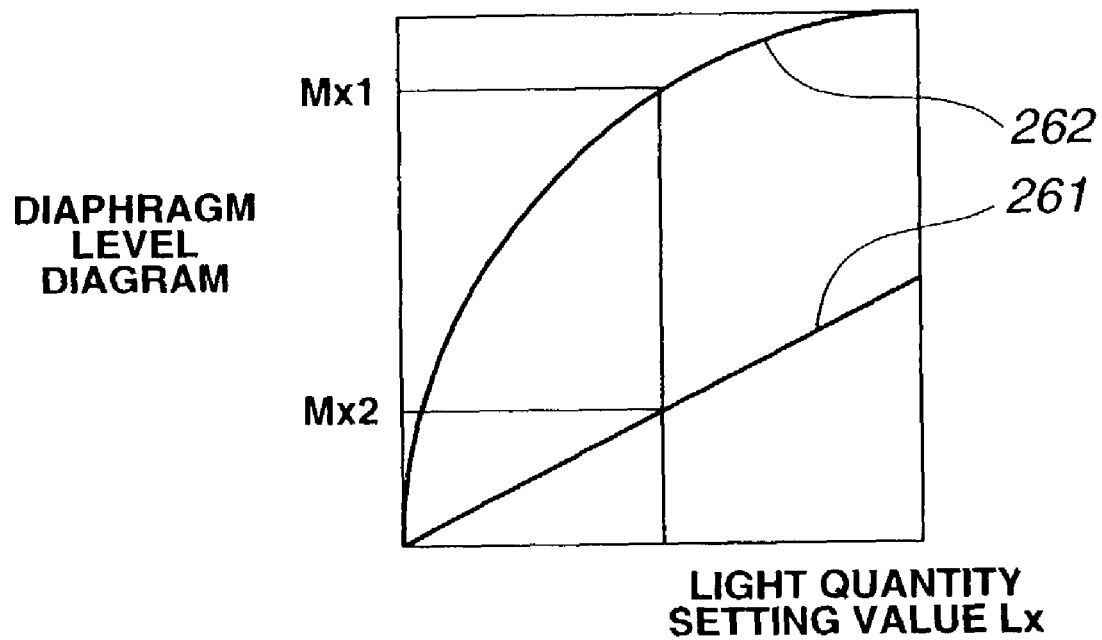
FIG. 69 is a diagram describing light adjustment control by a light adjusting circuit shown in FIG. 61.
Figure 70:
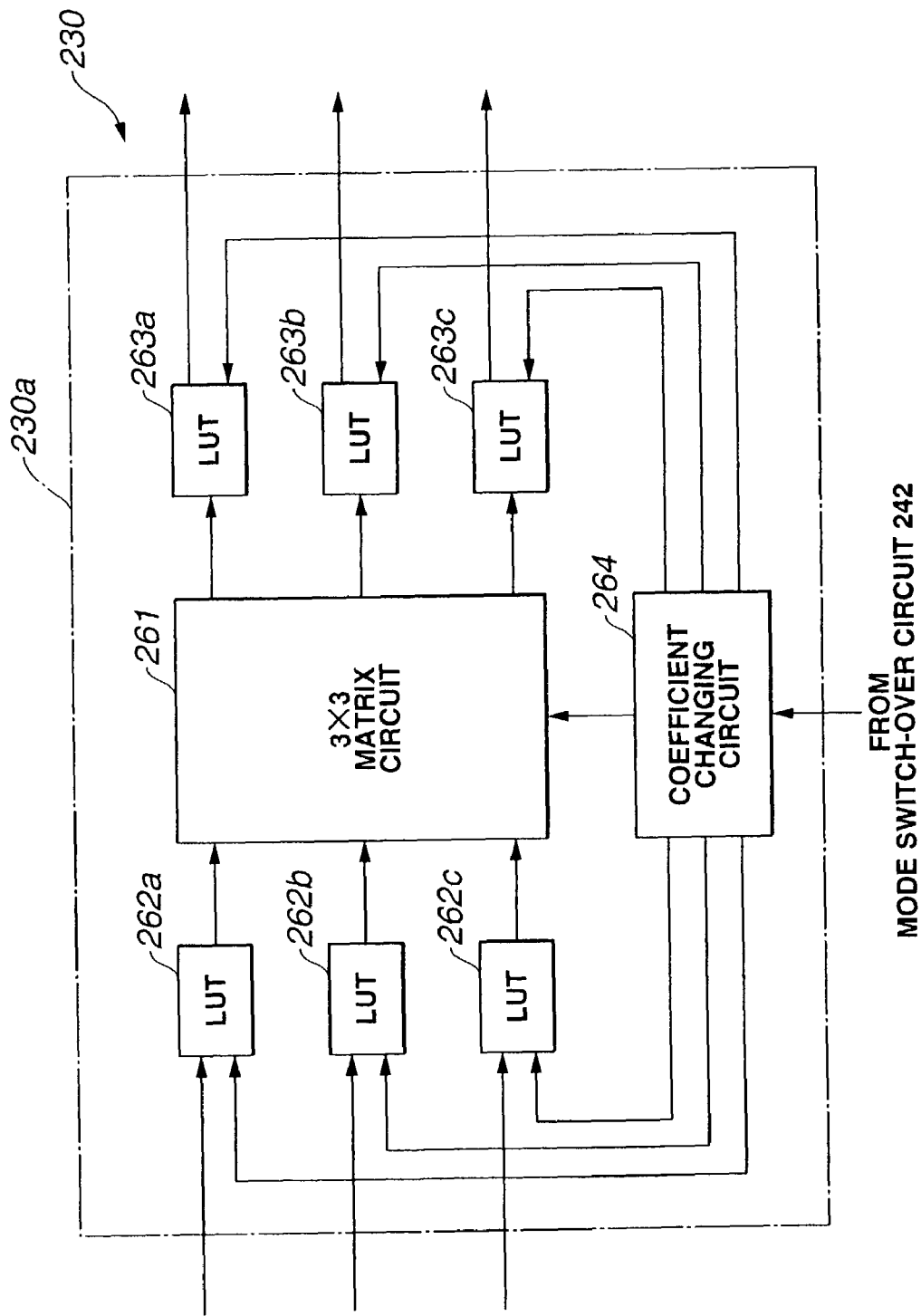
FIG. 70 is a configuration diagram illustrating the configuration of the image processing circuit shown in FIG. 61.
Figure 71:
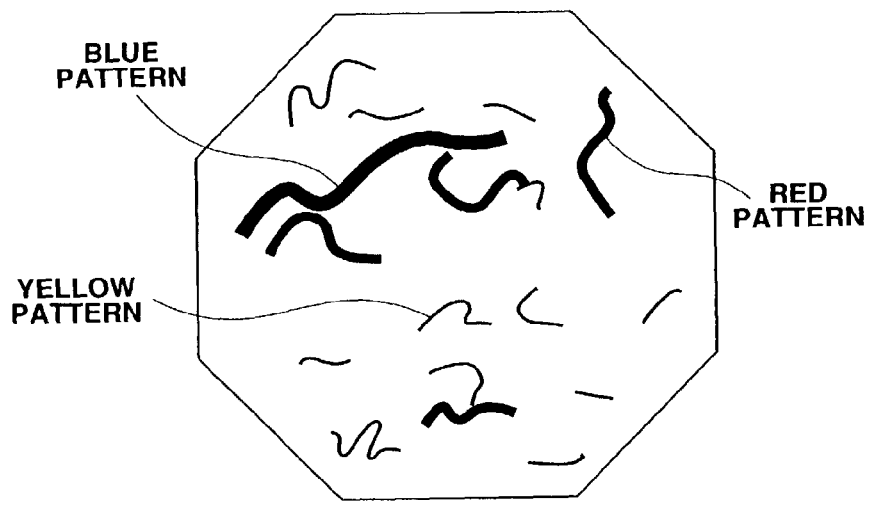
FIG. 71 is a diagram illustrating a color image of a narrow-band RGB image obtained by the image processing circuit shown in FIG. 70.
Figure 72:
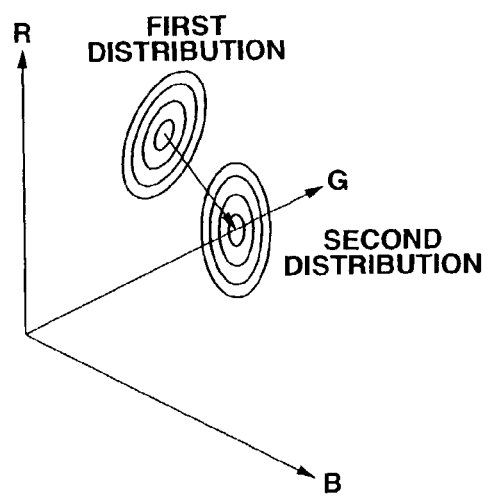
FIG. 72 is a diagram describing the creation of a matrix such that an average color tone is maintained in the 3×3 matrix circuit shown in FIG. 70.
Figure 73:
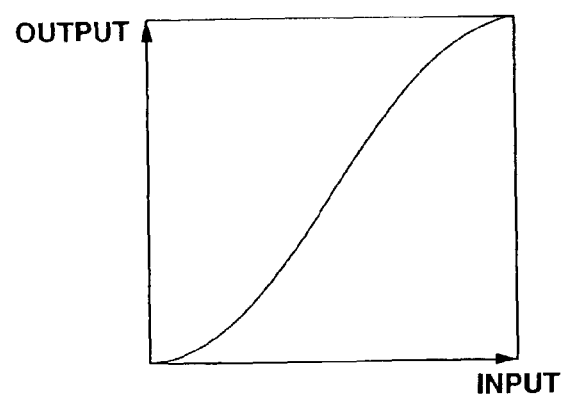
FIG. 73 is a diagram illustrating an example of settings of the LUT shown in FIG. 70.
Figure 74:
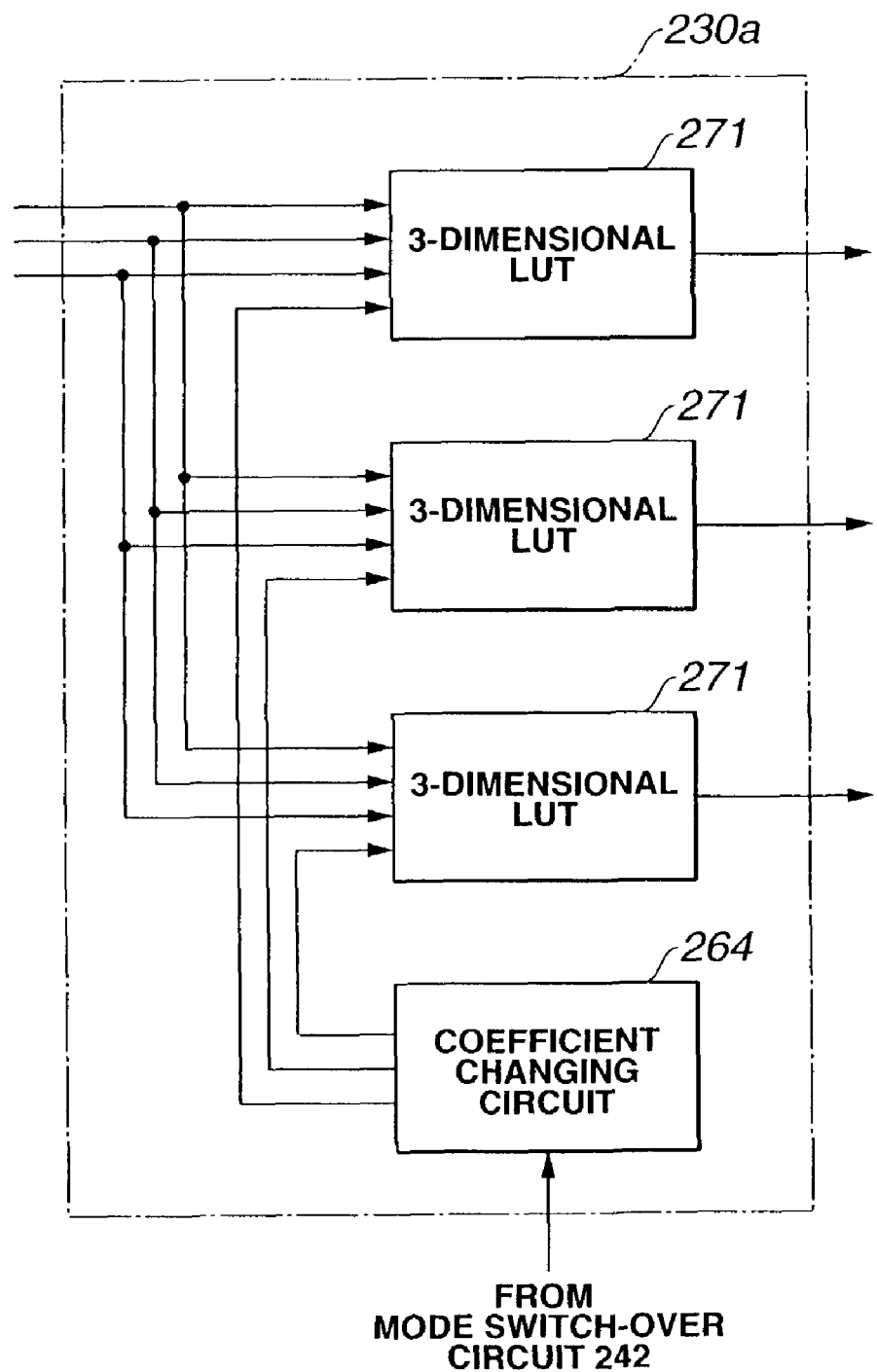
FIG. 74 is a configuration diagram illustrating the configuration of a modification made to the color conversion processing circuit shown in FIG. 70.

FIG. 61 is a configuration diagram illustrating the configuration of an endoscope device, FIG. 62 is a configuration diagram illustrating the configuration of the rotating filter shown in FIG. 61, FIG. 63 is a diagram illustrating the spectral properties of a first filter set of the rotating filter shown in FIG. 62, FIG. 64 is a diagram illustrating the spectral properties of a second filter set of the rotating filter shown in FIG. 62, FIG. 65 is a diagram illustrating the structure of the living body tissue to be observed with the endoscope device shown in FIG. 1, in the layer direction, FIG. 66 is a diagram describing the state of the illumination light from the endoscope device shown in FIG. 61 reaching the living body tissue in the layer direction, FIG. 67 is a diagram illustrating each of the band images from frame sequence light transmitted through the first filter set shown in FIG. 63, FIG. 68 is a diagram illustrating each of the band images from frame sequence light transmitted through the second filter set shown in FIG. 64, FIG. 69 is a diagram describing light adjustment control by a light adjusting circuit shown in FIG. 61, FIG. 70 is a configuration diagram illustrating the configuration of the image processing circuit shown in FIG. 61, FIG. 71 is a diagram illustrating a color image of a narrow-band RGB image obtained by the image processing circuit shown in FIG. 70, FIG. 72 is a diagram describing the creation of a matrix such that an average color tone is maintained in the 3×3 matrix circuit shown in FIG. 70, FIG. 73 is a diagram illustrating an example of settings of the LUT shown in FIG. 610, and FIG. 74 is a configuration diagram illustrating the configuration of a modification made to the color conversion processing circuit shown in FIG. 70.

As shown in FIG. 61, an endoscope device 201 according to the present embodiment comprises an electronic endoscope 203 having a CCD 202 serving as image-pickup means to be inserted into the body cavity and capture images of tissue within the body cavity, a light source device 204 for supplying illumination light to the electronic endoscope, and a video processor 207 for performing signal processing on image-pickup signals from the CCD 202 of the electronic endoscope 203 and displaying endoscopic images on an observation monitor 205 or encoding the endoscopic images and outputting to an image filing device 206 as compressed images.

The light source device 204 is configured of a xenon lamp 211 for emitting illumination light, a heat ray cut filter 212 for shielding heat rays from the white light, a diaphragm device 213 for controlling the light quantity of the white light through the heat ray cut filter 212, a rotating filter 214 for turning the illumination light into frame sequence light, a condenser lens 216 for collecting the frame sequence light coming through the rotating filter 214 onto the incident face of a light guide 215 disposed within the electronic endoscope 203, and a control circuit 217 for controlling the rotation of the rotating filter 214.

As shown in FIG. 62, the rotating filter 214 is formed in a disk-like shape and has a double structure with the center as the rotating axis, wherein an R1 filter 214r1, a G1 filter 214g1, and a B1 filter 214b1 making up a first filter set for outputting frame sequence light having overlapping spectral properties suitable for natural color reproduction such as indicated in FIG. 63 situated on the outer sector, and wherein an R2 filter 214r2, a G2 filter 214g2, and a B2 filter 214b2 making up a second filter set for outputting narrow-band frame sequence light having discrete spectral properties enabling extraction of desired deep tissue information such as indicated in FIG. 64 situated on the inner sector. As shown in FIG. 61, the rotating filter 214 is rotated by the control circuit 217 performing driving control of a rotating filter motor 218, and movement in the radial direction (movement which is perpendicular to the optical path of the rotating filter 214, which is selectively moving the first filter set or second filter set of the rotating filter 214 onto the optical path) is performed by a mode switch-over motor 219 by control signals from a mode switch-over circuit 242 within the later-described video processor 207.

Note that electric power is applied to the xenon lamp 211, diaphragm device 213, rotating filter motor 218, and mode switch-over motor 219, from an electric power supply unit 210.

Returning to FIG. 61, the video processor 207 is configured comprising: a CCD driving circuit 220 for driving the CCD 202; an amplifier 222 for amplifying image-pickup signals wherein images are captured from the body cavity tissue by the CCD 202 through an objective optical system 221; a process circuit 223 for performing correlated double sampling and noise reduction and so forth, with regard to image-pickup signals coming through the amplifier 222; an A/D converter 224 for converting the image-pickup signals passing through the process circuit 223 into image data of digital signals; a white balance circuit 225 for subjecting the image data from the A/D converter 224 to white balance processing; the selector 226 and synchronizing memory 227a, 227b, and 227c, for synchronizing the frame sequence light from the rotating filter 214; an image processing circuit 230 for reading out each set of image data of the frame sequence light stored in the synchronizing memory 227a, 227b, 227c, and subjecting these to gamma correction processing, outline enhancement processing, color processing, etc; D/A circuits 231a, 231b, and 231c, for converting the image data from the image processing circuit 230 into analog signals; an encoding circuit 234 for encoding the output of the D/A circuits 231a, 231b, and 231c; and a timing generator 235 for inputting synchronizing signals synchronized with the rotation of the rotating filter 214 from the control circuit 217 of the light source device 204, and outputting various types of timing signals to the above-described circuits.

Also, a mode switch-over switch 241 is provided in the electronic endoscope 203, with the output of this mode switch-over switch 241 being output to the mode switch-over circuit 242 within the video processor 207. The mode switch-over circuit 242 of the video processor 207 outputs control signals to a light adjusting circuit 243, a light adjustment control parameter switch-over circuit 244, and mode switch-over motor 219 of the light source device 204. The light adjustment control parameter switch-over circuit 244 outputs light adjustment control parameters corresponding to the first filter set or second filter set of the rotating filter 214 to the light adjusting circuit 243, and the light adjusting circuit 243 controls the diaphragm device 213 of the light source device 204 based on the control signals from the mode switch-over circuit 242 and light adjustment parameters from the light adjustment control parameter switch-over circuit 244, so as to perform appropriate brightness control.

As shown in FIG. 65, a body cavity tissue 251 often has a structure wherein there is a distribution of different absorbent material such as blood vessels in the depth direction, for example. There is primarily a greater distribution of capillaries 252 near the surface of mucus membranes, blood vessels 253 which are thicker than the capillaries are also distributed along with capillaries at the middle layer which is deeper than this layer, and even thicker blood vessels 254 are distributed at even deeper layers.

On the other hand, the permeation depth of the light in the depth direction as to the body cavity tissue 251 is dependent on the wavelength of light, and with illumination light containing the visible region, as shown in FIG. 66, in the case of light with a short wavelength such as blue (B), the light only reaches around the surface layer due to the absorption properties and scattering properties at the living body tissue, being subjected to absorption and scattering within the range up to that depth, so light coming out from the surface is observed. Also, in the case of green (G) light with a wavelength longer than that of blue (B) light, the light reaches a depth deeper than the range where the blue (B) light reaches, is subjected to absorption and scattering within the range at that depth, and light coming out from the surface is observed. Further, red (R) light with a wavelength longer than that of green (G) light, reaches a range even deeper.

At the time of performing normal observation, the mode switch-over circuit within the video processor 207 controls the mode switch-over motor 219 with control signals, so that the R1 filter 214r1, G1 filter 214g1, and B1 filter 214b1, making up the first filter set of the rotating filter 214, are positioned on the optical path of the illumination light.

With the R1 filter 214r1, G1 filter 214g1, and B1 filter 214b, the wavelength regions are each overlapped as shown in FIG. 63, so at the time of normal observation of the body cavity tissue 251, a band image having shallow layer and middle layer tissue information containing a great amount of tissue information at the shallow layer such as shown by "a" in FIG. 67 is captured in the image-pickup signals which are captured by the CCD 202 with the B1 filter 214b1, a band image having shallow layer and middle layer tissue information containing a great amount of tissue information at the middle layer such as shown in "b" in FIG. 67 is captured into the image-pickup signals that are captured by the CCD 202 with the G1 filter 214g1, and further, a band image having middle layer and deep layer tissue information containing a great amount of tissue information at the deep layer such shown in "c" in FIG. 67 is captured into the image-pickup signals which are captured by the CCD 202 with the R1 filter 214r1.

These RGB image-pickup signals are synchronized with the video processor 207 and subjected to signal processing, thus enabling an endoscopic image with desired or natural color reproduction to be obtained as an endoscopic image.

On the other hand, upon the mode switch-over switch 241 of the electronic endoscope 203 being pressed, the signals thereof are input into the mode switch-over circuit 242 of the video processor 207. The mode switch-over circuit 242 outputs control signals to the mode switch-over motor 219 of the light source device 204, thereby moving the first filter set of the rotating filter 214 that was on the optical path at the time of normal observation, and drives the rotating filter 214 with respect to the optical path so that the second filter set is positioned upon the optical path.

In the event of performing narrow-band light observation of the body cavity tissue 251 with the second filter set, the R2 filter 214r2, G2 filter 214g2, and B2 filter 214b2 make the illumination light to be narrow-band frame sequence light with discrete spectral properties as shown in FIG. 64, so a band image having tissue information at a shallow layer such as shown in "a" in FIG. 68 is captured into the image-pickup signals which are captured by the CCD 202 with the B2 filter 214b2, a band image having tissue information at the middle layer such as shown in "b" in FIG. 68 is captured into the image-pickup signals which are captured by the CCD 202 with the G2 filter 214g2, and a band image having tissue information at the deep layer such as shown in "c" in FIG. 68 is captured into the image-pickup signals which are captured by the CCD 202 with the R2 filter 214r2.

As can be clearly understood from FIG. 63 and FIG. 64, at this time, the quantity of transmitted light from the second filter set is less than the quantity of transmitted light from the first filter set, because the bands thereof are narrowed, so the light adjusting circuit 243 controls the diaphragm device 213 by outputting light adjustment control parameters according to the first filter set or second filter set of the rotating filter 214, from the light adjustment control parameter switch-over circuit 244 to the light adjusting circuit 243, thereby, as shown in FIG. 69, controlling the diaphragm device 213 when making narrow-band light observation so as to control light quantity Mx with a diaphragm control curve 262 corresponding to a set value Lx, with respect to, for example, a linear diaphragm control line 261 by the diaphragm device 213 in normal observation, corresponding to the set value Lx on an unshown setting panel of the video processor 207. Thus, image data with sufficient brightness can be obtained at the time of narrow-band light observation, as well.

Specifically, the aperture level value corresponding to the light quantity setting value Lx changes from Mx1 to Mx2 as shown in FIG. 69, being interlocked with changing the first filter set to the second filter set, and consequently, the diaphragm is controlled in the direction of being opened, and acts to compensate for reduction in the quantity of illumination light by the filters which narrows the band.

As shown in FIG. 70, an image processing circuit 230 comprises three sets each of LUTs 262a, 262b, 262c, 263a, 263b, and 263c, fore and aft, across a 3×3 matrix circuit 261, and a coefficient changing circuit 264 for converting table data of the LUTs 262a, 262b, 262c, 263a, 263b, and 263c, and the coefficients of the 3×3 matrix circuit 261, thus configuring a color conversion processing circuit 230a.

The RGB data input to the color conversion processing circuit 230a is converted by the LUTs 262a, 262b, and 262c, for each band data. Here, inverse γ correction, non-linear contrast conversion, etc., is performed.

Next, following color conversion being performed at the 3×3 matrix circuit 261, γ correction and suitable tone conversion processing is performed at the latter LUTs 263a, 263b, and 263c.

Change can be made at a coefficient changing circuit 264 for converting table data of the LUTs 262a, 262b, 262c, 263a, 263b, and 263c, and the coefficients of the 3×3 matrix circuit 261.

Changing with the coefficient changing circuit 264 is based on control signals from the mode switch-over circuit 242 or a processing conversion switch (not shown) provided on the operating unit or the like of the electronic endoscope 203.

Upon receiving the control signals, the coefficient changing circuit 263 calls up appropriate data from the coefficient data described in the image processing circuit 230 beforehand, and rewrites the current circuit coefficients with this data.

Next, the contents of color conversion processing will be described specifically. Expression 1 shows an example of a color conversion expression.

Expression 1

$$R \rightarrow R$$
$$G \rightarrow \omega_G G + \omega_B B \quad (1)$$
$$B \rightarrow B$$

The processing according to Expression 1 is an example of conversion for taking data generated by a B image having been mixed with G at a certain ratio and taking this anew as a G image. Making the illumination light for each band to be narrow-band can further clarify that absorbents and scatterers such as blood vessel networks differ according to depth position.

That is to say, the difference in information relating to body structures which each band reflect can be further increased by making the illumination light to be narrow-band.

In the event of observing these narrow-band RGB images as color images, this will be an image such as shown in FIG. 71, for example. The thick blood vessels are at deep positions, and are reflected in the R band image, indicated by a blue color pattern as the color thereof. The blood vessel network near the middle layers is intensely reflected in the G image, and is indicated as a red color pattern for the color image thereof. Of the blood vessel networks, those existing near the surface of the mucous membrane are represented as a yellow color pattern.

Particularly, the change in pattern near the surface of the mucous membrane is crucial for early discovery and differential diagnosis of early disorders. However, yellow patterns have little contrast with the background mucous membrane, and accordingly the visibility thereof tends to be low.

Accordingly, the conversion shown in Expression 1 is valid for clearly reproducing the patterns near the surface of the mucous membrane. Expression 1 can be expressed in matrix format as shown in Expression 2.

Expression 2

$$\begin{pmatrix} R' \\ G' \\ B' \end{pmatrix} = \begin{pmatrix} 1 & 0 & 0 \\ 0 & \omega_G & \omega_B \\ 0 & 0 & 1 \end{pmatrix} \begin{pmatrix} R \\ G \\ B \end{pmatrix} \quad (2)$$

Accordingly, adjusting the matrix coefficients through the coefficient changing circuit 264 allows the user to adjust the display effects. As for the operations, synchronously with a mode switch-over switch (not shown) provided to the operating unit of the electronic endoscope 203, the matrix coefficients are set to default values from a through operation within the image processing means.

The through operation here refers to a state wherein the 3×3 matrix circuit 261 carries a unit matrix, and the LUTs 262*a*, 262*b*, 262*c*, 263*a*, 263*b*, and 263*c* carry non-conversion tables. Default values are to provide the matrix coefficients with set values of, for example, ωG=0.2, ωB=0.8.

The user then operates a processing changing switch or the like provided to the operating unit of the electronic endoscope 203 or the video processor casing panel or the like, and performs adjustment so that the coefficients are ωG=0.4, ωB=0.6, and so forth. If necessary, inverse γ correction tables and γ correction tables are applied to the LUTs 262*a*, 262*b*, 262*c*, 263*a*, 263*b*, and 263*c*.

Next, description will be made wherein color correction is performed so as to maintain an average color tone as much as possible even in the event that the filter is switched, at the color conversion processing circuit 230*a*.

As a result of filter switching, the spectral properties of the illumination light change. Consequently, color reproduction also changes. Depending on the state of usage or the user, there may be cases wherein maintaining average color reproduction as much as possible is desired while maintaining improved contrast of minute structure at the surface of the mucous membrane. In such cases, there is the need to change the operations by the coefficient changing circuit 264 so as to perform color conversion operations wherein the average color tone is maintained from the through operation, in accordance with the filter switching.

Procedures for creating a matrix for maintaining average color tone are shown below. As shown in FIG. 72, let us say that the color distribution of a subject in an RGB color space moves from a first distribution to a second distribution, corresponding to filter switching. In such a case, at least three points are selected from the first distribution (normally containing distribution average and center-of-gravity data), and where in the second distribution these three points move to is checked. Then, a conversion matrix from the second distribution to the first distribution is calculated using the three sets of data, and used as the matrix coefficients for the 3×3 matrix circuit 261. Note that three or more points can be selected and determined by the method of least-squares.

Color reproduction which maintains average color tone as much as possible can be attained even when switching filters, by applying the above matrix coefficients to the LUTs 262*a*, 262*b*, 262*c*, 263*a*, 263*b*, and 263*c*, using inverse γ correction and γ correction tables as necessary.

Also, image effects such as pigment dying can be reproduced with a B image alone, taking advantage of the fact that the narrow-band B image reflects the minute structures of the surface of mucous membranes well, such as pit patterns. That is to say, the output RGB data is configured of only the B data out of the RGB data input by the matrix conversion expression indicated in Expression 3.

Expression 3

$$\begin{pmatrix} R' \\ G' \\ B' \end{pmatrix} = \begin{pmatrix} 0 & 0 & \omega_R \\ 0 & 0 & \omega_G \\ 0 & 0 & \omega_B \end{pmatrix} \begin{pmatrix} R \\ G \\ B \end{pmatrix} \quad (3)$$

Adjusting the coefficients then allows effects such as pigment dying images to be exhibited. For example, with settings wherein ωB>>ωG, ωR, the image exhibits a bluish tone, and has the tone of the same color as performing indigo dying. Also, with settings wherein ωB, ωR>>ωR, the image exhibits a purplish tone, and has the tone of the same color as performing methyl violet dying. Further, setting the LUT settings such as shown in FIG. 73 results in hard reproduction for the contrast, and images with high contrast such as with dyed images can be obtained.

Thus, according to the present embodiment, setting the parameters of the color conversion processing circuit 230*a* synchronously with the filter switching allows a representation method which takes advantage of the characteristic of narrow-band RGB illumination light, namely, permeation depth information, to be realized, so tissue information at desired depths near the tissue surface of living body tissue can be separated and visually recognized.

Now, with the above embodiment, the color conversion processing circuit 230*a* is described as a configuration with the 3×3 matrix circuit 261 at the center, but the same advantages can be obtained by replacing the color conversion processing circuit 230*a* with 3-dimensional LUTs 271 corresponding to each band, as shown in FIG. 74. In this case, the coefficient changing circuit 264 performs operations for changing the contents of the tables based on control signals from the mode switch-over circuit 242.

Next, an eleventh embodiment of the present invention will be described with reference to FIG. 75 through FIG. 78.

Figure 75:
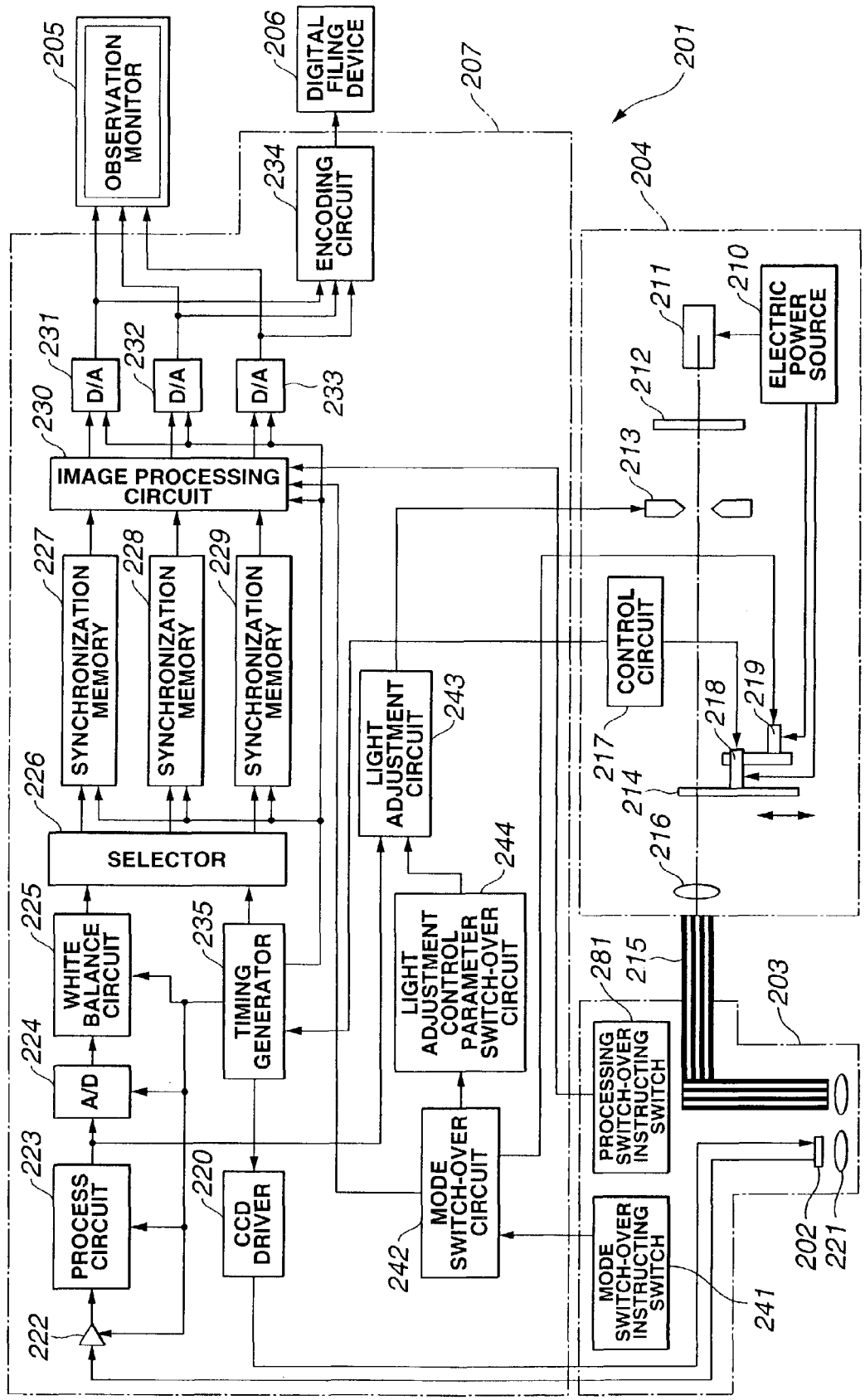
FIG. 75 is a configuration diagram illustrating the configuration of an endoscope device according to an eleventh embodiment of the present invention.
Figure 76:
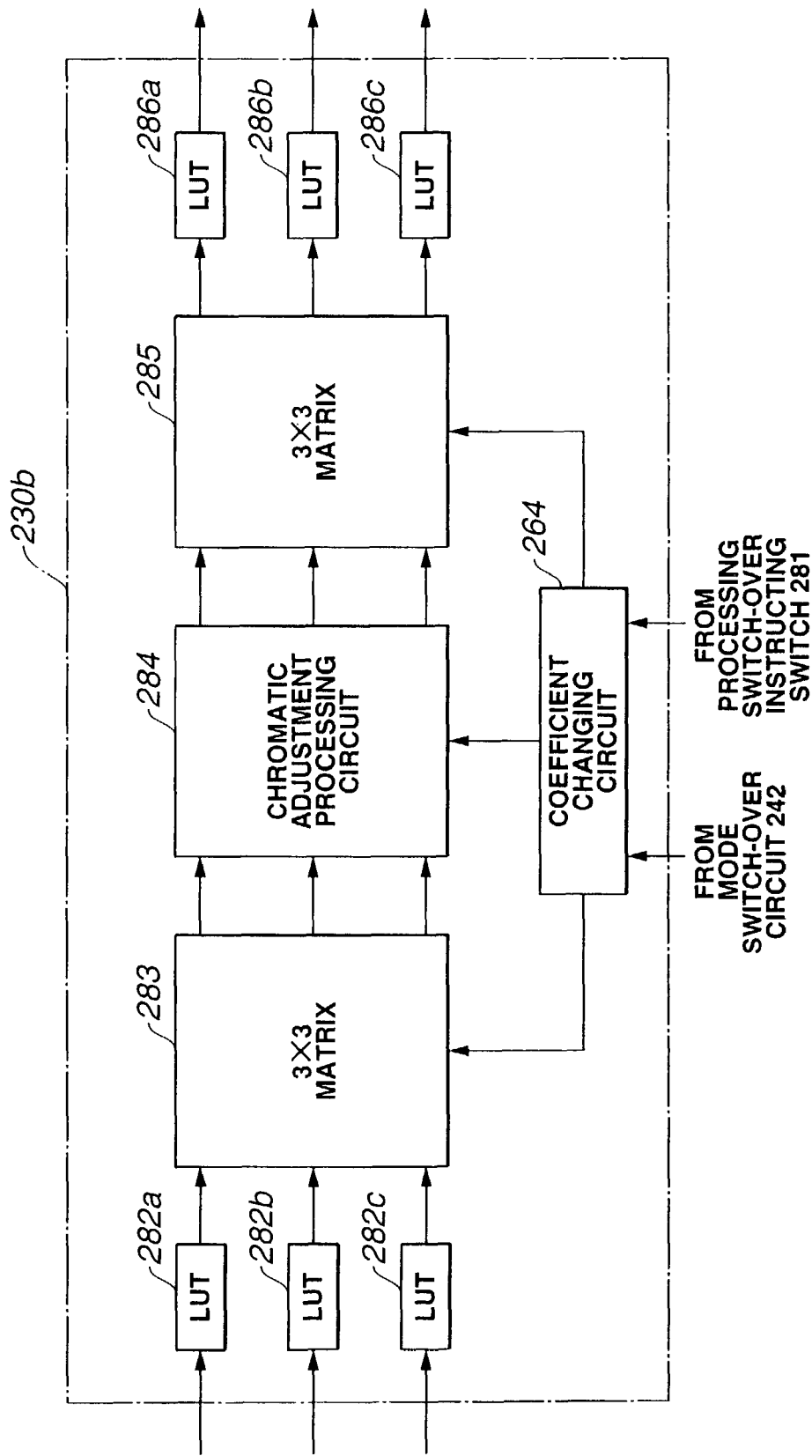
FIG. 76 is a configuration diagram illustrating the configuration of the image processing circuit shown in FIG. 75.
Figure 77:
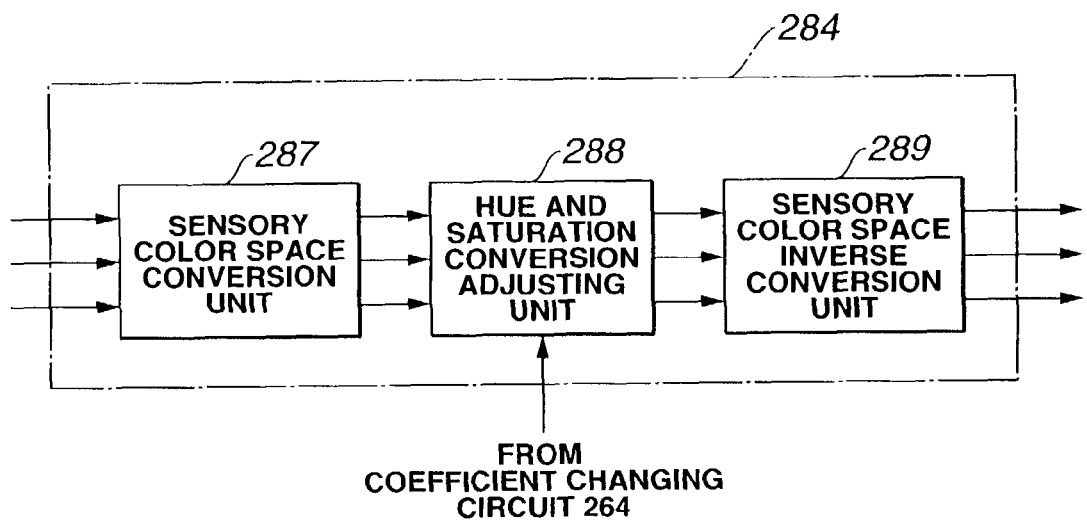
FIG. 77 is a configuration diagram illustrating the configuration of the color adjusting circuit shown in FIG. 75.
Figure 78:
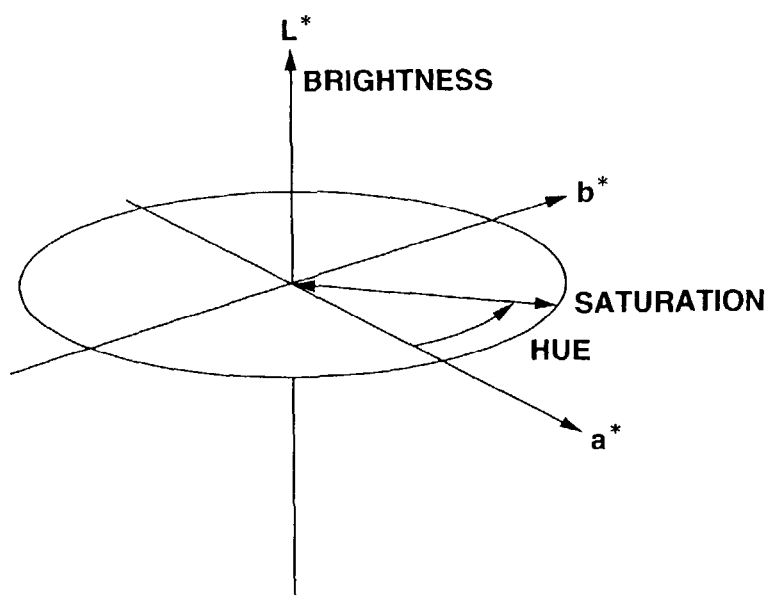
FIG. 78 is a diagram illustrating the concept of hue and saturation on a L*a*b* color space in the color adjusting circuit shown in FIG. 75.

FIG. 75 is a configuration diagram illustrating the configuration of an endoscope device, FIG. 76 is a configuration diagram illustrating the configuration of the image processing circuit shown in FIG. 75, FIG. 77 is a configuration diagram illustrating the configuration of the color adjusting circuit shown in FIG. 75, and FIG. 78 is a diagram illustrating the concept of hue and saturation on a L*a*b* color space in the color adjusting circuit shown in FIG. 75.

The eleventh embodiment is almost the same as the tenth embodiment, so only the differing points will be described, and the same configurations will be denoted with the same reference numerals and description thereof will be omitted.

With the present embodiment, a case including means for converting coordinates between a color space such as XYZ which is not dependent on a device such as a monitor, and a color space such as RGB which is dependent on a device, is shown as color conversion of a color conversion processing circuit for changing operations synchronously with operations of filter switching.

As shown in FIG. 75, a processing switch-over instructing switch 281 is provided in the electronic endoscope 203, with the image processing circuit 230 receiving control signals from the mode switch-over circuit 242 and instruction signals from the processing switch-over instructing switch 281, and performing the later-described color conversion processing.

As shown in FIG. 76, a color conversion processing circuit 230*b* configured in the image processing circuit 230 comprises LUTs 282a, 282b, and 282c, which are set for each band, a 3×3 matrix circuit 283, a color adjusting circuit 284, a subsequent stage 3×3 matrix circuit 285, subsequent LUTs 286a, 286b, and 286c, which are set for each band, and the coefficient changing circuit 264.

RGB data which is first input to the preliminary LUTs 282a, 282b, and 282c is subjected to inverse γ correction. This is to cancel non-linear γ correction which is performed taking into consideration the γ properties of the display device such as a CRT, before color conversion processing.

Next, conversion is made at the preliminary 3×3 matrix circuit 283, from RGB to XYZ which is a color space that is not device-dependent. The conversion expression is shown in Expression 4.

In Expression 4, xi, yi, and zi (i=R, G, B) are xy chromaticity coordinates of the primitive colors of the display device such as a CRT or the like.

Expression 4

$$\begin{pmatrix} X \\ Y \\ Z \end{pmatrix} = \begin{pmatrix} \frac{x_R}{y_r} & \frac{x_G}{y_G} & \frac{x_B}{y_B} \\ 1 & 1 & 1 \\ \frac{z_R}{y_R} & \frac{z_G}{y_G} & \frac{z_B}{y_B} \end{pmatrix} \begin{pmatrix} R \\ G \\ B \end{pmatrix} \quad (4)$$

Next, following being subjected to later-described appropriate color adjustment at the color adjusting circuit 284, conversion is made into device-dependent color space R'G'B' again at the subsequent stage 3×3 matrix circuit 285 by Expression 5, and following γ correction for monitor display at the subsequent LUTs, output is made to the observation monitor 205.

Expression 5

$$\begin{pmatrix} R' \\ G' \\ B' \end{pmatrix} = \begin{pmatrix} \frac{x_R}{y_r} & \frac{x_G}{y_G} & \frac{x_B}{y_B} \\ 1 & 1 & 1 \\ \frac{z_R}{y_R} & \frac{z_G}{y_G} & \frac{z_B}{y_B} \end{pmatrix}^{-1} \begin{pmatrix} (X)' \\ (Y)' \\ (Z)' \end{pmatrix} \quad (5)$$

Next, the operations of the color adjusting circuit 284 will be described. As shown in FIG. 77, the color adjusting circuit 284 comprises a sensory color space conversion unit 287 which performs conversion from XYZ to a sensory color space such as L*a*b*, a hue and saturation conversion adjusting unit 288 which performs conversion to hue and saturation which humans perceive to be the three attributes of color, adjusts these values and performs intuitive color adjustment, and then performs inverse conversion to L*a*b*, and a sensory color inverse conversion unit 289 for performing conversion to XYZ again.

Expression 6 shows the conversion expression between L*a*b* and XYZ, and further, Expression 7 shows the conversion expression from L*a*b* to hue Hab and Cab. Here, $X_w, Y_w,$ and $Z_w$ represent the XYZ values for reference white.

Expression 6

$$L^* = 116 \left(\frac{Y}{Y_w}\right)^{\frac{1}{3}} - 16 \quad (6)$$

$$a^* = 500 \left[\left(\frac{X}{X_w}\right)^{\frac{1}{3}} - \left(\frac{Y}{Y_w}\right)^{\frac{1}{3}}\right]$$

$$b^* = 200 \left[\left(\frac{X}{X_w}\right)^{\frac{1}{3}} - \left(\frac{Z}{Z_w}\right)^{\frac{1}{3}}\right]$$

Expression 7

$$C_{ab} = \sqrt{a^{*2} + b^{*2}} \quad (7)$$

$$H_{ab} = \arctan\left(\frac{b^*}{a^*}\right)$$

Also, FIG. 78 illustrates the concepts of hue and saturation in a L*a*b* color space.

Once converted into hue and saturation, color adjustment can be performed intuitively. For example, if a brighter color tone is desired, this can be achieved by multiplying or adding the saturation with a constant coefficient. Also, in the event that change of the color toward blue or toward red is desired, the hue value can be adjusted. Thus, intuitive color adjustment can be realized at the color adjusting means.

Next, operations interlocked with the mode switch-over circuit 242 and the processing switch-over instructing switch 281 will be described. A characteristic of observation with narrow-band RGB illustration light is that, in the event that there are different structures in the depth direction of the body, such as blood vessel structures, these are represented with different colors. Even more effective display can be made by enhancing the saturation and rotating the hue as suitable in order to enhance these characteristics even more.

Accordingly, being interlocked with the mode switch-over circuit 242, the coefficient changing circuit 264 changes the coefficients of the related circuit based on instruction signals from the processing switch-over instructing switch 281, so that through passage is allowed without color adjustment when performing normal observation for example, and color adjustment is made for narrow-band observation. Further, in the event of observation with narrow-band RGB illumination light, the degree of enhancement of saturation and the degree of rotation of hue is switched over according to user preferences, the type of subject, etc., by instructions of the processing switch-over instructing switch 281.

Also, the conversion from RGB to XYZ has been performed with an expression based on a normal CRT device model, but may be changed to the one as shown in Expression 8 with regard to a calculation method of the luminance Y, of XYZ.

In Expression 8, change has been made such that the RGB ratio can be specified at the time of calculating Y.

Expression 8

$$\begin{pmatrix} X \\ Y \\ Z \end{pmatrix} = \begin{pmatrix} \frac{x_R}{y_r} & \frac{x_G}{y_G} & \frac{x_B}{y_B} \\ \omega_R & \omega_G & \omega_B \\ \frac{z_R}{y_R} & \frac{z_G}{y_G} & \frac{z_B}{y_B} \end{pmatrix} \begin{pmatrix} R \\ G \\ B \end{pmatrix} \quad (8)$$

The B image of narrow-band RGB has a characteristic of minute structures of the body mucous membrane surface being reflected with high contrast. In order to reflect this information in the luminance information, the weight ωB of B is increased at the time of calculating Y. Generally, the luminance of B is low as compared to RG (G is the greatest for human luminance sensitivity), so calculating using Expression 6 with no change does not reflect the information of B very much. Accordingly, it is meaningful to adjust the weight of B as described above.

Each of the band images reflect different body structures with narrow-band RGB images, so the weight can be adjusted with Expression 8 according to objects of use. It is sufficient that multiple types of weight combinations be prepared beforehand, so as to be switched over under control of the processing switch-over switch. Incidentally, Expression 7 is used for inverse conversion from XYZ to RGB in this case.

Thus, with the present embodiment, as with the tenth embodiment, a representation method which takes advantage of the characteristic of permeation depth information of narrow-band RGB illumination light can be realized by setting the parameters of the color converting processing circuit 230a synchronously with the filter switching, and accordingly, tissue information at desired depths near the tissue surface of living body tissue can be separated and visually recognized.

Next, a twelfth embodiment of the present invention will be described with reference to FIG. 79 through FIG. 84.

Figure 79:
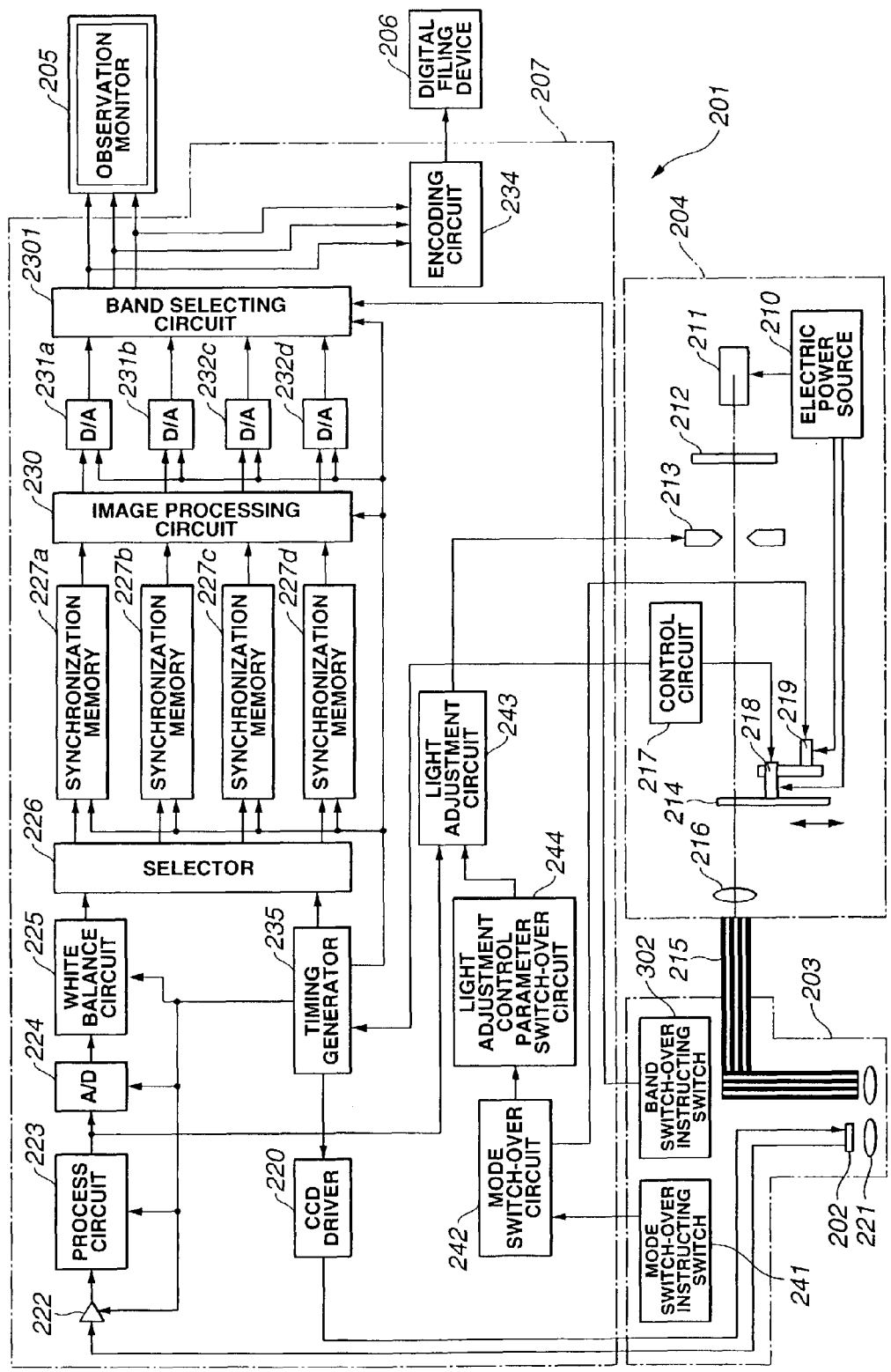
FIG. 79 is a configuration diagram illustrating the configuration of an endoscope device according to a twelfth embodiment of the present invention.
Figure 80:
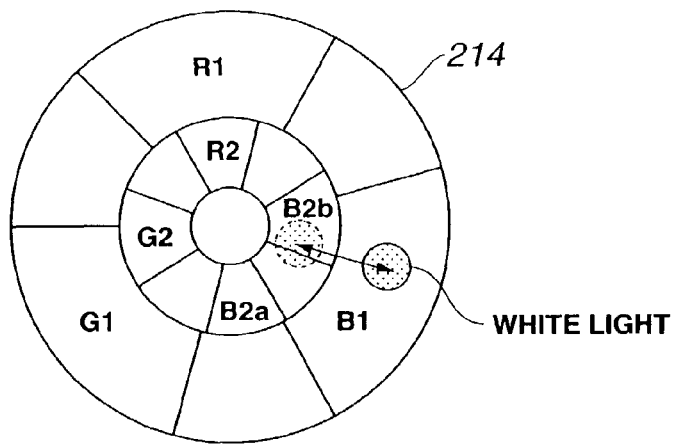
FIG. 80 is a configuration diagram illustrating the configuration of the rotating filter shown in FIG. 79.
Figure 81:
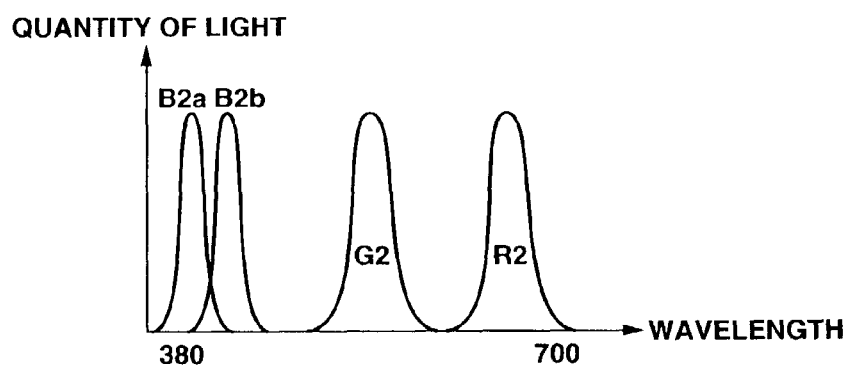
FIG. 81 is a diagram illustrating the spectral transmission properties of the filters G2, B2a, and B2b, of the rotating filter shown in FIG. 80.
Figure 82:
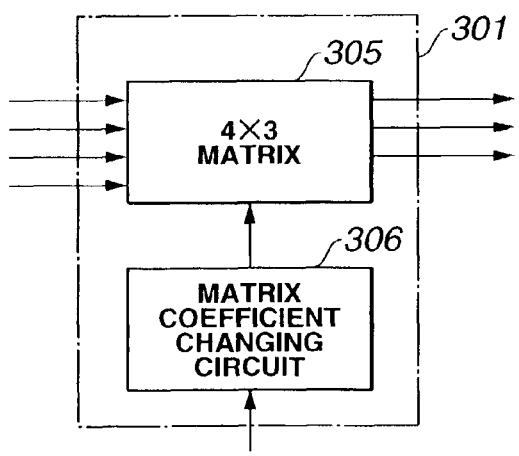
FIG. 82 is a configuration diagram illustrating the configuration of the band selecting circuit shown in FIG. 79.
Figure 83:
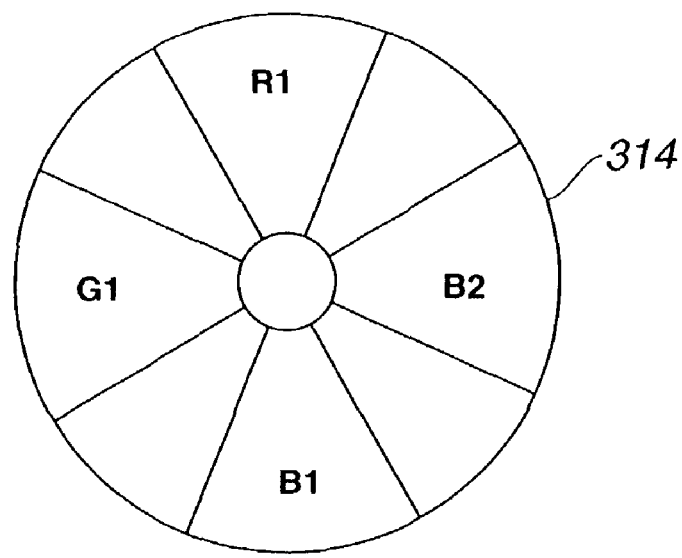
FIG. 83 is a configuration diagram illustrating the configuration of a modification made on the rotating filter shown in FIG. 79.
Figure 84:
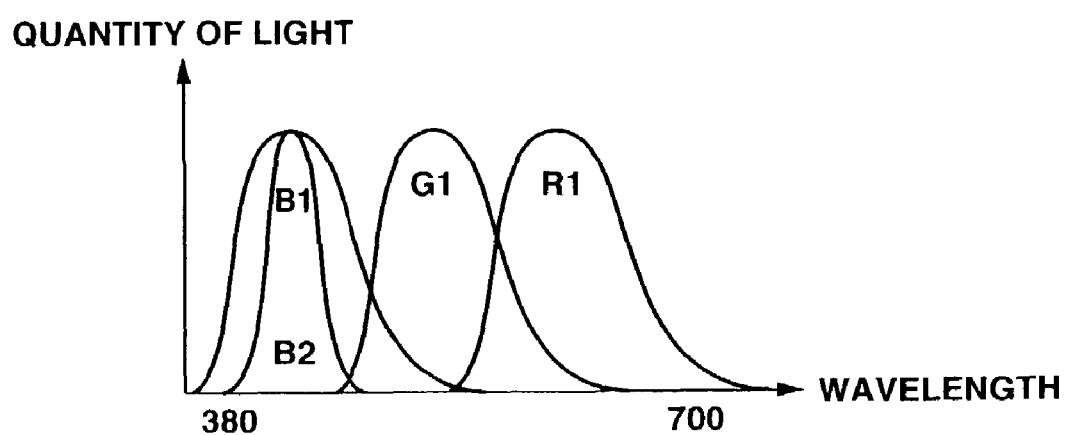
FIG. 84 is a diagram illustrating spectral transmission properties of the rotating filter shown in FIG. 83.

FIG. 79 is a configuration diagram illustrating the configuration of an endoscope device, FIG. 80 is a configuration diagram illustrating the configuration of the rotating filter shown in FIG. 79, FIG. 81 is a diagram illustrating the spectral transmission properties of the filters G2, B2a, and B2b, of the rotating filter shown in FIG. 80, FIG. 82 is a configuration diagram illustrating the configuration of the band selecting circuit shown in FIG. 79, FIG. 83 is a configuration diagram illustrating the configuration of a modification made on the rotating filter shown in FIG. 79, and FIG. 84 is a diagram illustrating spectral transmission properties of the rotating filter shown in FIG. 83.

The twelfth embodiment is almost the same as the tenth embodiment, so only the differing points will be described, and the same configurations will be denoted with the same reference numerals and description thereof will be omitted.

As shown in FIG. 79, the present embodiment comprises four pieces of synchronizing memory 227a, 227b, 227c, and 227d, for the output of a selector 226, the image processing circuit 230 which performs image processing with regard to the output of the four pieces of synchronizing memories 227a, 227b, 227c, and 227d, D/A circuits 231a, 231b, 231c, and 231d, which convert the four sets of data processed by the image processing circuit 230 into analog data, and a band selecting circuit for subjecting the output of the D/A circuits 231a, 231b, 231c, and 231d to matrix computation and outputting as three bands of data.

The reason that there are four sets of synchronizing memory is that the second filter set of the double-structure rotating filter 214 is configured of filters with four band-widths, R2, G2, B2a, and B2b as shown in FIG. 80, and the spectral transmittance properties of these filters R2, G2, B2a, and B2b are as shown in FIG. 81.

In the event that the rotating filter 214 is specified to the second filter set (R2, G2, B2a, and B2b) by control signals of the mode switch-over circuit 242 by control signals from the mode switch-over instructing switch 241, the four band images are input to the four pieces of synchronizing memories 227a, 227b, 227c, and 227d. The four band images are subjected to processing such as color adjustment and the like at the image processing circuit 230, then subjected to D/A conversion at the D/A circuits 231a, 231b, 231c, and 231d, and then input to a band selecting circuit 301.

The user uses a band switch-over instructing switch 302 provided on the operating unit of the electronic endoscope 203 to specify which band of the four bands will be used to output an image to the observation monitor 205.

As shown in FIG. 82, the band selecting circuit 301 is configured of a 4×3 matrix circuit 305 and a matrix coefficient changing circuit 306, wherein band switch-over instructing signals output from the band switch-over instructing switch 302 are input to the matrix coefficient changing circuit 306 provided to the band selecting circuit 301. The matrix coefficient changing circuit 306 applies predetermined matrix coefficients to the 4×3 matrix circuit 305, based on the band switch-over instructing signals.

Expression 9 shows a matrix circuit expression.

Expression 9

$$\begin{pmatrix} d_r \\ d_g \\ d_b \end{pmatrix} = \begin{pmatrix} w_{11} & w_{12} & w_{13} & w_{14} \\ w_{21} & w_{22} & w_{23} & w_{24} \\ w_{31} & w_{32} & w_{33} & w_{34} \end{pmatrix} \begin{pmatrix} D_{R2} \\ D_{G2} \\ D_{B2a} \\ D_{B2b} \end{pmatrix} \quad (9)$$

As shown in FIG. 9, at the band selecting circuit 301, the 4×3 matrix coefficients act upon the input values for the four band images (DR2, DG2, DB2a, and DB2b) to yield three output signals (dr, dg, and db), and these signals are output to the observation monitor 205 as trichromatic signals.

Expression 10 illustrates an example of matrix coefficients.

Expression 10

$$M1 = \begin{pmatrix} 1 & 0 & 0 & 0 \\ 0 & 1 & 0 & 0 \\ 0 & 0 & 1 & 0 \end{pmatrix} \quad M2 = \begin{pmatrix} 1 & 0 & 0 & 0 \\ 0 & 1 & 0 & 0 \\ 0 & 0 & 0 & 1 \end{pmatrix} \quad M3 = \begin{pmatrix} 0 & 0 & 1 & 0 \\ 0 & 0 & 1 & 0 \\ 0 & 0 & 0 & 1 \end{pmatrix} \quad (10)$$

$$M4 = \begin{pmatrix} 0 & 0 & 1 & 0 \\ 0 & 0 & 1 & 0 \\ 0 & 0 & 1 & 0 \end{pmatrix} \quad M5 = \begin{pmatrix} 1 & 0 & 0 & 0 \\ 0 & 1 & 0 & 0 \\ 0 & 0 & 0.2 & 0.8 \end{pmatrix}$$

The coefficients set in M1 configure an image of R2, G2, and B2a, while M2 is settings using B2b instead of B2a. Switching between M1 and M2 can be made by, for example, setting B2a at a center wavelength of near-ultraviolet light, and setting B2b to a hemoglobin absorbing wavelength band (e.g., 415 nm), thereby enabling using these as depending on conditions, as a mode for observing minute irregularities near the surface of the mucous membranes such as pit patterns in detail in the event that M1 is applied, and a mode for observing in detail minute capillary networks near the surface of the mucous membranes in the event that M2 is applied.

Also, the coefficient M3, because the image is configured of the two bands of B2a and B2b, is suitable for catching change in scattering properties such as change in the cell structure near the surface of the mucous membranes and the like, by configuring a narrow-band filter with B2a and B2b in close approximation near 380 nm.

Also, in the event that simple observation of a single-color image of a certain band as a monochrome image is desired, the settings may be made as with M4, or the coefficients may be set as in M5 to mix and output multiple bands at a certain ratio so as to take advantage of the properties of each band.

Thus, according to the present embodiment, in addition to the advantages of the tenth embodiment, there are no markedly dark portions on the screen at the time of changing filters to switch over from normal observation to narrow-band filter observation, and light quantity sufficient to fully enable observation can be obtained. Further, which band to use for image observation can be selected from the multiple filters, so optimal observation images according to the state of usage can be obtained.

Also, though the present embodiment describes the rotating filter 214 as being a double structure, the rotating filter can be made a single structure in the event that changing the B filter is sufficient for obtaining image effects, thus configuring a rotating filter 214 made up of four filters, as shown in FIG. 83. As for the filter properties, there is a configuration wherein, for example, only the B filter is made narrow-band, as shown in FIG. 84. The object of this is to take advantage of the fact that the permeation depth of light around this wavelength band to the body is shallow, thereby improving contrast of body structures such as blood vessels near the surface by the filter which narrows the band. Due to such a configuration for the rotating filter 214, the user can obtain optimal observation images by simply instructing band switching over according to the state of observation, without switching filters.

As described above, according to the tenth embodiment through twelfth embodiment, tissue information at a desired depth near the tissue surface of the living body tissue can be separated and visually recognized.

Next, a thirteenth embodiment of the present invention will be described with reference to FIG. 85 through FIG. 94.

Figure 85:
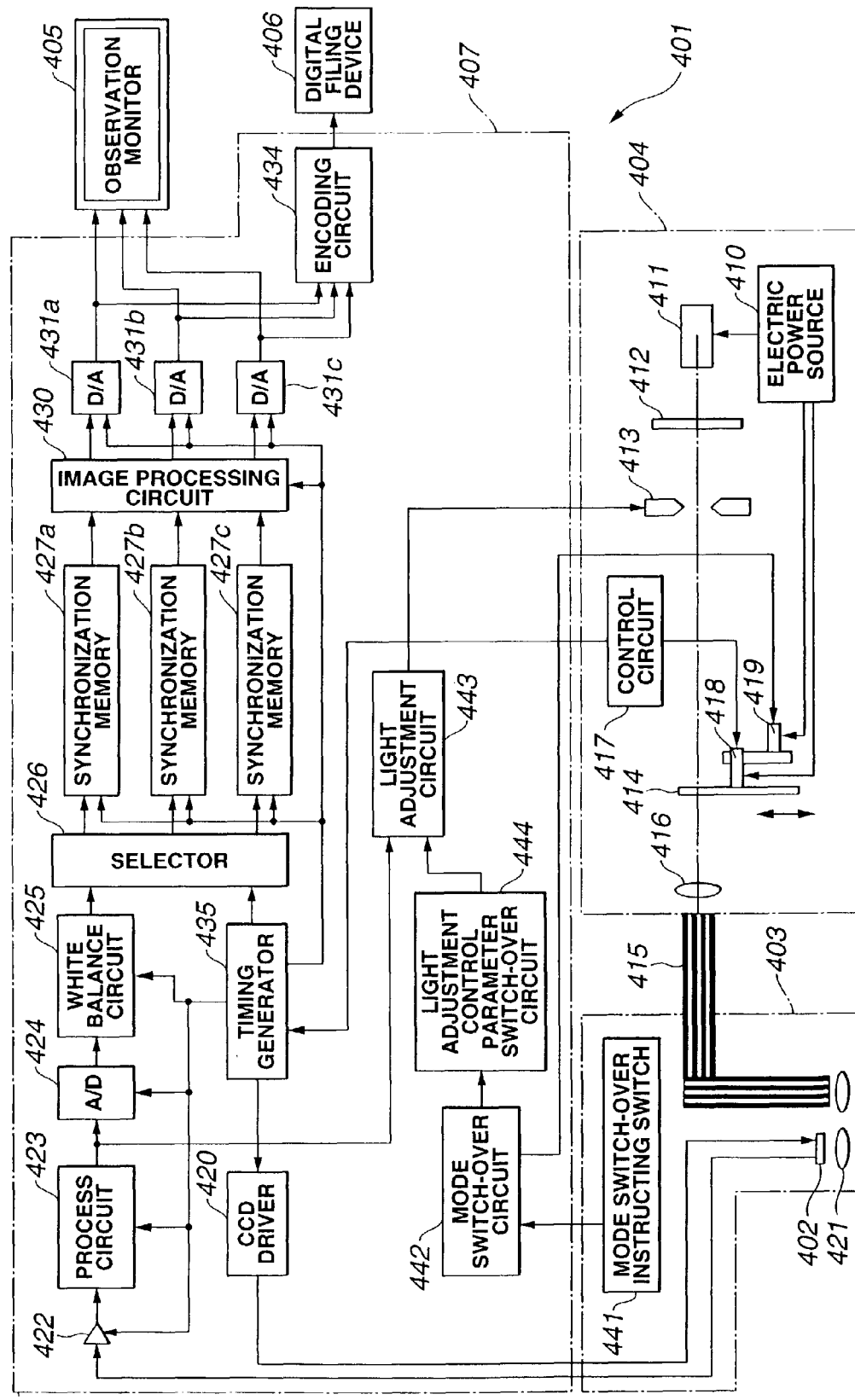
FIG. 85 is a configuration diagram illustrating the configuration of an endoscope device according to a thirteenth embodiment of the present invention.
Figure 86:
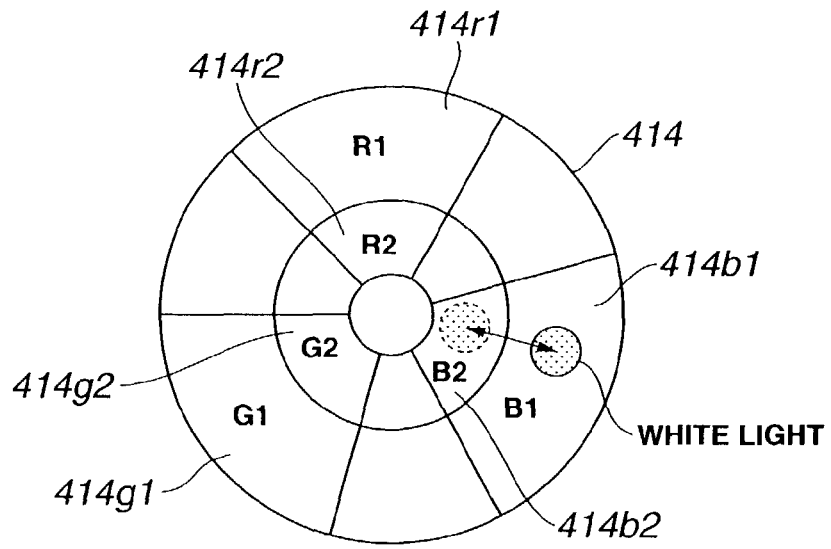
FIG. 86 is a configuration diagram illustrating the configuration of the rotating filter shown in FIG. 85.
Figure 87:
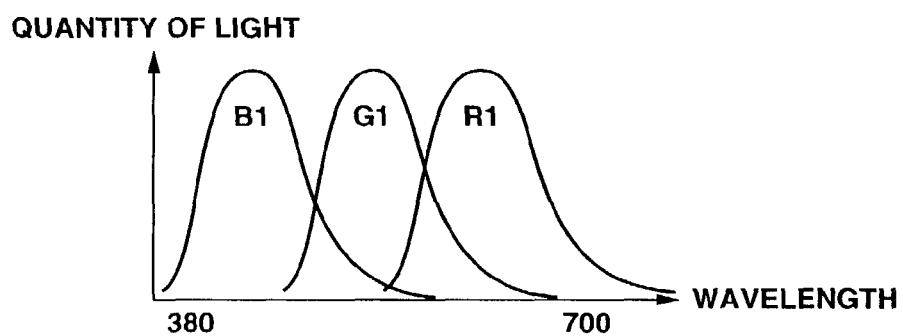
FIG. 87 is a diagram illustrating the spectral properties of the first filter set of the rotating filter shown in FIG. 86.
Figure 88:
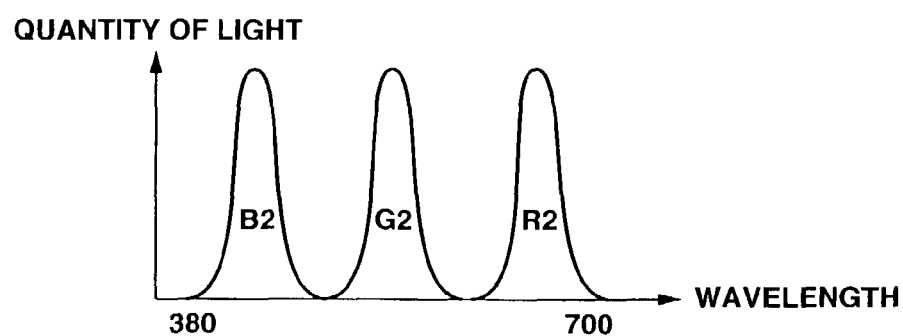
FIG. 88 is a diagram illustrating the spectral properties of the second filter set of the rotating filter shown in FIG. 86.
Figure 89:
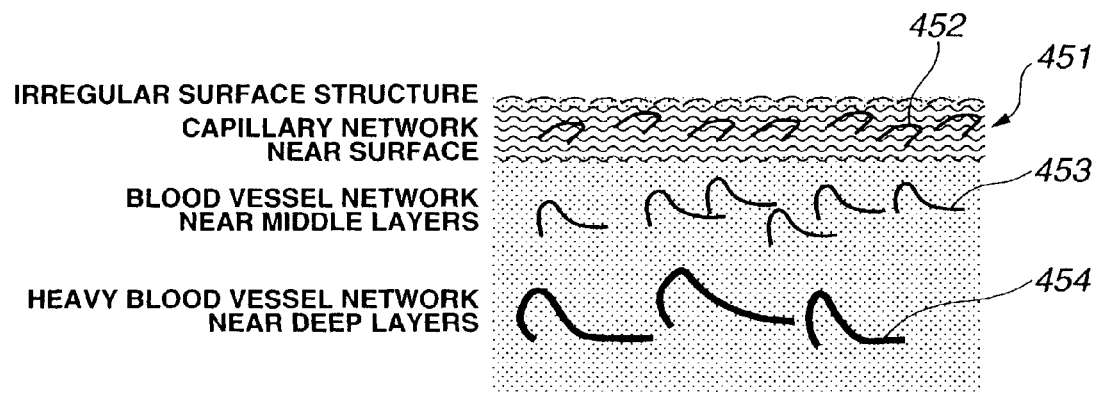
FIG. 89 is a diagram illustrating the structure of the living body tissue in the layer direction to be observed with the endoscope device shown in FIG. 85.
Figure 90:
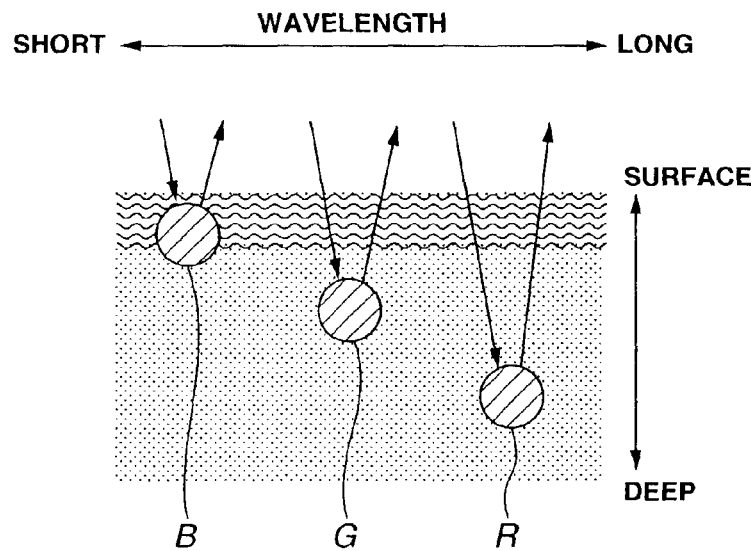
FIG. 90 is a diagram describing the state of the illumination light from the endoscope device shown in FIG. 85 reaching the living body tissue in the layer direction.
Figure 91A:
FIGS. 91a-c are diagrams illustrating each of the band images from frame sequence light transmitted through the first filter set shown in FIG. 87.
Figure 91B:
Figure 91C:
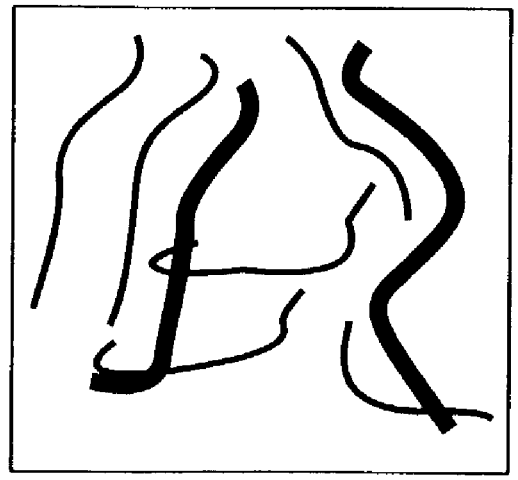
Figure 92A:
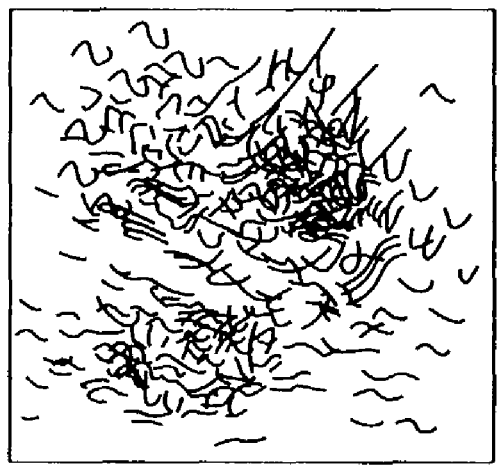
FIGS. 92a-c are diagrams illustrating each of the band images from frame sequence light transmitted through the second filter set shown in FIG. 88.
Figure 92B:
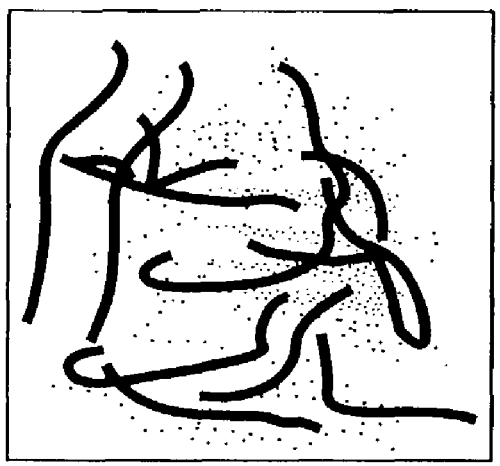
Figure 92C:
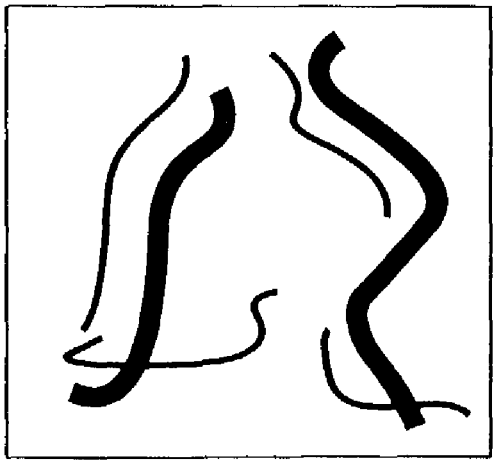
Figure 93:
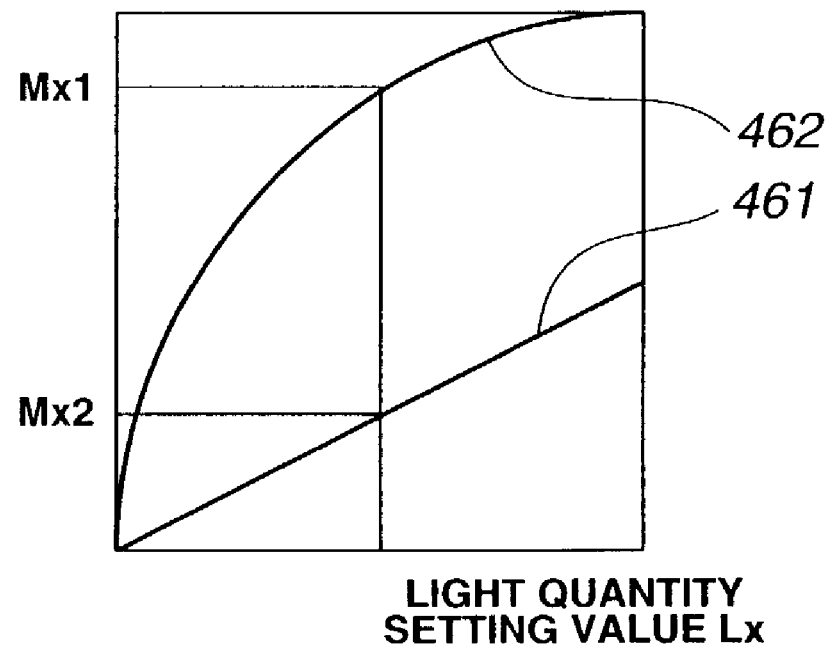
FIG. 93 is a diagram describing light adjustment control performed by a light adjusting circuit shown in FIG. 85.
Figure 94:
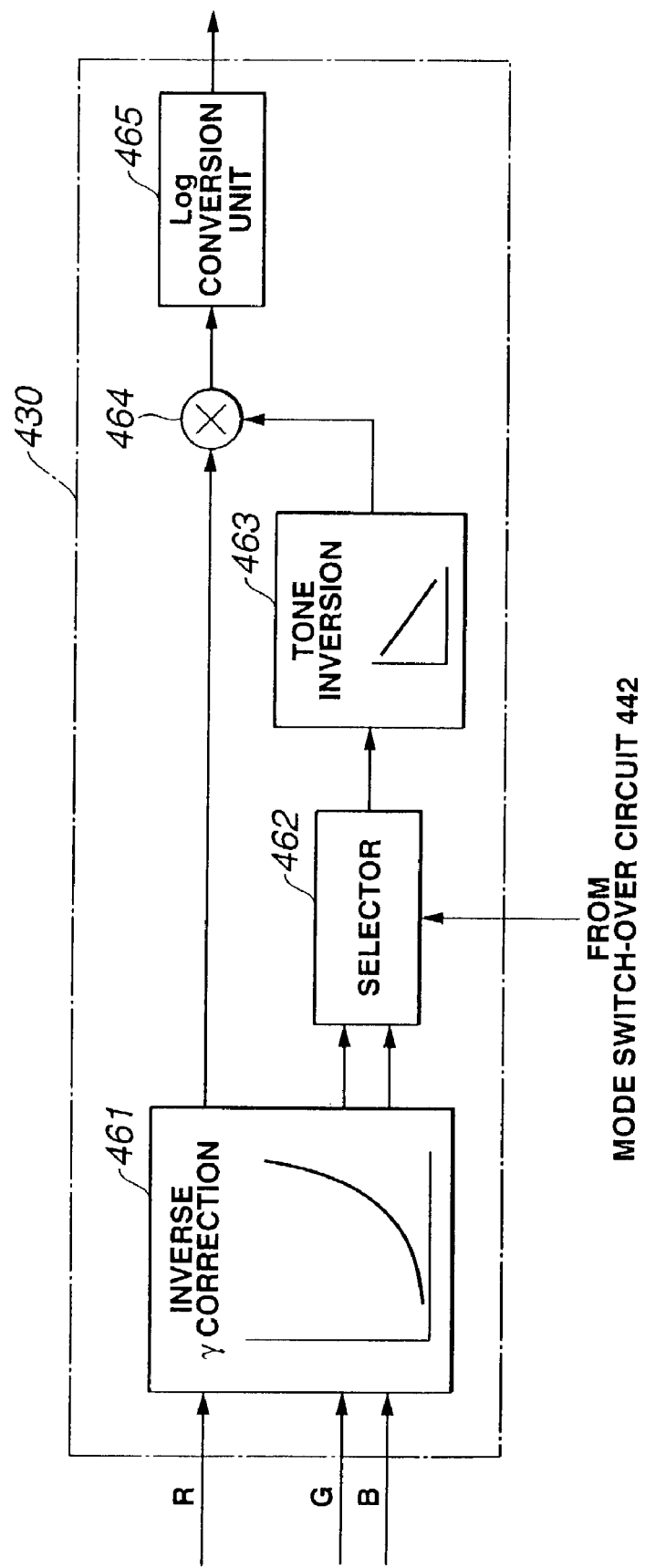
FIG. 94 is a configuration diagram illustrating the configuration of the image processing circuit shown in FIG. 85.

FIG. 85 is a configuration diagram illustrating the configuration of an endoscope device according to the present invention, FIG. 86 is a configuration diagram illustrating the configuration of the rotating filter shown in FIG. 85, FIG. 87 is a diagram illustrating the spectral properties of the first filter set of the rotating filter shown in FIG. 86, FIG. 88 is a diagram illustrating the spectral properties of the second filter set of the rotating filter shown in FIG. 86, FIG. 89 is a diagram illustrating the structure of the living body tissue in the layer direction to be observed with the endoscope device shown in FIG. 85, FIG. 90 is a diagram describing the state of the illumination light from the endoscope device shown in FIG. 85 reaching the living body tissue in the layer direction, FIG. 91 is a diagram illustrating each of the band images from frame sequence light transmitted through the first filter set shown in FIG. 87, FIG. 92 is a diagram illustrating each of the band images from frame sequence light transmitted through the second filter set shown in FIG. 88, FIG. 93 is a diagram describing light adjustment control performed by a light adjusting circuit shown in FIG. 85, and FIG. 94 is a configuration diagram illustrating the configuration of the image processing circuit shown in FIG. 85.

The thirteenth embodiment is almost the same as the tenth embodiment, so only the differing points will be described, and the same configurations will be denoted with the same reference numerals and description thereof will be omitted.

As shown in FIG. 85, the endoscope device 401 according to the present embodiment is configured of an electronic endoscope 403 which is inserted inside the body cavity and which has a CCD 402 serving as image-pickup means for capturing images of tissue within the body cavity, a light source device 404 for supplying illumination light to the electronic endoscope 403, and a video processor 407 for subjecting image-pickup signals from the CCD 402 of the electronic endoscope 403 to signal processing and displaying endoscopic images on an observation monitor 405 or encoding the endoscopic images and outputting to an image filing device 406 as compressed images.

The light source device 404 is configured of a xenon lamp 411 for emitting illumination light, a heat ray cut filter 412 for shielding heat rays from the white light, a diaphragm device 413 for controlling the light quantity of the white light through the heat ray cut filter 412, a rotating filter 414 for turning the illumination light into frame sequence light, a condenser lens 16 for collecting the frame sequence light coming through the rotating filter 414 onto the incident face of a light guide 15 disposed within the electronic endoscope 403, and a control circuit 17 for controlling the rotation of the rotating filter 414.

As shown in FIG. 86, the rotating filter 414 is formed in a disk-like shape and has a double structure with the center as the rotating axis, wherein an R1 filter 414r1, a G1 filter 414g1, and a B1 filter 414b1 making up a first filter set for outputting frame sequence light having overlapped spectral properties suitable for natural color reproduction such as indicated in FIG. 87 are situated on the outer sector, and wherein an R2 filter 414r2, a G2 filter 414g2, and a B2 filter 414b2 making up a second filter set for outputting narrow-band frame sequence light having discrete spectral properties enabling extraction of desired deep tissue information such as indicated in FIG. 88 are situated on the inner sector. As shown in FIG. 85, the rotating filter 414 is rotated by the control circuit 417 performing driving control of the rotating filter motor 418, and movement in the radial direction (movement which is perpendicular to the optical path of the rotating filter 414, which is selectively moving the first filter set or second filter set of the rotating filter 414 onto the optical path) is performed by the mode switch-over motor 19 by control signals from the mode switch-over circuit 442 within the later-described video processor 417.

Note that electric power is applied to the xenon lamp 411, diaphragm device 413, rotating filter motor 418, and mode switch-over motor 419, from the electric power supply unit 410.

Returning to FIG. 85, the video processor 407 is configured comprising a CCD driving circuit 420 for driving the CCD 402, an amplifier 422 for amplifying image-pickup signals by which images are captured of the body cavity tissue via the CCD 402 through the objective optical system 421, a process circuit 423 for performing correlated double sampling and noise reduction and so forth, with regard to image-pickup signals coming through the amplifier 422, an A/D converter 424 for converting the image-pickup signals passing through the process circuit 423 into image data of digital signals, a white balance circuit 425 for subjecting the image data from the A/D converter 424 to white balance processing, a selector 426 and synchronizing memories 427a, 427b, and 427c, for synchronizing the frame sequence light from the rotating filter 414, an image processing circuit 430 for reading out each set of image data of the frame sequence light stored in the synchronizing memories 427a, 427b, 427c, and subjecting these to gamma correction processing, outline enhancement processing, color processing, etc., D/A circuits 431a, 431b, and 431c, for converting the image data from the image processing circuit 430 into analog signals, an encoding circuit 434 encoding the output of the D/A circuits 431a, 431b, and 431c, and a timing generator 435 for inputting synchronizing signals synchronized with the rotation of the rotating filter 414 from the control circuit 417 of the light source device 404, and outputting various types of timing signals to the above-described circuits.

Also, a mode switch-over switch 441 is provided in the electronic endoscope 403, with the output of this switch-over switch 441 being output to a mode switch-over circuit 442 within the video processor 407. The mode switch-over circuit 442 of the video processor 407 outputs control signals to a light adjusting circuit 443, a light adjustment control parameter switch-over circuit 444, and mode switch-over motor 419 of the light source 404. The light adjustment control parameter switch-over circuit 444 outputs light adjustment control parameters corresponding to the first filter set or second filter set of the rotating filter 414 to the light adjusting circuit 443, and the light adjusting circuit 443 controls the diaphragm device 413 of the light source device 404 based on the control signals from the mode switch-over circuit 442 and light adjusting parameters from the light adjustment control parameter switch-over circuit 444, so as to perform appropriate brightness control.

As shown in FIG. 89, body cavity tissue 451 often has a structure wherein there is a distribution of different absorbent material such as blood vessels in the depth direction, for example. A great number of capillaries 452 are mainly distributed near the surface of mucus membranes, blood vessels 453 which are thicker than the capillaries are also distributed along with capillaries at the middle layer which is deeper than this layer, and even thicker blood vessels 454 are distributed at even deeper layers.

On the other hand, the permeation depth of the light in the depth direction as to the body cavity tissue 451 is dependent on the wavelength of light, and with illumination light containing the visible region, as shown in FIG. 90, in the case of light with a short wavelength such as blue (B), the light only reaches around the surface layer due to the absorption properties and scattering properties at the living body tissue, being subjected to absorption and scattering within the range up to that depth, and light coming out from the surface is observed. Also, in the case of green (G) light with a wavelength longer than that of blue (B) light, the light reaches a depth deeper than the range where the blue (B) light reaches, is subjected to absorption and scattering within the range at that depth, and light coming out from the surface is observed. Further, red (R) light with a wavelength longer than that of green (G) light, reaches a range even deeper.

At the time of performing normal observation, the mode switch-over motor 419 is controlled by the mode switch-over circuit within the video processor 407 with control signals, so that the R1 filter 414r1, G1 filter 414g1, and B1 filter 414b1, making up the first filter set of the rotating filter 414, are positioned on the optical path of the illumination light.

With the R1 filter 414r1, G1 filter 414g1, and B1 filter 414b, the wavelength regions are each overlapped as shown in FIG. 87, so at the time of normal observation of the body cavity tissue 451, a band image having shallow layer and middle layer tissue information containing a great amount of tissue information at the shallow layer such shown in "a" in FIG. 91 is captured in the image-pickup signals taken by the CCD 402 with the B1 filter 414b1, a band image having shallow layer and middle layer tissue information containing a great amount of tissue information at the middle layer such as shown in "b" in FIG. 91 is captured in the image-pickup signals taken by the CCD 402 with the G1 filter 414g1, and further, a band image having middle layer and deep layer tissue information containing a great amount of tissue information at the deep layer such shown in "c" in FIG. 91 is captured in the image-pickup signals taken by the CCD 402 with the R1 filter 414r1.

These RGB image-pickup signals are synchronized with the video processor 407 and subjected to signal processing, thus enabling an endoscopic image with desired or natural color reproduction to be obtained as an endoscopic image.

On the other hand, upon the mode switch-over switch 441 of the electronic endoscope 403 being pressed, the signals thereof are input to the mode switch-over circuit 442 of the video processor 407. The mode switch-over circuit 442 outputs control signals to the mode switch-over motor 419 of the light source device 404, thereby moving the first filter set of the rotating filter 414 that was on the optical path at the time of normal observation, and drives the rotating filter 414 with regard to the optical path so that the second filter set is positioned upon the optical path.

In the event of performing narrow-band light observation of the body cavity tissue 451 with the second filter set, the R2 filter 414r2, G2 filter 414g2, and B2 filter 414b2 make the illumination light to be narrow-band frame sequence light with discrete spectral properties as shown in FIG. 88, so a band image having tissue information at a shallow layer such as shown in "a" in FIG. 92 is captured in the image-pickup signals taken by the CCD 402 with the B2 filter 414b2, a band image having tissue information at the middle layer such as shown in "b" in FIG. 92 is captured in the image-pickup signals taken by the CCD 402 with the G2 filter 414g2, and a band image having tissue information at the deep layer such as shown in "c" in FIG. 92 is captured in the image-pickup signals taken by the CCD 402 with the R2 filter 414r2.

As can be clearly understood from FIG. 87 and FIG. 88, at this time, the quantity of transmitted light from the second filter set is less than the quantity of transmitted light from the first filter set, since the bands thereof are narrowed, so the light adjusting circuit 443 controls the diaphragm device 413 by the light adjustment control parameter switch-over circuit 444 outputting light adjustment control parameters according to the first filter set or second filter set of the rotating filter 414 to the light adjusting circuit 443, thereby, as shown in FIG. 93, controlling the diaphragm device 413 when making narrow-band light observation so as to control light quantity Mx with a diaphragm control curve 462 corresponding to a set value Lx, as to, for example, a linear diaphragm control line 461 by the diaphragm device 413 in normal observation, corresponding to the set value Lx on an unshown setting panel of the video processor 407.

Specifically, the aperture level value corresponding to the light quantity setting value Lx changes from Mx1 to Mx2 as shown in FIG. 93, in a manner synchronous with changing the first filter set to the second filter set, and consequently, the diaphragm is controlled in the direction of being opened, and acts to compensate for reduction in the quantity of illumination light by narrowing the bands of the filters.

The image processing circuit 430 of the present embodiment has a processing structure for calculating IHb (hemoglobin index) which is a value correlated with the hemoglobin concentration in blood, using two of the band image information from RGB, and specifically, as shown in FIG. 94, RGB signals input to the image processing circuit 430 are subjected to inverse γ correction processing for removing the γ correction performed for CRT display at the inverse γ correction processing unit 461, with table conversion or the like.

Next, with regard to the GB signals subjected to inverse γ correction, signals to be sent to the subsequent processing are selected based on control signals from the mode switch-over circuit 442 with the selector unit 462. Next, following tone inversion processing at a tone inversion processing unit 463, multiplication with an R signal is performed at the multiplier 464. Finally, after being subjected to logarithmic transformation at a logarithmic transformation unit 465, output is made from the image processing circuit 430.

As for the output format from the image processing circuit 430, pseudo color images may be generated based on the IHb, or one band image, e.g., the R image may be substituted for the IHb image.

With conventional IHb, an expression of 32×Log 2(R/G) is being used. This expression takes advantage of the fact that the G band image reflects intensely blood information.

On the other hand, narrow-banding of the filter reflects intensely surface capillaries to the B image. Accordingly, the B and G images following filter switching differ in depth where the blood vessels exist, so B reflects information of the surface layer, and G reflects layer positions deeper than that.

Accordingly, with the present embodiment, upon the mode switch-over switch 441 being pressed and the mode entering the narrow-band observation mode, the IHb value (32×Log 2(R/B)) of the surface layer of the mucous membrane based on B information, and the IHb value (32×Log 2(R/G)) of the middle layer of the mucous membrane based on G information can be switched between and used by switching over the operations of the selector unit 462 shown in FIG. 94, so tissue information at a desired depth near the tissue surface of the living body tissue can be separated and visually recognized.

Now, while the operations of the selector unit 462 have been described as being based on control signals from the mode switch-over circuit 442, a separate switch may be provided on the operating unit or the like of the electronic endoscope 403.

Next, a fourteenth embodiment of the present invention will be described with reference to FIG. 95 through FIG. 99.

Figure 95:
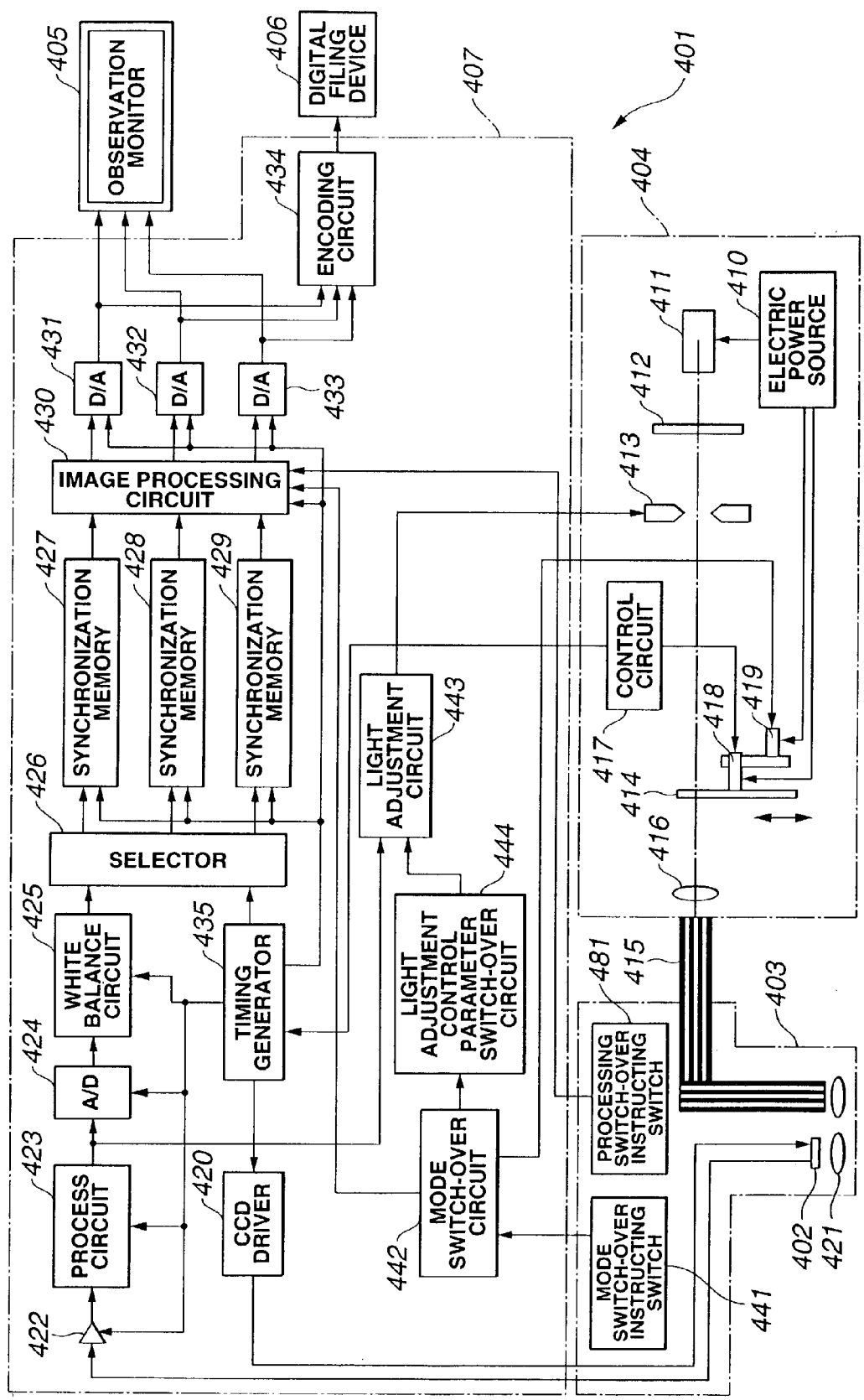
FIG. 95 is a configuration diagram illustrating the configuration of an endoscope device according to a fourteenth embodiment of the present invention.
Figure 96:
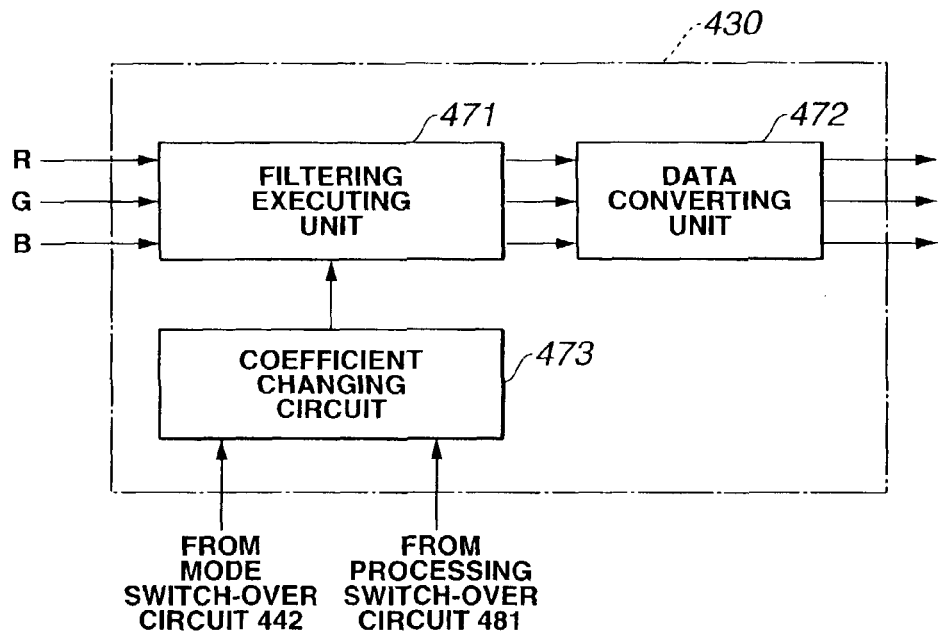
FIG. 96 is a configuration diagram illustrating the configuration of the image processing circuit shown in FIG. 95.
Figure 97:
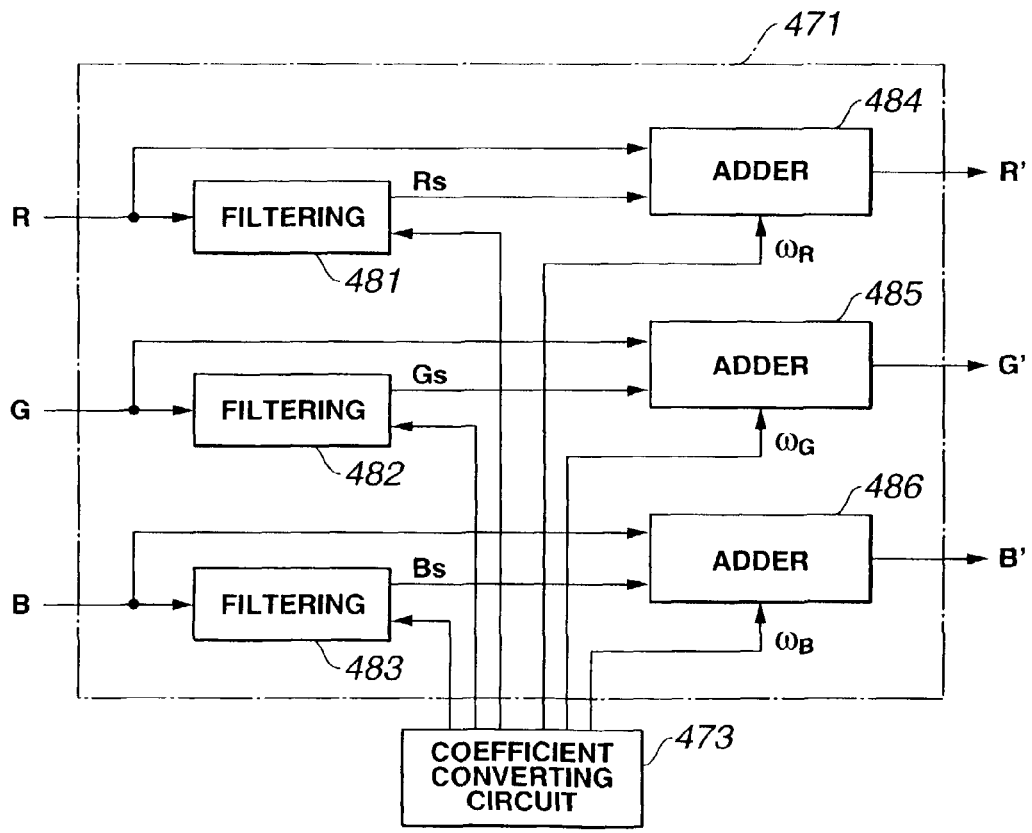
FIG. 97 is a configuration diagram illustrating the configuration of the filtering execution unit shown in FIG. 96.
Figure 98:
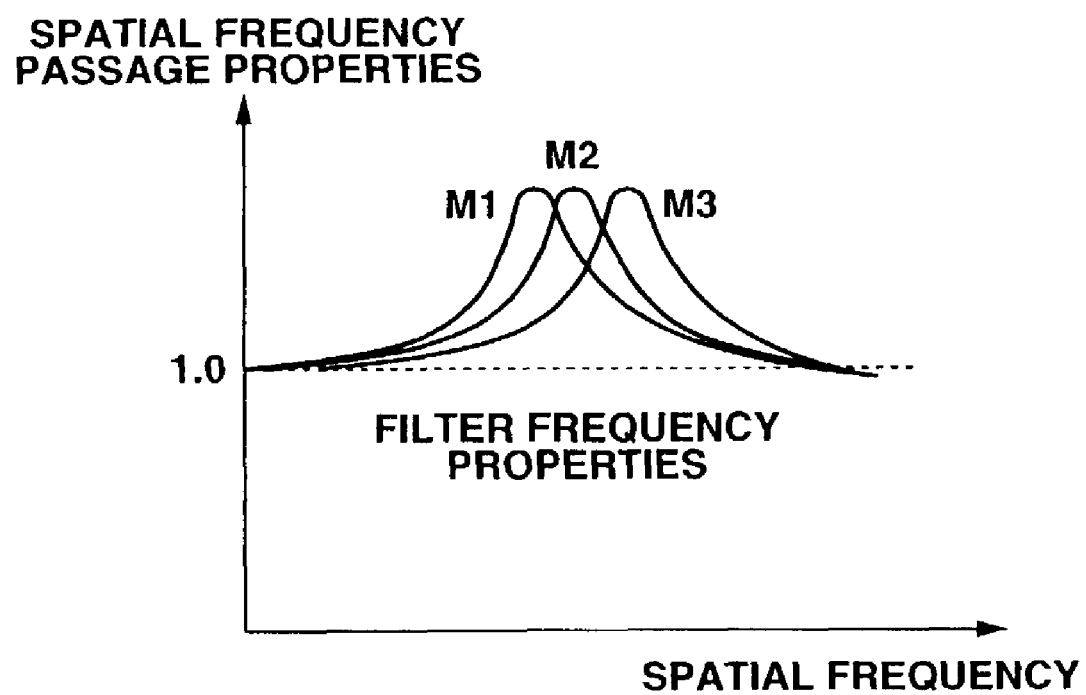
FIG. 98 is a diagram illustrating the filter frequency properties of the filtering execution unit shown in FIG. 97.

FIG. 95 is a configuration diagram illustrating the configuration of an endoscope device, FIG. 96 is a configuration diagram illustrating the configuration of the image processing circuit shown in FIG. 95, FIG. 97 is a configuration diagram illustrating the configuration of the filtering execution unit shown in FIG. 96, FIG. 98 is a diagram illustrating the filter frequency properties of the filtering execution unit shown in FIG. 97, and FIG. 99 is a diagram illustrating RGB images taken when in the narrow-band observation mode in FIG. 95.

The fourteenth embodiment is almost the same as the thirteenth embodiment, so only the differing points will be described, and the same configurations will be denoted with the same reference numerals and description thereof will be omitted.

The present embodiment relates to an endoscope which is capable of switching the spectral properties of illumination light to narrow-band RGB properties, and which has, being interlocked therewith, functions for changing light quantity control parameters such as light adjustment tables, and for changing image processing parameters.

As shown in FIG. 95, a processing switch-over instructing switch 470 is provided for the electronic endoscope 403, and the image processing circuit 430 receives control signals form the mode switch-over circuit 442 and instruction signals from the processing switch-over instructing switch 470, and performs the later-described color conversion processing.

Conventionally, spatial frequency filters such as FIR filters have been used for image quality improvement and image enhancement processing in endoscopic image processing, and have been effective in assisting in observation.

The image processing circuit 430 according to the present embodiment is of a configuration wherein this spatial frequency filtering is applied to narrow-band RGB images, and as shown in FIG. 96, is configured of a filtering execution FIG. 471 for performing spatial frequency filtering processing with regard to input RGB images, a data converting unit 472 for performing conversion of the output results of the filtering execution FIG. 471 such as adjusting each of RGB to within an 8-bit level, and a coefficient converting unit 473 for changing the operations of the filtering execution unit based on control signals from the filter switch-over circuit 442 and instruction signals from the processing switch-over instructing switch 470.

As shown in FIG. 97, the filtering execution FIG. 471 is made up of filtering units 481, 482, and 483, which perform 5×5 mask computation with regard to each of the RGB image data, and adders 484, 485, and 486 which perform weighting on the output of the filtering units 481, 482, and 483 and add to each of the RGB image data, wherein the coefficient changing unit 473 sets mask coefficients to the filtering units 481, 482, and 483 and weight coefficients to the adders 484, 485, and 486.

Accordingly, by performing computation such as shown in Expression 11, wherein the image data is represented by R(x, y), G(x, y), B(x, y), the output of the filtering units 481, 482, and 483 by Rs(x, y), Gs(x, y), Bs(x, y), and the weight coefficients by ωR, ωG, and ωB, spatial frequency filtering processing results R'(x, y), G'(x, y), and B'(x, y) with the filter frequency properties such as shown in FIG. 98 for example, are output.

Expression 11

$$R'(x,y)=R(x,y)+\omega R \cdot Rs(x,y) \quad G'(x,y)=G(x,y)+\omega G \cdot Gs(x,y)$$
$$B'(x,y)=B(x,y)+\omega B \cdot Bs(x,y) \tag{11}$$

The filter properties shown in FIG. 98 are properties which, while suppressing enhancement of noise components as much as possible in the order of M1, M2, and M3, enhance the high-frequency components, and the enhanced bands are shifted to high frequencies in order. Such filters with different enhanced bands are each individually applied to respective bands.

That is to say, as shown in FIG. 99, upon the mode switch-over switch 441 being pressed to enter the narrow-band observation mode, the B image has smaller blood vessel patterns than the R image, i.e., higher frequency properties, and M3 is applied rather than filter M1 in order to reproduce these patterns more clearly. The R image is contrary, and application of M1 is more suitable than M3. Thus, it is important to use the filter properties according to the contents of the body information which the bands reproduce.

Also, such filter properties are effective for narrow-band RGB images, and separate filter properties are required for normal observation. Accordingly, the coefficient changing unit 473 changes the filter properties to those which are optimal according to the mode switch-over circuit 442. Control by instruction signals from the processing switch-over instructing switch 470 performs adjustment of enhancement level and so forth, for example.

Thus, according to the present embodiment as well, tissue information at a desired depth near the tissue surface of the living body tissue can be separated and visually recognized.

Next, a fifteenth embodiment of the present invention will be described with reference to FIG. 100 through FIG. 103.

Figure 100:
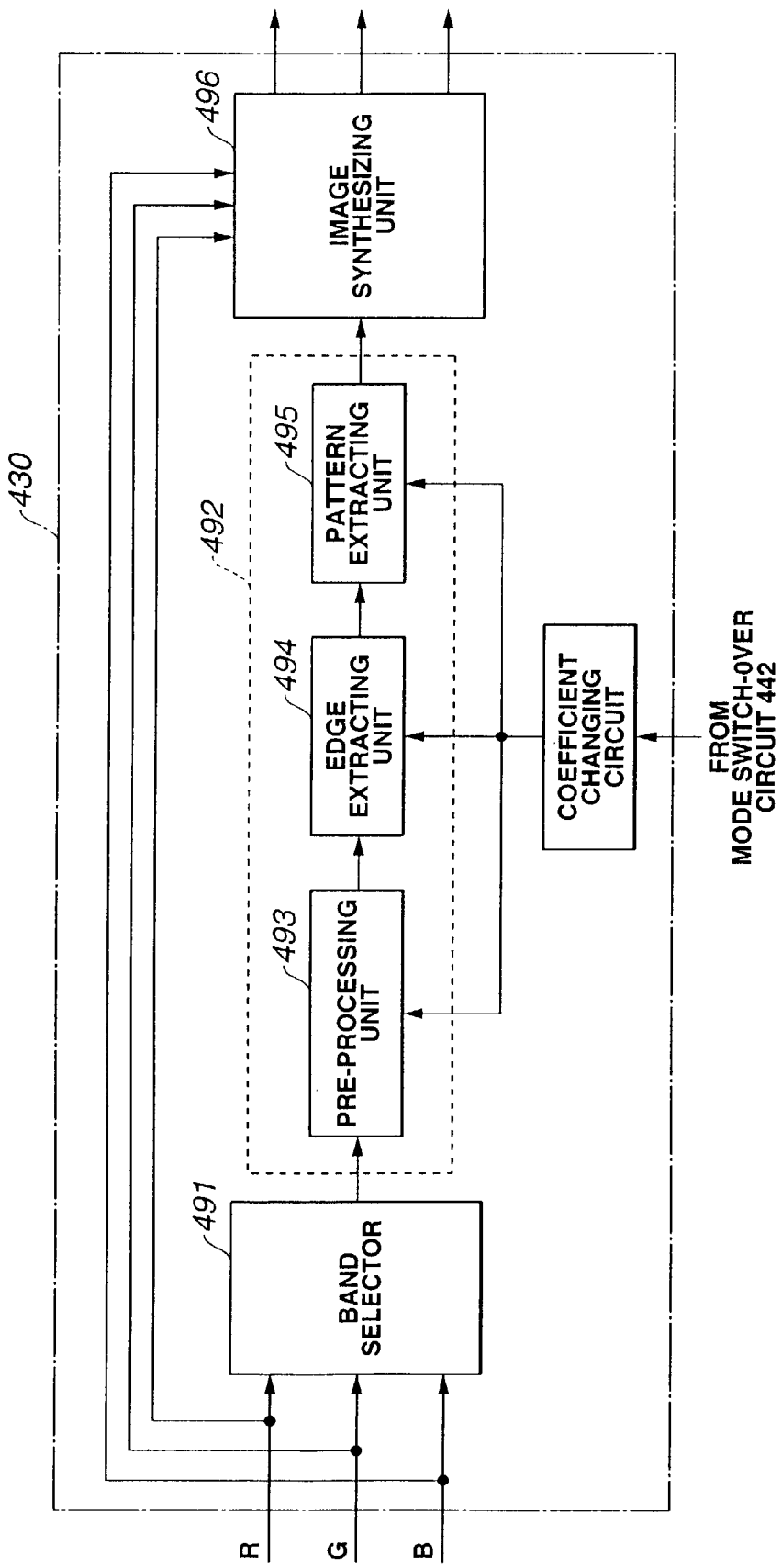
FIG. 100 is a configuration diagram illustrating the configuration of an image processing circuit according to a fifteenth embodiment of the present invention.
Figure 101:
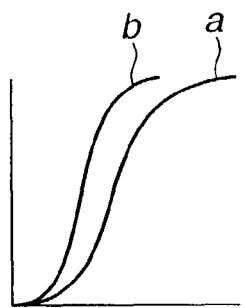
FIG. 101 is a diagram illustrating a tone correction table in the pre-processing unit in FIG. 100.
Figure 102:
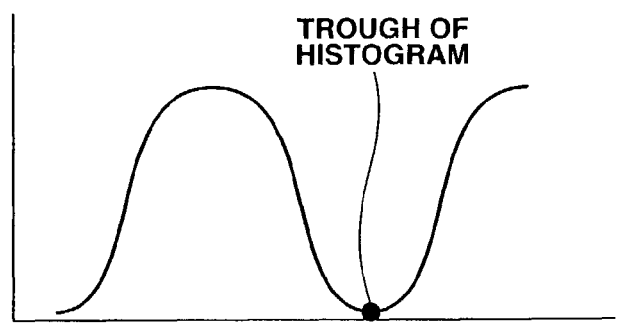
FIG. 102 is a diagram illustrating histogram distribution applied to edge extraction processing performed by the edge extraction processing unit shown in FIG. 100.
Figure 103:
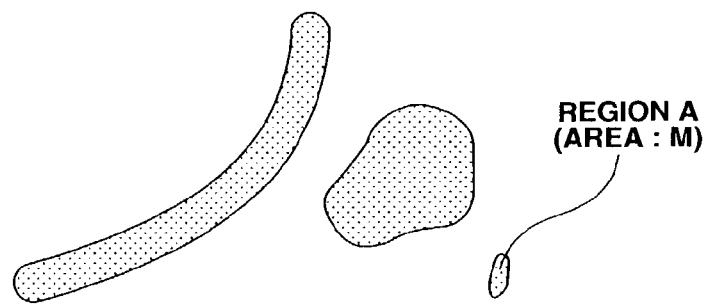
FIG. 103 is a diagram describing processing performed by the pattern extraction unit shown in FIG. 100.

FIG. 100 is a configuration diagram illustrating the configuration of an image processing circuit, FIG. 101 is a diagram illustrating a tone correction table in the pre-processing unit in FIG. 100, FIG. 102 is a diagram illustrating histogram distribution applied to edge extracting processing in the edge extracting processing unit shown in FIG. 100, and FIG. 103 is a diagram describing processing in the pattern extracting unit shown in FIG. 100.

The fifteenth embodiment is almost the same as the fourteenth embodiment, so only the differing points will be described, and the same configurations will be denoted with the same reference numerals and description thereof will be omitted.

The present embodiment illustrates a configuration which changes parameters for extracting angiography patterns or extracting minute structure patterns on mucous membrane surfaces in interlocking with filter switching. Narrow-band RGB images are characterized in that the independency of information represented between bands is high. For example, in the narrow-band observation mode wherein the mode switch-over switch 441 is pressed, differencial information is reflected between bands, such as shown in FIG. 99, wherein the B image reflects minute structure patterns on mucous membrane surfaces and blood vessel networks near the surface layer of mucous membranes, the G image reflects blood vessel networks existing near the middle layers, and the R image reflects relatively thicker blood vessel networks existing at deep layers of the mucous membranes, and each type of information is deeply related with the change of the living body tissue in the depth direction. With regard to such narrow-band RGB images, more effective results can be expected by further optimizing the parameters rather than applying pattern extraction processing in normal observation.

Accordingly, as shown in FIG. 100, the image processing circuit 430 according to the present embodiment comprises a band selector unit 491 for selecting each of the RGB band image data, which selects a band to apply to the processing in the subsequent pattern extracting processing unit 492, which comprises pre-processing unit 493, edge extracting processing unit 494, and pattern extracting unit 495.

Here, one band or multiple bands may be used, and selection is made according to extracted information. In the event that extraction of patterns of minute structures at the surface of mucous membranes is desired, the B image is selected here. Or, in the event that the position of thick blood vessels in layers of the mucous membranes is desired, the R image is selected.

In the pattern extracting processing unit 492, pre-processing is performed at the pre-processing unit 493. In general pre-processing, suitable pre-processing is performed according to subsequent processing, such as distortion correction, tone correction, and so forth. In the event of performing processing such as for angiography patterns, distortion correction processing for correcting distortion aberration of the image-pickup optical system, and histogram smoothing processing for standardizing concentration distribution is performed. For example, in the case of tone correction, a tone correction table F such as shown in FIG. 101 is applied to band data f(x, y) input to the pre-processing unit 493, to obtain output g(x, y) (=F(f(x, y)). Note that in the tone correction table in FIG. 101, curve b converts to a stronger contrast than curve a.

Next, in the edge extracting processing unit 494, edge extraction processing is performed. A method wherein a trough in a histogram distribution is discovered and binarization processing is performed at that level as shown in FIG. 102, or a method wherein edge extraction is performed using a differential operator, can be used for this.

Next, at the pattern extracting unit 495, assuming the area of the region A as M for example, as shown in FIG. 103, this M is compared with a predetermined threshold value ν, and in the event that M<θ, the region A is removed as an unnecessary pattern, and only patterns having regions of blood vessels and the like having area of θ or greater are extracted. Specifically, elimination and consolidation of patterns is performed by expansion or reduction processing, or collation with reference patterns.

With the series of processing performed at the pattern extracting processing unit 492, parameters must be optimized for each piece of information represented in each band. For example, in the pattern extracting unit 495, in the event that extracting blood vessels running at deep portions from the R image is desired, operations are made to eliminate fine independent points as much as possible, and in the event of extracting capillary angiography patterns from the B image, operations are made to leave the fine patterns as much as possible.

The processing results of the pattern extracting processing unit 492 are output to a final stage image synthesizing unit 496, and at the image synthesizing unit 496, image synthesizing for reflecting the pattern extracting results in the image is performed. Here, processing for adding the pattern extracting results to the original RGB image, or processing for configuring a monochromatic image from pattern extraction results alone, is performed.

The operations of the above-described image processing circuit 430 optimize the overall operations by the coefficient changing unit 473 changing the coefficients of the processing units based on control signals from the mode switch-over circuit 442 and processing switch-over instructing switch 470. With regard to the mode switch-over circuit 442, control is made so as to bypass pattern extracting processing in the case of normal RGB illumination, and pattern extraction processing based on control signals from the processing switch-over instructing switch 470 is performed in the image processing circuit 430 in the event of narrow-band RGB illumination.

Thus, according to the present embodiment as well, tissue information at a desired depth near the tissue surface of the living body tissue can be separated and visually recognized.

Embodiments of the present invention have thus been described, but it is needless to say that the present invention is by no means restricted to the above embodiments, and various modifications may be made within the spirit and scope of the present invention.

INDUSTRIAL APPLICABILITY

As described above, according to the present invention, firstly, an endoscope device and light source device capable of obtaining tissue information of a desired depth near the tissue surface of the living body tissue, can be provided.

Also, secondly, an endoscope device whereby tissue information of a desired depth near the tissue surface of the living body tissue can be separated and visually recognized, can be provided.

CROSS-REFERENCE TO RELATED APPLICATIONS

The present application is being applied claiming priority based on (1) Japanese Patent Application No. 2000-221312 applied in Japan on Jul. 21, 2000, (2) Japanese Patent Application No. 2000-227237 applied in Japan on Jul. 27, 2000, (3) Japanese Patent Application No. 2000-227238 applied in Japan on Jul. 27, 2000, and (4) Japanese Patent Application No. 2001-88256 applied in Japan on Mar. 26, 2001 claiming priority based on the aforementioned Japanese Patent Application No. 2000-221312 applied in Japan on Jul. 21, 2000, and the contents disclosed in the aforementioned (1) through (4) have been referenced to in the present specification, claims, and drawings.

The invention claimed is:

1. An endoscope device, comprising:
illumination light generating means for generating illumination light for irradiating a subject;
an endoscope having image-pickup means for capturing an image of said subject by return light from the subject;
band restricting means provided on an optical path from said illumination light generating means to said image-pickup means for restricting at least one of the plurality of wavelength regions of said illumination light based on penetration depths of light with respect to the subject for irradiating illumination light of a band with a discrete spectral distribution to said subject and for performing image formation of a band image by return light of the illumination light with the spectral distribution from different depths of tissue layers of said subject on said image-pickup means, said band restricting means comprising:
a first filter set having a plurality of wide-band filters, each wide-band filter being disposed for allowing transmission of a wide band of wavelengths, said wide band of wavelengths of said each wide-band filter being substantially overlapping with respect to said wide band of wavelengths of at least one other wide-band filter of said plurality of wide-band filters;
a second filter set having a plurality of narrow-band filters, each narrow-band filter being disposed for allowing transmission of light of a narrow band of wavelengths, a transmission band of wavelengths of said each narrow-band filter being discretely restricted with respect to transmission bands of wavelengths of other narrow-band filters, and one of the plurality of narrow-band filters including a specific wavelength bandwidth with a full width at half maximum of 20 to 40 nm; and
signal processing means for processing signals outputted from said image-pickup means in order to display an observation image of the subject based on a band image of a discrete spectral distribution of said subject formed on said image-pickup means, wherein the second filter set includes
a first narrow-band filter having a transmission band including 420 nm, and
a second narrow-band filter having a transmission band including 540 nm and of a full width at half maximum of 20-40 nm.

2. The endoscope device according to claim 1, further comprising light quantity adjusting means for adjusting the quantity of light of said illumination light for each of said wavelength regions, according to restriction by said band restricting means.

3. The endoscope device according to claim 1, wherein the transmission band of wavelengths of at least one of said narrow-band filters includes a wavelength of 420 nm.

4. An endoscope device, comprising:
illumination light generating means for generating illumination light for irradiating a subject;
an endoscope having image-pickup means for capturing an image of said subject by return light from the subject;
band restricting means provided on an optical path from said illumination light generating means to said image-pick means for restricting at least one of the plurality of wavelength regions of said illumination light based on penetration depths of light with respect to the subject for irradiating illumination light of a band with a discrete spectral distribution to said subject and for performing image formation of a band image by return light of the illumination light with the spectral distribution from different depths of tissue layers of said subject on said image-pickup means, said band restricting means comprising:
a first filter set having a plurality of wide-band filters, each wide-band filter being disposed for allowing transmission of a wide band of wavelengths, said wide band of wavelengths of said each wide-band filter being substantially overlapping with respect to said wide band of wavelengths of at least one other wide-band filter of said plurality of wide-band filters;
a second filter set having a plurality of narrow-band filters, each narrow-band filter being disposed for allowing transmission of light of a narrow band of wavelengths, a transmission band of wavelengths of said each narrow-band filter being discretely restricted with respect to transmission bands of wavelengths of other narrow-band filters, and one of the plurality of narrow-band filters including a specific wavelength bandwidth with a full width at half maximum of 20 to 40 nm;
band restriction placement means for detachably placing said band restricting means on said optical path; and
signal processing means for processing signals outputted from said image-pickup means in order to display an observation image of said subject based on a band image of a discrete spectral distribution of said subject formed on said image-pickup means, said signal processing means performing the processing to adjust color for said image-pickup signals according to the placement state of said band restricting means by said band restriction placement means,
wherein the second filter set includes
a first narrow-band filter having a transmission band including 420 nm, and
a second narrow-band filter having a transmission band including 540 nm and of a full width at half maximum of 20-40 nm.

5. The endoscope device according to claim 4, further comprising light quantity adjusting means for adjusting the quantity of light of said illumination light for each of said wavelength regions, according to restriction by said band restricting means.

6. An endoscope device, comprising:
illumination light generating means for generating illumination light for irradiating a subject;
an endoscope having image-pickup means for capturing an image of said subject by return light from the subject;
band restriction placement means for selectively placing, on an optical path from said illumination light generating means to said image-pickup means, band restricting means for restricting at least one of the plurality of wavelength regions of said illumination light based on penetration depths of light with respect to the subject, for irradiating illumination light of a band with a discrete spectral distribution to said subject, and forming a band image by return light of the illumination light with the spectral distribution from different depths of tissue layers of said subject on said image-pickup means, said band restricting means comprising:

a first filter set having a plurality of wide-band filters, each wide-band filter being disposed for allowing transmission of a wide band of wavelengths, said wide band of wavelengths of said each wide-band filter being substantially overlapping with respect to said wide band of wavelengths of at least one other wide-band filter of said plurality of wide-band filters; and a second filter set having a plurality of narrow-band filters, each narrow-band filter being disposed for allowing transmission of light of a narrow band of wavelengths, a transmission band of wavelengths of said each narrow-band filter being discretely restricted with respect to transmission bands of wavelengths of other narrow-band filters, and one of the plurality of narrow-band filters including a specific wavelength bandwidth with a full width at half maximum of 20 to 40 nm; and signal processing means for processing signals outputted from said image-pickup means in order to display an observation image of said subject based on a band image of a discrete spectral distribution of said subject formed on said image-pickup means, wherein said signal processing means change the signal processing for said image-pickup signals according to the placement state of said band restricting means by said band restriction placement means, and wherein the second filter set includes a first narrow-band filter having a transmission band including 420 nm, and a second narrow-band filter having a transmission band including 540 nm and of a full width at half maximum of 20-40 nm.

7. The endoscope device according to claim 6, further comprising light quantity adjusting means for adjusting the quantity of light of said illumination light for each of said wavelength regions, according to restriction by said band restricting means.

8. An endoscopic device, comprising:

a light source for generating illumination light for irradiating a subject;

an image-pickup element for capturing an image of said subject by return light of said illumination light from said subject;

a band restricting member provided on an optical path from said light source to said image-pickup element for restricting at least a part of wavelength regions of said illumination light based on penetration depths of light with respect to the subject for irradiating illumination light of a band with a discrete spectral distribution to said subject and for performing image formation of a band image by return light of the illumination light with the spectral distribution from different depths of tissue layers of said subject on said image-pickup element, said band restricting member comprising:

a first filter member having at least a first filter, a second filter and a third filter, each filter being disposed for allowing transmission of a wide band of wavelengths, said wide band of wavelengths of each filter being substantially overlapping with respect to said wide band of wavelengths of at least one other filter of said first filter member; and a second filter member having a plurality of narrow-band filters, each narrow-band filter being disposed for allowing transmission of light of a narrow band of wavelengths, a transmission band of wavelengths of each narrow-band filter being discretely restricted with respect to transmission bands of wavelengths of other narrow-band filters, and one of the plurality of narrow-band filters including a specific wavelength bandwidth with a full width at half maximum of 20 to 40 nm; and a signal processing unit for processing signals outputted from said image-pickup element in order to display an observation image of said subject based on a band image of substantially discrete spectral distribution of said subject formed in said image-pickup element, wherein the second filter member includes a first narrow-band filter having a transmission band including 420 nm, and a second narrow-band filter having a transmission band including 540 nm and of a full width at half maximum of 20-40 nm.

9. The endoscope device according to claim 8, further comprising: a rotating member for rotating said first filter member to selectively place said first filter, second filter and third filter on an optical path from said light source to said subject, thereby to successively illuminate the subject with said illumination light in the corresponding wavelength band;

wherein said image-pickup element captures images of said subject based on said illumination light in the plurality of wavelength bands corresponding to each of filter of said first filter member successively irradiated onto said subject; and the signal processing unit processes said signals so as to synthesize and display said images of the subject which is successively illuminated with said illumination light in the plurality of wavelength bands corresponding to each filter of said first filter member and is captured by said image-pickup element.

10. The endoscope device according to claim 9, wherein said band restricting member is provided on an optical path from said light source to said subject and restricts at least a part of wavelength regions of said illumination light so that said illumination light irradiated onto said subject may have a substantially discrete spectral distribution.

11. The endoscope device according to claim 9, further comprising a switching member for selectively placing said band restricting member on said optical path in order to switch the illumination light irradiated onto said subject between wavelength bands corresponding to at least one of said plurality of narrow-band filters of said second filter member and wavelength bands corresponding to at least one of said filters of said first filter member.

12. The endoscope device according to claim 8, wherein said image-pickup element includes a color CCD.

13. The endoscope device according to claim 12, wherein said band restricting member is provided on an optical path from said light source to said subject and restricts at least a part of wavelength regions of said illumination light so that said illumination light irradiated onto said subject may have a substantially discrete spectral distribution.

14. The endoscope device according to claim 13, further comprising a switching member for selectively placing said band restricting member on said optical path.

15. An endoscope device, comprising:

illumination light supplying means for supplying illumination light including visible light region;

an endoscope having image-pickup means for irradiating the illumination light on a subject and capturing an image of the subject by return light;

signal processing means for signal processing image-pickup signals from the image pickup means; and band restricting means provided upon an optical path from the illumination light supplying means to the image-pickup means for narrowing a band of at least one of a plurality of wavelength regions of the illumination light which are distributed based on penetration depths of light with respect to the subject to include a specific wavelength bandwidth with a full width at half maximum of 20 to 40 nm, and to restrict wavelength regions such that the narrowed band is discrete with respect to other wavelength regions, wherein the signal processing means performs a predetermined color conversion processing to the image-pickup signal of which the band of the wavelength region is restricted by the band restricting means.

16. The endoscope device according to claim 15, further comprising light quantity adjusting means for adjusting the quantity of light of said illumination light for each of said wavelength regions, according to restriction by said band restricting means.

17. The endoscope device according to claim 15, wherein a transmission band of wavelengths narrowed by said band restricting means includes a wavelength band of 420 nm.

18. An endoscope device, comprising:
illumination light supplying unit for supplying illumination light including visible light region;
an endoscope having image-pickup element for irradiating the illumination light on a subject and capturing an image of the subject by return light;
signal processing unit for signal processing image-pickup signals from the image-pickup element; and
band restricting member provided upon an optical path from the illumination light supplying unit to the image-pickup element for narrowing a band of at least one of a plurality of wavelength regions of the illumination light which are distributed based on penetration depths of light with respect to the subject to include a specific wavelength bandwidth with a full width at half maximum of 20 to 40 nm, and to restrict wavelength regions such that the narrowed band is discrete with respect to other wavelength regions, wherein the signal processing unit performs a predetermined color conversion processing to the image-pickup signal of which the band of the wavelength region is restricted by the band restricting member.

19. The endoscope device according to claim 18, wherein said image-pickup element includes a color CCD.

20. The endoscope device according to claim 18, wherein said band restricting member is provided on an optical path from said light source to said subject and restricts at least a part of wavelength regions of said illumination light so that said illumination light irradiated onto said subject may have a substantially discrete spectral distribution.

21. The endoscope device according to claim 18, further comprising a switching member for selectively placing said band restricting member on said optical path.

22. An endoscope device, comprising:
illumination light generating means for generating illumination light for irradiating a subject;
an endoscope having image-pickup means for capturing an image of said subject by return light from the subject;
band selection means provided on an optical path from said illumination light generating means to said image-pickup means for using at least one of a plurality of wavelength regions of said illumination light in accordance with penetration depths of light with respect to the subject for irradiating illumination light of a band with a discrete spectral distribution to said subject and performing image formation of a band image by return light of the illumination light with the spectral distribution from different depths of tissue layers of said subject on said image-pickup means, said band selection means comprising:
a first filter set having a plurality of wide-band filters, each wide-band filter being disposed for allowing transmission of a wide band of wavelengths, said wide band of wavelengths of said each wide-band filter being substantially overlapping with respect to said wide band of wavelengths of at least one other wide-band filter of said plurality of wide-band filters; and
a second filter set having a plurality of narrow-band filters, each narrow-band filter being disposed for allowing transmission of light of a narrow band of wavelengths, a transmission band of wavelengths of said each narrow-band filter being discretely restricted with respect to transmission bands of wavelengths of other narrow-band filters, and one of the plurality of narrow-band filters including a specific wavelength bandwidth with a full width at half maximum of 20 to 40 nm; and
signal processing means for processing signals outputted from said image-pickup means in order to display an observation image of the subject based on a band image of a discrete spectral distribution of said subject formed on said image-pickup means, wherein the second filter set includes
a first narrow-band filter having a transmission band including 420 nm, and
a second narrow-band filter having a transmission band including 540 nm and of a full width at half maximum of 20-40 nm.

23. The endoscope device according to claim 22, further comprising light quantity adjusting means for adjusting the quantity of light of said illumination light for each of said wavelength regions, according to selection by said band selection means.

24. An endoscope device, comprising:
illumination light generating means for generating illumination light for irradiating a subject;
an endoscope having image-pickup means for capturing an image of said subject by return light from the subject;
band restricting means provided on an optical path from said illumination light generating means to said image-pickup means for restricting at least one of the plurality of wavelength regions of said illumination light based on penetration depths of light with respect to the subject for irradiating illumination light of a band with a discrete spectral distribution to said subject and for performing image formation of a band image by return light of the illumination light with the spectral distribution from different depths of tissue layers of said subject on said image-pickup means, said band restricting means comprising:
a first filter set having a plurality of wide-band filters, each wide-band filter being disposed for allowing transmission of a wide band of wavelengths, said wide band of wavelengths of said each wide-band filter being substantially overlapping with respect to said wide band of wavelengths of at least one other wide-band filter of said plurality of wide-band filters;
a second filter set having a plurality of narrow-band filters, each narrow-band filter being disposed for allowing transmission of light of a narrow band of wavelengths, a transmission band of wavelengths of said each narrow-band filter being discretely restricted with respect to transmission bands of wavelengths of other narrow-band filters, and one of the plurality of narrow-band filters including a specific wavelength bandwidth with a full width at half maximum of 20 to 40 nm; and signal processing means for processing signals outputted from said image-pickup means in order to display an observation image of the subject based on a band image of a discrete spectral distribution of said subject formed on said image-pickup means, wherein said second filter set includes a first narrow-band filter having a transmission band of wavelengths including a wavelength of 600 nm and having a full width at half maximum of 20 to 40 nm and a second narrow-band filter having a transmission band of wavelengths including a wavelength of 420 nm and having a full width at half maximum of 20 to 40 nm.

25. An endoscope device, comprising:

illumination light generating means for generating illumination light for irradiating a subject;

an endoscope having image-pickup means for capturing an image of said subject by return light from the subject;

band restricting means provided on an optical path from said illumination light generating means to said image-pickup means for restricting at least one of the plurality of wavelength regions of said illumination light based on penetration depths of light with respect to the subject for irradiating illumination light of a band with a discrete spectral distribution to said subject and for performing image formation of a band image by return light of the illumination light with the spectral distribution from different depths of tissue layers of said subject on said image-pickup means, said band restricting means comprising:

a first filter set having a plurality of wide-band filters, each wide-band filter being disposed for allowing transmission of a wide band of wavelengths, said wide band of wavelengths of said each wide-band filter being substantially overlapping with respect to said wide band of wavelengths of at least one other wide-band filter of said plurality of wide-band filters;

a second filter set having a plurality of narrow-band filters, each narrow-band filter being disposed for allowing transmission of light of a narrow band of wavelengths, a transmission band of wavelengths of said each narrow-band filter being discretely restricted with respect to transmission bands of wavelengths of other narrow-band filters, and one of the plurality of narrow-band filters including a specific wavelength bandwidth with a full width at half maximum of 20 to 40 nm; and signal processing means for processing signals outputted from said image-pickup means in order to display an observation image of the subject based on a band image of a discrete spectral distribution of said subject formed on said image-pickup means, wherein said second filter set includes a first narrow-band filter having a transmission band of wavelengths including a wavelength of 550 nm and having a full width at half maximum of 20 to 40 nm and a second narrow-band filter having a transmission band of wavelengths including a wavelength of 500 nm and having a full width at half maximum of 20 to 40 nm.

* * * * *

UNITED STATES PATENT AND TRADEMARK OFFICE
CERTIFICATE OF CORRECTION

| | | |
|---|---|---|
| PATENT NO. | : 7,892,169 B2 | |
| APPLICATION NO. | : 10/333155 | |
| DATED | : February 22, 2011 | |
| INVENTOR(S) | : Kazuhiro Gono et al. | |

It is certified that error appears in the above-identified patent and that said Letters Patent is hereby corrected as shown below:

Title Page
Item (30) Foreign Application Priority Data should read

--Jul. 21, 2000   (JP).......................2000-221312
　Jul. 27, 2000   (JP).......................2000-227237
　Jul. 27, 2000   (JP).......................2000-227238
　Mar. 26, 2001  (JP).......................2001-088256--

Signed and Sealed this
Third Day of May, 2011

David J. Kappos
*Director of the United States Patent and Trademark Office*